US011583342B2

(12) United States Patent
Kline et al.

(10) Patent No.: US 11,583,342 B2
(45) Date of Patent: Feb. 21, 2023

(54) VIRTUAL REALITY SURGICAL CAMERA SYSTEM

(71) Applicant: Vicarious Surgical Inc., Cambridge, MA (US)

(72) Inventors: Eric Kline, Cambridge, MA (US); Sammy Khalifa, Medford, MA (US); Marshall Wentworth, Somerville, MA (US); Eric Van Albert, Cambridge, MA (US)

(73) Assignee: Vicarious Surgical Inc., Waltham, MA (US)

( * ) Notice: Subject to any disclaimer, the term of this patent is extended or adjusted under 35 U.S.C. 154(b) by 1034 days.

(21) Appl. No.: 16/130,734

(22) Filed: Sep. 13, 2018

(65) Prior Publication Data

US 2019/0076199 A1 Mar. 14, 2019

Related U.S. Application Data

(60) Provisional application No. 62/558,583, filed on Sep. 14, 2017.

(51) Int. Cl.
*A61B 34/20* (2016.01)
*G02B 27/01* (2006.01)
(Continued)

(52) U.S. Cl.
CPC .............. *A61B 34/20* (2016.02); *A61B 17/34* (2013.01); *A61B 17/3415* (2013.01);
(Continued)

(58) Field of Classification Search
CPC ......... A61B 34/20; A61B 17/34; A61B 34/76; A61B 90/36; A61B 90/37; A61B 34/30;
(Continued)

(56) References Cited

U.S. PATENT DOCUMENTS 2,053,868 A 9/1936 Grosso
2,313,164 A 3/1943 Nelson
(Continued)

FOREIGN PATENT DOCUMENTS

JP 2005-288174 A 10/2005
WO WO-2007/111571 A1 10/2007
(Continued)

OTHER PUBLICATIONS

Can, S., et al., "The "Highly Versatile Single Port System" for laparpscopic surgery: Introduction and first clinical application," 4th European Conference of the International Federation for Medical and Biological Engineering, vol. 22, pp. 1650-1654 (2009).
(Continued)

*Primary Examiner* — Maurice L. McDowell, Jr.
(74) *Attorney, Agent, or Firm* — McCarter & English, LLP; David R. Burns; Nathan D. Harrison

(57) ABSTRACT

A system includes a console assembly, a trocar assembly operably coupled to the console assembly, a camera assembly operably coupled to the console assembly having a stereoscopic camera assembly, and at least one rotational positional sensor configured to detect rotation of the stereoscopic camera assembly about at least one of a pitch axis or a yaw axis. The console assembly includes a first actuator and a first actuator pulley operable coupled to the first actuator. The trocar assembly includes a trocar having an inner and outer diameter, and a seal sub-assembly comprising at least one seal and the seal sub-assembly operably coupled to the trocar. The camera assembly includes a camera support tube having a distal and a proximal end, the stereoscopic camera operably coupled to the distal end of the support tube and a first and second camera module having a first and second optical axis.

38 Claims, 41 Drawing Sheets

(51) Int. Cl.
*G02B 7/00* (2021.01)
*H04N 13/366* (2018.01)
*H04N 13/239* (2018.01)
*H04N 13/344* (2018.01)
*A61B 90/00* (2016.01)
*H04N 13/279* (2018.01)
*A61B 17/34* (2006.01)
*A61B 34/00* (2016.01)
*H04N 13/327* (2018.01)
*A61B 17/00* (2006.01)
*A61B 90/50* (2016.01)
*A61B 90/30* (2016.01)
*A61B 34/30* (2016.01)
*H04N 5/225* (2006.01)

(52) U.S. Cl.
CPC .............. *A61B 34/71* (2016.02); *A61B 34/76* (2016.02); *A61B 90/36* (2016.02); *A61B 90/37* (2016.02); *G02B 7/002* (2013.01); *G02B 27/017* (2013.01); *H04N 13/239* (2018.05); *H04N 13/279* (2018.05); *H04N 13/344* (2018.05); *H04N 13/366* (2018.05); *A61B 34/30* (2016.02); *A61B 2017/00398* (2013.01); *A61B 2034/2048* (2016.02); *A61B 2034/2055* (2016.02); *A61B 2034/2057* (2016.02); *A61B 2034/2072* (2016.02); *A61B 2034/304* (2016.02); *A61B 2090/306* (2016.02); *A61B 2090/309* (2016.02); *A61B 2090/365* (2016.02); *A61B 2090/371* (2016.02); *A61B 2090/372* (2016.02); *A61B 2090/502* (2016.02); *A61B 2560/0266* (2013.01); *A61B 2562/166* (2013.01); *H04N 13/327* (2018.05); *H04N 2005/2255* (2013.01); *H04N 2213/001* (2013.01)

(58) Field of Classification Search
CPC .. A61B 2017/00398; A61B 2034/2048; A61B 2034/2055; A61B 2034/2057; A61B 2034/2072; A61B 2090/306; A61B 2090/309; A61B 2090/365; A61B 2090/371; A61B 2090/372; A61B 2090/502; A61B 2034/2059; A61B 17/3415; A61B 34/71; A61B 2034/304; A61B 2560/0266; A61B 2562/166; G02B 7/002; G02B 27/017; G02B 23/2415; G02B 23/2476; H04N 13/239; H04N 13/279; H04N 13/344; H04N 13/366; H04N 13/327; H04N 2005/2255; H04N 2213/001
See application file for complete search history.

(56) References Cited

U.S. PATENT DOCUMENTS

| | | |
|---|---|---|
| 4,563,812 A | 1/1986 | Goddard-Watts |
| 4,573,452 A | 3/1986 | Greenberg |
| 4,620,362 A | 11/1986 | Reynolds |
| 4,676,142 A | 6/1987 | McCormick et al. |
| 4,843,921 A | 7/1989 | Kremer |
| 5,203,646 A | 4/1993 | Landsberger et al. |
| 5,368,015 A | 11/1994 | Wilk |
| 5,507,297 A | 4/1996 | Slater et al. |
| 5,515,478 A | 5/1996 | Wang |
| 5,546,508 A | 8/1996 | Jain et al. |
| 5,593,402 A | 1/1997 | Patrick |
| 5,624,398 A | 4/1997 | Smith |
| 5,755,661 A | 5/1998 | Schwartzman |
| 5,797,900 A | 8/1998 | Madhani et al. |
| 5,825,982 A | 10/1998 | Wright et al. |
| 5,836,869 A | 11/1998 | Kudo et al. |
| 5,876,325 A | 3/1999 | Mizuno et al. |
| 5,911,036 A | 6/1999 | Wright et al. |
| 6,132,368 A | 10/2000 | Cooper |
| 6,162,172 A | 12/2000 | Cosgrove et al. |
| 6,377,011 B1 | 4/2002 | Ben-Ur |
| 6,441,577 B2 | 8/2002 | Blumenkranz et al. |
| 6,459,926 B1 | 10/2002 | Nowlin et al. |
| 6,491,701 B2 | 12/2002 | Tierney et al. |
| 6,556,741 B1 | 4/2003 | Fan |
| 6,587,750 B2 | 7/2003 | Gerbi et al. |
| 6,594,552 B1 | 7/2003 | Nowlin et al. |
| 6,659,939 B2 | 12/2003 | Moll et al. |
| 6,676,684 B1 | 1/2004 | Morley et al. |
| 6,682,287 B2 | 1/2004 | Glass et al. |
| 6,714,841 B1 | 3/2004 | Wright et al. |
| 6,725,866 B2 | 4/2004 | Johnson et al. |
| 6,783,524 B2 | 8/2004 | Anderson et al. |
| 6,788,018 B1 | 9/2004 | Blumenkranz |
| 6,817,974 B2 | 11/2004 | Cooper et al. |
| 6,858,003 B2 | 2/2005 | Evans et al. |
| 6,860,878 B2 | 3/2005 | Brock |
| 6,963,792 B1 | 11/2005 | Green |
| 6,965,812 B2 | 11/2005 | Wang et al. |
| 6,969,385 B2 | 11/2005 | Moreyra |
| 7,042,184 B2 | 5/2006 | Oleynikov et al. |
| 7,121,781 B2 | 10/2006 | Sanchez |
| 7,125,403 B2 | 10/2006 | Julian et al. |
| 7,126,303 B2 | 10/2006 | Farritor et al. |
| 7,185,657 B1 | 3/2007 | Johnson et al. |
| 7,199,545 B2 | 4/2007 | Oleynikov et al. |
| 7,208,005 B2 | 4/2007 | Frecker et al. |
| 7,239,940 B2 | 7/2007 | Wang et al. |
| 7,297,142 B2 | 11/2007 | Brock |
| 7,339,341 B2 | 3/2008 | Oleynikov et al. |
| 7,367,973 B2 | 5/2008 | Manzo et al. |
| 7,372,229 B2 | 5/2008 | Farritor et al. |
| 7,594,912 B2 | 9/2009 | Cooper et al. |
| 7,691,058 B2 | 4/2010 | Rioux et al. |
| 7,717,890 B2 | 5/2010 | Drogue et al. |
| 7,736,356 B2 | 6/2010 | Cooper et al. |
| 7,763,015 B2 | 7/2010 | Cooper et al. |
| 7,772,796 B2 | 8/2010 | Farritor et al. |
| 7,778,733 B2 | 8/2010 | Nowlin et al. |
| 7,831,292 B2 | 11/2010 | Quaid et al. |
| 7,854,738 B2 | 12/2010 | Lee et al. |
| 7,862,502 B2 | 1/2011 | Pool et al. |
| 7,862,580 B2 | 1/2011 | Cooper et al. |
| 7,950,306 B2 | 5/2011 | Stuart |
| 7,981,025 B2 | 7/2011 | Pool et al. |
| 8,016,845 B1 | 9/2011 | Sauer |
| 8,066,644 B2 | 11/2011 | Sarkar et al. |
| RE43,049 E | 12/2011 | Grace |
| 8,073,335 B2 | 12/2011 | Labonville et al. |
| 8,088,062 B2 | 1/2012 | Zwolinski |
| 8,120,301 B2 | 2/2012 | Goldberg et al. |
| 8,123,740 B2 | 2/2012 | Madhani et al. |
| 8,142,421 B2 | 3/2012 | Cooper et al. |
| 8,241,271 B2 | 8/2012 | Millman et al. |
| 8,246,533 B2 | 8/2012 | Chang et al. |
| 8,303,576 B2 | 11/2012 | Brock |
| 8,317,778 B2 | 11/2012 | Spaide |
| 8,333,780 B1 | 12/2012 | Pedros et al. |
| 8,343,171 B2 | 1/2013 | Farritor et al. |
| 8,375,808 B2 | 2/2013 | Blumenkranz et al. |
| 8,377,044 B2 | 2/2013 | Coe et al. |
| 8,398,541 B2 | 3/2013 | DiMaio et al. |
| 8,398,634 B2 | 3/2013 | Manzo et al. |
| 8,400,094 B2 | 3/2013 | Schena |
| 8,409,234 B2 | 4/2013 | Stabler et al. |
| 8,418,073 B2 | 4/2013 | Mohr et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,518,024 B2 | 8/2013 | Williams et al. |
| 8,540,748 B2 | 9/2013 | Murphy et al. |
| 8,551,076 B2 | 10/2013 | Duval et al. |
| 8,551,114 B2 | 10/2013 | Ramos de la Pena |

(56) References Cited

U.S. PATENT DOCUMENTS

| | | |
|---|---|---|
| 8,600,551 B2 | 12/2013 | Itkowitz et al. |
| 8,604,742 B2 | 12/2013 | Farritor et al. |
| 8,613,230 B2 | 12/2013 | Blumenkranz et al. |
| 8,620,473 B2 | 12/2013 | Diolaiti et al. |
| 8,623,028 B2 | 1/2014 | Rogers et al. |
| 8,641,700 B2 | 2/2014 | Devengenzo et al. |
| 8,667,860 B2 | 3/2014 | Helmer et al. |
| 8,679,096 B2 | 3/2014 | Farritor et al. |
| 8,682,489 B2 | 3/2014 | Itkowitz et al. |
| 8,706,301 B2 | 4/2014 | Zhao et al. |
| 8,715,159 B2 | 5/2014 | Pool et al. |
| 8,721,539 B2 | 5/2014 | Shohat et al. |
| 8,747,394 B2 | 6/2014 | Belson et al. |
| 8,758,391 B2 | 6/2014 | Swayze et al. |
| 8,761,930 B2 | 6/2014 | Nixon |
| 8,768,516 B2 | 7/2014 | Diolaiti et al. |
| 8,776,632 B2 | 7/2014 | Gao et al. |
| 8,792,951 B1 | 7/2014 | Mao et al. |
| 8,808,163 B2 | 8/2014 | Pool et al. |
| 8,827,988 B2 | 9/2014 | Belson et al. |
| 8,827,996 B2 | 9/2014 | Scott et al. |
| 8,828,024 B2 | 9/2014 | Farritor et al. |
| 8,834,488 B2 | 9/2014 | Farritor et al. |
| 8,844,789 B2 | 9/2014 | Shelton, IV et al. |
| 8,852,174 B2 | 10/2014 | Burbank |
| 8,858,538 B2 | 10/2014 | Belson et al. |
| 8,876,857 B2 | 11/2014 | Burbank |
| 8,882,660 B2 | 11/2014 | Phee et al. |
| 8,894,633 B2 | 11/2014 | Farritor et al. |
| 8,911,428 B2 | 12/2014 | Cooper et al. |
| 8,912,746 B2 | 12/2014 | Reid et al. |
| 8,919,348 B2 | 12/2014 | Williams et al. |
| 8,932,208 B2 | 1/2015 | Kendale et al. |
| 8,936,544 B2 | 1/2015 | Shahoian et al. |
| 8,942,828 B1 | 1/2015 | Schecter |
| 8,944,997 B2 | 2/2015 | Fernandez et al. |
| 8,945,095 B2 | 2/2015 | Blumenkranz et al. |
| 8,945,163 B2 | 2/2015 | Voegele et al. |
| 8,945,174 B2 | 2/2015 | Blumenkranz |
| 8,956,351 B2 | 2/2015 | Ravikumar et al. |
| 8,968,332 B2 | 3/2015 | Farritor et al. |
| 8,974,374 B2 | 3/2015 | Schostek et al. |
| 8,979,857 B2 | 3/2015 | Stad et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,565 B2 | 3/2015 | Brisson et al. |
| 8,992,566 B2 | 3/2015 | Baldwin |
| 8,996,173 B2 | 3/2015 | Itkowitz et al. |
| 9,002,518 B2 | 4/2015 | Manzo et al. |
| 9,005,112 B2 | 4/2015 | Hasser et al. |
| 9,011,434 B2 | 4/2015 | Kappel et al. |
| 9,028,468 B2 | 5/2015 | Scarfogliero et al. |
| 9,028,494 B2 | 5/2015 | Shelton, IV et al. |
| 9,039,685 B2 | 5/2015 | Larkin et al. |
| 9,044,256 B2 | 6/2015 | Cadeddu et al. |
| 9,052,710 B1 | 6/2015 | Farwell |
| 9,055,960 B2 | 6/2015 | Stoy et al. |
| 9,060,678 B2 | 6/2015 | Larkin et al. |
| 9,060,770 B2 | 6/2015 | Shelton, IV et al. |
| 9,077,973 B2 | 7/2015 | Aguren |
| 9,078,684 B2 | 7/2015 | Williams |
| 9,078,695 B2 | 7/2015 | Hess et al. |
| 9,089,352 B2 | 7/2015 | Jeong |
| 9,089,353 B2 | 7/2015 | Farritor et al. |
| 9,095,317 B2 | 8/2015 | Cooper et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,107,686 B2 | 8/2015 | Moon et al. |
| 9,119,655 B2 | 9/2015 | Bowling et al. |
| 9,144,452 B2 | 9/2015 | Scott et al. |
| 9,155,764 B1 | 10/2015 | Ahn et al. |
| 9,173,643 B2 | 11/2015 | Morley et al. |
| 9,173,707 B2 | 11/2015 | Singh |
| 9,173,915 B1 | 11/2015 | Kador |
| 9,179,912 B2 | 11/2015 | Yates et al. |
| 9,179,979 B2 | 11/2015 | Jinno |
| 9,186,215 B2 | 11/2015 | Singh |
| 9,186,220 B2 | 11/2015 | Stefanchik et al. |
| 9,194,403 B2 | 11/2015 | Neyme |
| 9,198,714 B2 | 12/2015 | Worrell et al. |
| 9,216,062 B2 | 12/2015 | Duque et al. |
| 9,220,567 B2 | 12/2015 | Sutherland et al. |
| 9,226,750 B2 | 1/2016 | Weir et al. |
| 9,226,751 B2 | 1/2016 | Shelton, IV et al. |
| 9,226,761 B2 | 1/2016 | Burbank |
| 9,241,766 B2 | 1/2016 | Duque et al. |
| 9,259,274 B2 | 2/2016 | Prisco |
| 9,259,275 B2 | 2/2016 | Burbank |
| 9,261,172 B2 | 2/2016 | Solomon et al. |
| 9,271,857 B2 | 3/2016 | Pool et al. |
| 9,272,166 B2 | 3/2016 | Hartman et al. |
| 9,301,759 B2 | 4/2016 | Spivey et al. |
| 9,303,212 B2 | 4/2016 | Flegal |
| 9,305,123 B2 | 4/2016 | Leotta et al. |
| 9,308,011 B2 | 4/2016 | Chao et al. |
| 9,308,145 B2 | 4/2016 | Jackson |
| 9,309,094 B2 | 4/2016 | Hoffend, III |
| 9,314,153 B2 | 4/2016 | Stein et al. |
| 9,314,239 B2 | 4/2016 | Brown |
| 9,315,235 B1 | 4/2016 | Wood |
| 9,326,823 B2 | 5/2016 | McMillan et al. |
| 9,327,081 B2 | 5/2016 | Gobron et al. |
| 9,333,003 B2 | 5/2016 | Kappel et al. |
| 9,333,041 B2 | 5/2016 | Yeung et al. |
| 9,358,031 B2 | 6/2016 | Manzo |
| 9,358,075 B2 | 6/2016 | Kim et al. |
| 9,360,093 B2 | 6/2016 | Garner |
| 9,366,862 B2 | 6/2016 | Haddick et al. |
| 9,375,288 B2 | 6/2016 | Robinson et al. |
| 9,386,983 B2 | 7/2016 | Swensgard et al. |
| 9,393,017 B2 | 7/2016 | Flanagan et al. |
| 9,398,911 B2 | 7/2016 | Auld |
| 9,399,298 B2 | 7/2016 | Kang |
| 9,399,558 B2 | 7/2016 | Guernsey et al. |
| 9,402,688 B2 | 8/2016 | Min et al. |
| 9,403,281 B2 | 8/2016 | Farritor et al. |
| 9,404,734 B2 | 8/2016 | Ramamurthy et al. |
| 9,408,369 B2 | 8/2016 | Dubinsky |
| 9,408,607 B2 | 8/2016 | Cartledge et al. |
| 9,408,668 B2 | 8/2016 | Durant et al. |
| 9,456,735 B2 | 10/2016 | Hrayr et al. |
| 9,457,168 B2 | 10/2016 | Moll et al. |
| 9,460,880 B2 | 10/2016 | Melecio Ramirez et al. |
| 9,463,015 B2 | 10/2016 | Hausen |
| 9,463,059 B2 | 10/2016 | Suon et al. |
| 9,464,643 B2 | 10/2016 | Shu |
| 9,476,245 B2 | 10/2016 | Hansen |
| 9,486,241 B2 | 11/2016 | Zeiner et al. |
| 9,566,709 B2 | 2/2017 | Kwon et al. |
| 9,579,163 B2 | 2/2017 | Valdastri et al. |
| 9,801,618 B2 | 10/2017 | Sachs et al. |
| 11,006,975 B1 * | 5/2021 | Cohen .............. A61B 17/00234 |
| 2002/0049367 A1 | 4/2002 | Irion et al. |
| 2004/0231061 A1 | 11/2004 | Irvin et al. |
| 2005/0096502 A1 | 5/2005 | Khalili |
| 2006/0052669 A1 | 3/2006 | Hart |
| 2006/0178556 A1 | 8/2006 | Hasser et al. |
| 2007/0074584 A1 | 4/2007 | Talarico et al. |
| 2007/0265502 A1 | 11/2007 | Minosawa et al. |
| 2008/0000317 A1 | 1/2008 | Patton et al. |
| 2008/0004634 A1 | 1/2008 | Farritor et al. |
| 2008/0033450 A1 * | 2/2008 | Bayer ................ A61B 17/3421 606/108 |
| 2008/0064931 A1 | 3/2008 | Schena et al. |
| 2008/0147018 A1 * | 6/2008 | Squilla ............... A61B 1/00193 604/264 |
| 2008/0221591 A1 | 9/2008 | Farritor et al. |
| 2009/0076536 A1 | 3/2009 | Rentschler et al. |
| 2009/0112229 A1 | 4/2009 | Omori et al. |
| 2009/0157076 A1 | 6/2009 | Athas et al. |
| 2009/0171373 A1 | 7/2009 | Farritor et al. |
| 2009/0177452 A1 | 7/2009 | Ullrich et al. |

(56) References Cited

U.S. PATENT DOCUMENTS

| | | |
|---|---|---|
| 2009/0245600 A1 | 10/2009 | Hoffman et al. |
| 2009/0248041 A1 | 10/2009 | Williams et al. |
| 2010/0041938 A1 | 2/2010 | Stoianovici et al. |
| 2010/0174293 A1 | 7/2010 | Orban, III et al. |
| 2010/0179479 A1 | 7/2010 | Albrecht et al. |
| 2010/0245549 A1 | 9/2010 | Allen et al. |
| 2010/0331858 A1 | 12/2010 | Simaan et al. |
| 2011/0063428 A1* | 3/2011 | Sonnenschein .... A61B 1/00096 348/294 |
| 2011/0071347 A1 | 3/2011 | Rogers et al. |
| 2011/0184404 A1* | 7/2011 | Walberg ............. A61B 18/1445 606/41 |
| 2011/0202070 A1 | 8/2011 | Dario et al. |
| 2011/0230894 A1 | 9/2011 | Simaan et al. |
| 2011/0238080 A1 | 9/2011 | Ranjit et al. |
| 2012/0046525 A1 | 2/2012 | Russell et al. |
| 2012/0078053 A1 | 3/2012 | Phee et al. |
| 2012/0158015 A1* | 6/2012 | Fowler ................... A61B 34/32 606/130 |
| 2012/0190920 A1 | 7/2012 | Hasser et al. |
| 2012/0265214 A1 | 10/2012 | Bender et al. |
| 2012/0290134 A1 | 11/2012 | Zhao et al. |
| 2012/0316575 A1 | 12/2012 | Farin et al. |
| 2013/0023860 A1 | 1/2013 | Nagashimada |
| 2013/0066136 A1* | 3/2013 | Palese ..................... A61B 34/73 600/11 |
| 2013/0085510 A1 | 4/2013 | Stefanchik et al. |
| 2013/0107665 A1 | 5/2013 | Fletcher et al. |
| 2013/0131695 A1 | 5/2013 | Scarfogliero et al. |
| 2013/0281924 A1 | 10/2013 | Shellenberger |
| 2013/0321262 A1 | 12/2013 | Schecter |
| 2014/0005640 A1 | 1/2014 | Shelton, IV et al. |
| 2014/0012287 A1 | 1/2014 | Oyola et al. |
| 2014/0066955 A1 | 3/2014 | Farritor et al. |
| 2014/0107417 A1* | 4/2014 | McKinley ............... A61B 90/30 600/112 |
| 2014/0107665 A1 | 4/2014 | Shellenberger et al. |
| 2014/0114327 A1 | 4/2014 | Boudreaux et al. |
| 2014/0142377 A1 | 5/2014 | Yang et al. |
| 2014/0222020 A1 | 8/2014 | Bender et al. |
| 2014/0276667 A1 | 9/2014 | Shellenberger et al. |
| 2014/0276944 A1 | 9/2014 | Farritor et al. |
| 2015/0026537 A1 | 1/2015 | Romanovskyy et al. |
| 2015/0038984 A1 | 2/2015 | Hiroe et al. |
| 2015/0073223 A1 | 3/2015 | Pravongviengkham et al. |
| 2015/0085095 A1 | 3/2015 | Tesar |
| 2015/0119638 A1 | 4/2015 | Yu et al. |
| 2015/0130599 A1 | 5/2015 | Berkley et al. |
| 2015/0250546 A1 | 9/2015 | Larkin et al. |
| 2015/0272694 A1* | 10/2015 | Charles ................. A61B 90/98 600/202 |
| 2016/0038008 A1* | 2/2016 | Molnar ............... A61B 1/00137 600/110 |
| 2016/0184032 A1 | 6/2016 | Romo et al. |
| 2016/0234408 A1 | 8/2016 | Urakawa et al. |
| 2016/0332305 A1 | 11/2016 | Gonzalez et al. |
| 2017/0078583 A1* | 3/2017 | Haggerty ............ A61B 1/00071 |
| 2017/0181802 A1 | 6/2017 | Sachs et al. |
| 2017/0188795 A1* | 7/2017 | Ouyang ............. G02B 23/2484 |
| 2017/0273716 A1* | 9/2017 | Garofalo ............ A61B 17/3439 |
| 2017/0319174 A1* | 11/2017 | Hill ....................... A61B 8/4245 |
| 2018/0221102 A1 | 8/2018 | Wang et al. |

FOREIGN PATENT DOCUMENTS

| | | |
|---|---|---|
| WO | WO-2010/067267 A1 | 6/2010 |
| WO | WO-2010/126127 A1 | 11/2010 |
| WO | WO-2011/040769 A2 | 4/2011 |
| WO | WO-2011/060046 A2 | 5/2011 |
| WO | WO-2011/135503 A1 | 11/2011 |
| WO | WO-2011/137336 A1 | 11/2011 |
| WO | WO-2012/044334 A2 | 4/2012 |
| WO | WO-2012/060586 A2 | 5/2012 |
| WO | WO-2013/180773 A1 | 12/2013 |
| WO | WO-2014/011969 A1 | 1/2014 |
| WO | WO-2014/073121 A1 | 5/2014 |
| WO | WO-2015/063524 A1 | 5/2015 |
| WO | WO-2015/115887 A1 | 8/2015 |
| WO | WO-2015/171614 A1 | 11/2015 |
| WO | WO-2016/083189 A1 | 6/2016 |

OTHER PUBLICATIONS

Kim, K. Y., et al., "A Novel Surgical Manipulator with Workspace-Conversion Ability for Telesurgery," IEEE/ASME Transactions on Mechatronics, vol. 18, No. 1, pp. 200-211 (Feb. 2013).

Song, et al., "The Development of Human-Arm Like Manipulator for Laparoscopic Surgery With Force Sensing," 2006 IEEE International Conference on Industrial Technology, Mumbai, 2006, pp. 1258-1262, 5 pages.

Oppenheimer, et al., "Immersive Surgical Robotic Interfaces," Human Interface Technology Lab, University of Washington, Paper presented at *Medicine Meets Virtual Reality* (MMVR 1999), Jan. 20-23, 1999, San Francisco, California, 7 pages.

Ali Talasaz, "Haptics-Enabled Teleoperation for Robotics-Assisted Minimally Invasive Surgery," May 2012, Electronic Thesis and Dissertation Repository, Paper 498, 175 pages.

International Search Report and Written Opinion issued by the U.S. Patent and Trademark Office as International Searching Authority for International Application No. PCT/US18/50922 dated Dec. 7, 2018 (10 pages).

European Application No. 18856312 Search Report dated May 20, 2021.

PCT/US2018/050922 International Preliminary Report on Patentability dated Mar. 17, 2020.

Roppenecker, Entwicklung und Validierung eines generativ gefertigten Snake-Like Manipulators für die minimal-invasive Chirurgie, Aug. 8, 2017, XP055559501.

Japanese Office Action for Application No. 2020-515936, dated Aug. 24, 2022, 9 pages.

\* cited by examiner

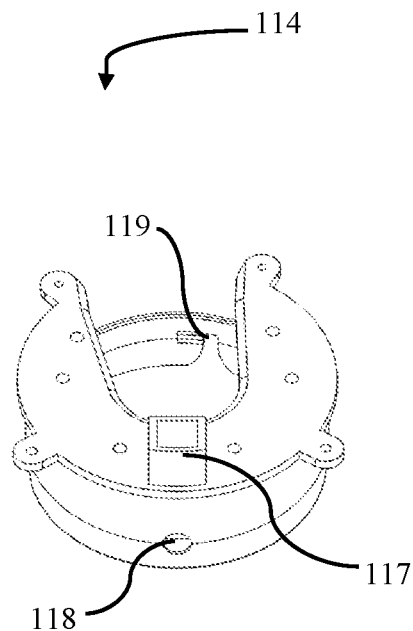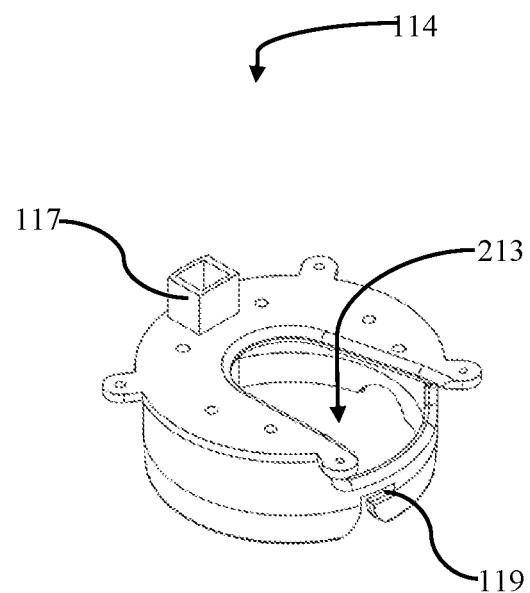
FIG. 5A　　　　　　　　　　　FIG. 5B
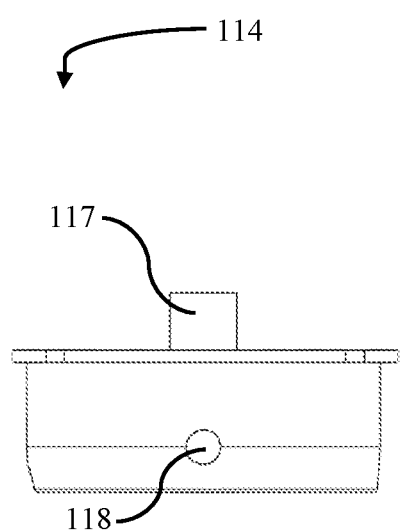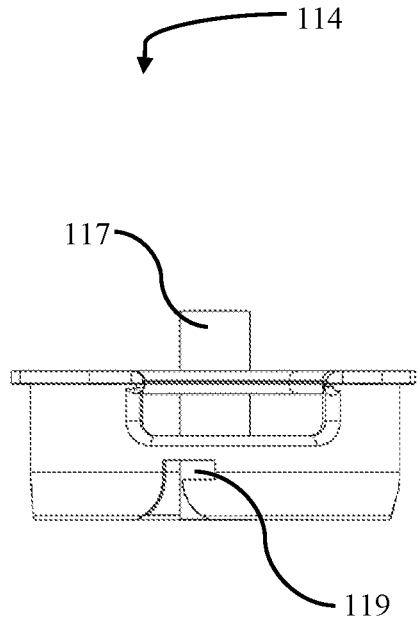
FIG. 5C　　　　　　　　　　　FIG. 5D

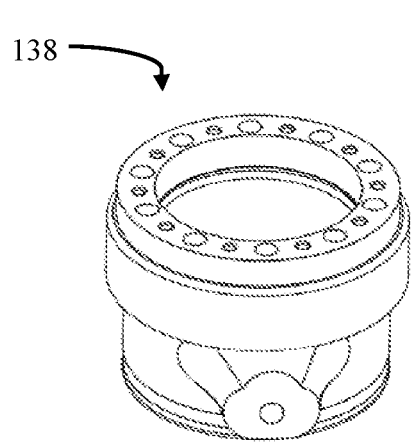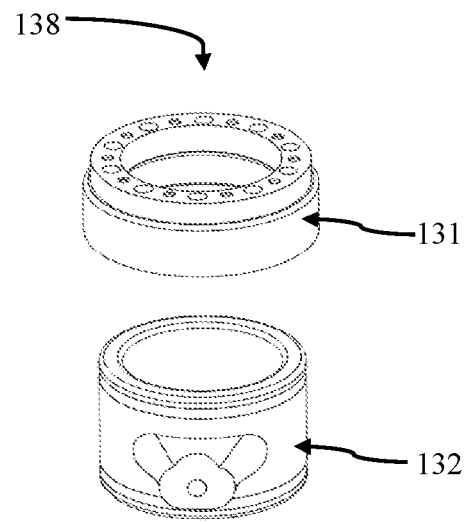
FIG. 15A              FIG. 15B
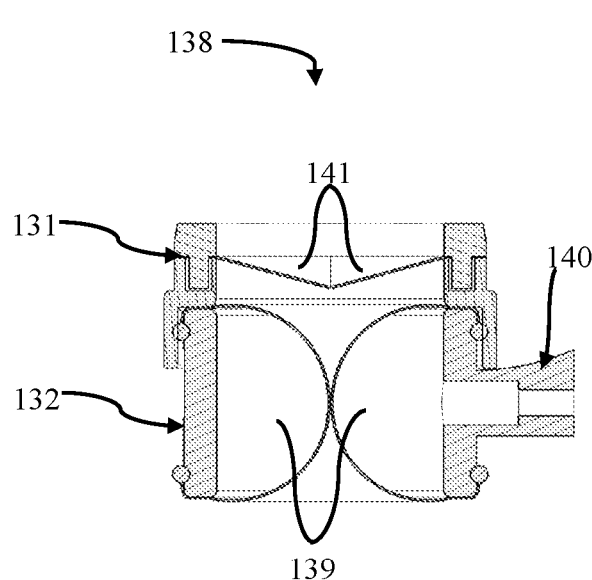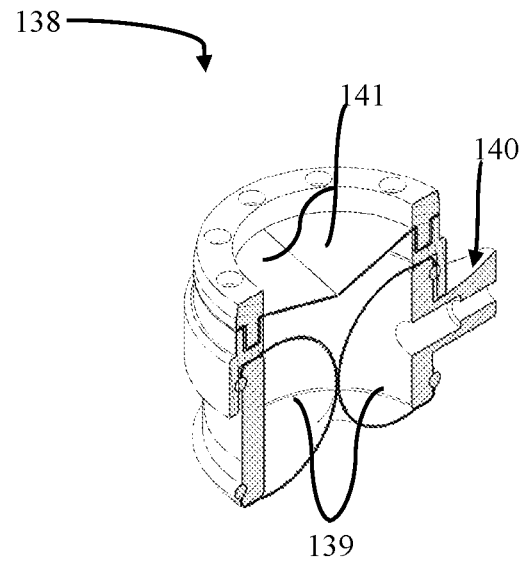
FIG. 16A              FIG. 16B

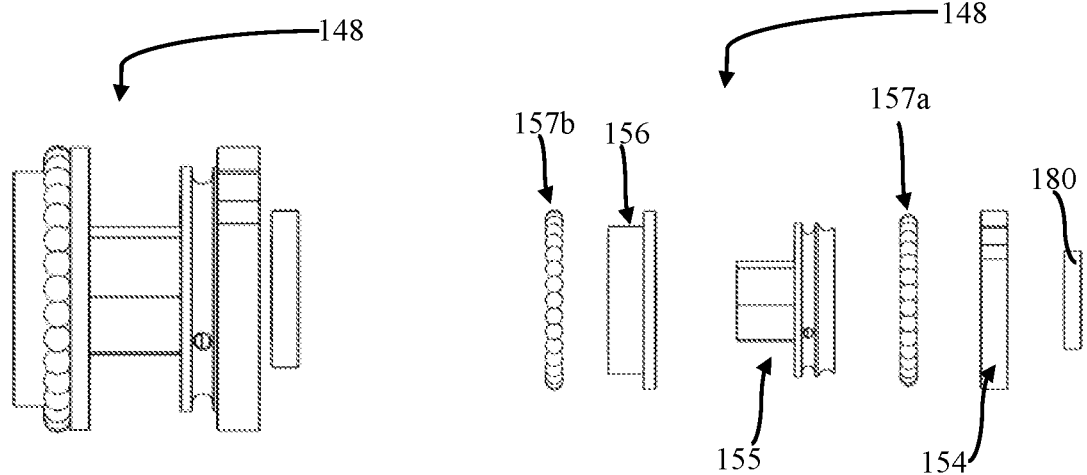
FIG. 22A
FIG. 22B
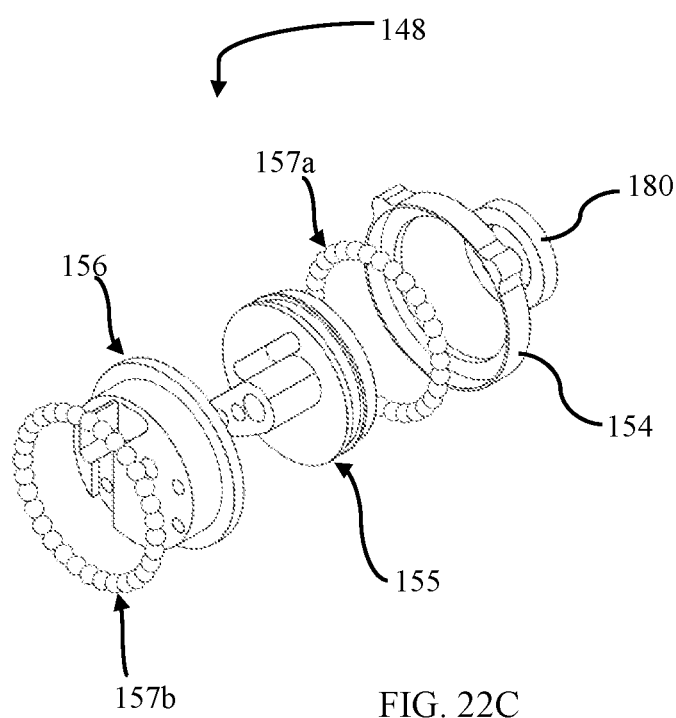
FIG. 22C

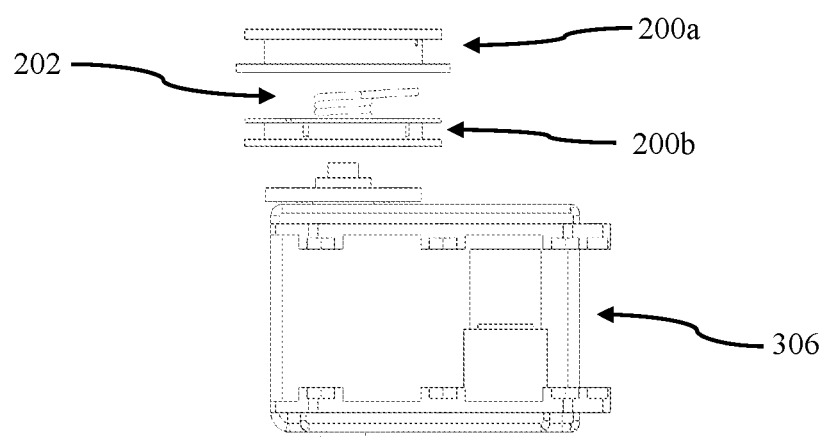
FIG. 31A
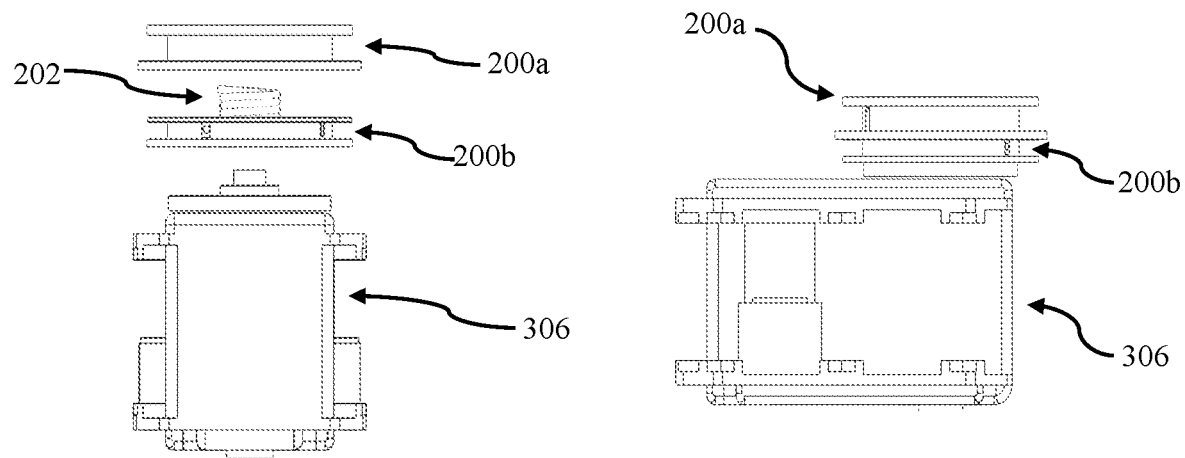
FIG. 31B
FIG. 31C

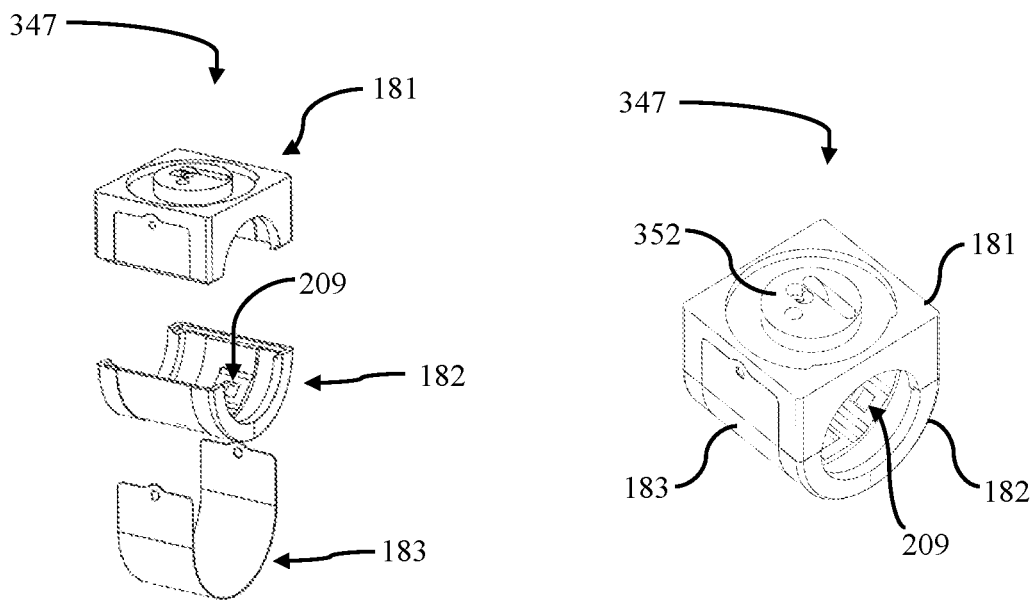
FIG. 35A
FIG. 35B
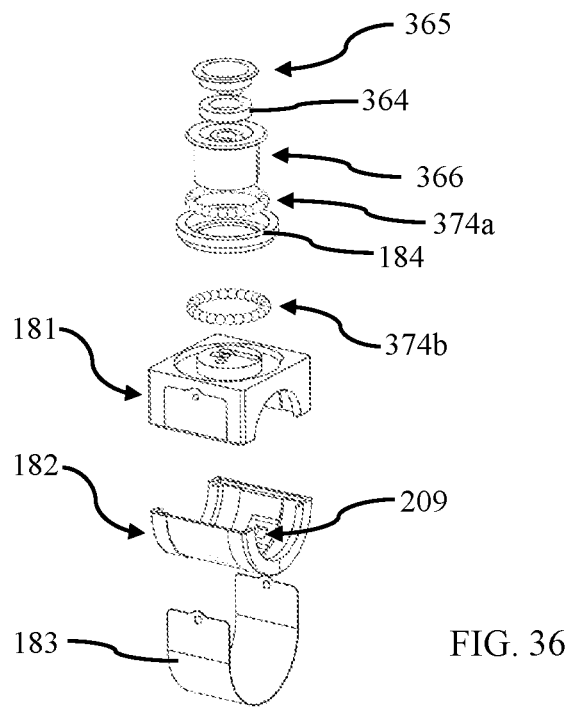
FIG. 36

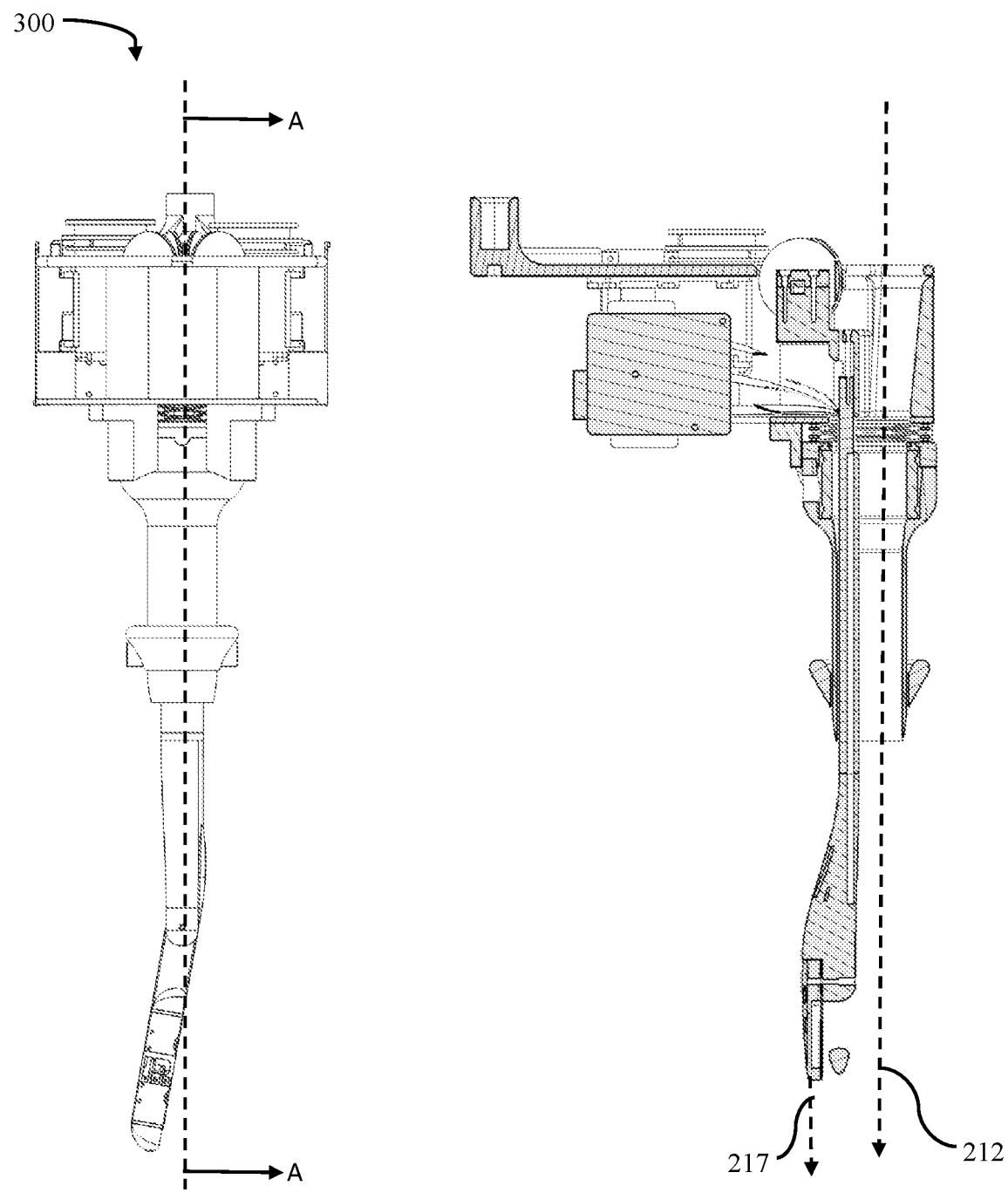
FIG. 45　　　　　　　　　　　　　　　　SECTION A-A

VIRTUAL REALITY SURGICAL CAMERA SYSTEM

CROSS-REFERENCES TO RELATED APPLICATIONS

This application claims the benefit under 35 U.S.C. § 119(e) to U.S. Provisional Patent Application No. 62/558,583, entitled Virtual Reality Surgical Camera System filed on Sep. 14, 2017, which is hereby incorporated by reference in its entirety.

BACKGROUND

Field of Invention

This application generally relates to minimally invasive surgery, minimally invasive surgical cameras and virtual reality minimally invasive surgical systems.

Description of Related Art

The field of minimally invasive surgery has undergone tremendous development and growth since its inception in the 1900's, with said developments and growth yielding improved results for patients. One of the major developments in the minimally invasive surgery field has been the implementation of surgical robotic devices. The implementation and utilization of surgical robotic devices in the minimally invasive surgery field has led to an increase in the number and types of surgeries that can be performed using said devices. The increase has led to many improvements for patients, including shorter recovery times, improved outcomes and quicker operation times. The increase in the utilization of surgical robotic devices has created an influx in the number of devices capable of performing a myriad of functions and operations, and being controlled and operated via various techniques.

During minimally invasive surgery, typically an endoscopic camera is used to provide the surgeon with imagery of the operation site and surgical cavity to allow the surgeon to manipulate robotic tools and also allow others to view the procedure while it is being performed. Routinely, during minimally invasive surgeries, the surgeon is concentrated on tasks of manipulating tissue and retracting organs. In order to accomplish these tasks, the surgeon manually maneuvers the endoscopic camera to a desired location and position in order to obtain a view adequate for performing a procedure. Typically, endoscopic cameras give a limited and narrow field of view, which results in the surgeon having to manually move the endoscopic camera back and forth or to a different location in order for the surgeon to view tools or tissue outside of his or her field of view. Requiring the surgeon to manually move the endoscopic camera requires the surgeon to switch his or her focus from performing the operation and concentrate on obtaining an adequate view, which results in longer operation times and longer recovery times for patients.

Typically, throughout minimally invasive surgeries multiple views and angles of the operation field are needed for a surgeon to perform the operation. Generally, the endoscope may be manually moved marginally left, right, back and/or forward to obtain a larger view or a different view during the operation, and then moved back it its original position and orientation so as to allow the surgeon to view the tissue and/or organ at a desired magnification. Physically manipulating the endoscopic camera requires the surgeon to switch his or her focus to the view of the operation instead of performing the operation, which can lead to patients sustaining accidental incidents, as well as longer recovery times and longer operation times.

In order to eliminate the need to manually move endoscopic cameras to obtained multiple views of an operation site, as well as a larger field of view, some have utilized multiple endoscopic cameras, inserting each endoscopic camera through a different incision in the patients cavity. While this has allowed surgeons to obtain multiple and different views, it has come at a cost to the patient as multiple incisions must be made in order to insert multiple endoscopic cameras, increasing the risk of herniation, risk of infection, pain and general morbidity. Additionally, utilizing multiple endoscopic cameras decreases the surgeon's workspace and thus making it more difficult for the surgeon to perform the operation.

While using and manually maneuvering and manipulating an endoscopic camera(s) is a viable option in conventional minimally invasive surgeries, and existing robotic surgeries, it is unpractical and not an intuitive method for maneuvering and manipulating a camera during virtual reality surgeries. In virtual reality surgeries, the surgeon has the perception of being condensed inside a patient's body at a surgical site. In conjunction with three-dimensional visualization provided by virtual reality goggles, the surgeon views the operation and interacts with the robotic arms as if the robotic arms have taken the form of his or her own arms and hands. With virtual reality surgeries, the surgeon is engrossed in a natural and immersive virtual reality user interface. While the surgeon is immersed in the virtual reality user interface it would be cumbersome for the surgeon to manually maneuver and relocate an endoscopic camera to a desired location and position, as it would require the surgeon to disconnect and remove him/herself from the natural and immersive virtual reality user interface. Alternatively, if the surgeon was to manually manipulate the endoscopic camera, such manipulation would be disorienting for the surgeon, and thus could lead to increased operation time, as well as disrupt the surgeon's work flow. In order to allow a surgeon to remain immersed in the natural and immersive virtual reality user interface, a different technique of controlling a camera and obtaining multiple views of the operation field is necessary for virtual reality surgery.

With human-like robotic systems, having a successful system results from maintaining a natural and intuitive human-machine interface (HMI). As such, it is advantageous in a virtual reality surgery for a surgeon to be able to interact and control the camera while maintaining the functionality of a human-like robot.

BRIEF SUMMARY OF INVENTION

In one embodiment the invention includes a system comprising a console assembly comprising, a first actuator, and a first actuator pulley operably coupled to the first actuator, a trocar assembly operably coupled to the console assembly, the trocar assembly comprising, a trocar having an inner and an outer diameter, and a seal sub-assembly comprising at least one seal, the seal sub-assembly operably coupled to the trocar, a camera assembly operably coupled to the console assembly, the camera assembly comprising, a camera support tube having a distal end and a proximal end, a stereoscopic camera assembly operably coupled to the distal end of the camera support tube, the stereoscopic camera assembly comprising, a main camera body defining a cavity, a pitch actuation assembly, a yaw actuation assembly, the pitch and yaw actuation assemblies providing at least two rotational degrees of freedom, a first camera module having a first optical axis, and a second camera module having a second optical axis, and at least one rotational positional sensor configured to detect rotation of the stereoscopic camera assembly about at least one of a pitch axis or a yaw axis, wherein the yaw axis is normal to a plane in which the camera support tube lies, and the pitch axis is perpendicular to the yaw axis. The seal sub-assembly of the system may also comprise a second seal. The trocar assembly of the system may also comprise a seal plug. The stereoscopic camera assembly of the system may also comprise a peripheral camera. The system, the first optical axis of the first camera module and the second optical axis of the second camera module have an inter-axial distance configured to provide stereo vision. The console assembly of the system may also comprise a plurality of actuators. The trocar assembly of the system may also comprise a trocar mating fixture defining a pass through having a pass through axis, wherein the pass through axis configured to permit access through the camera console assembly and through the trocar assembly.

The system may also comprise, a pitch cable operably coupling the pitch actuation assembly to the first actuator pulley so that actuation of the first actuator rotates the stereoscopic camera assembly about the pitch axis. In the system comprising a pitch cable, the console assembly may also comprise, a second actuator and a second actuator pulley operably coupled to the second actuator. In the system comprising a console assembly with a second actuator, may also comprise a yaw cable operably coupling the second actuator to the second actuator pulley so that actuation of the second actuator rotates the stereoscopic camera assembly about the yaw axis. In the system comprising a yaw cable, the console assembly may also comprise a first redirecting pulley disposed along a path of the pitch cable between the first actuator pulley and the pitch actuation assembly, the first redirecting pulley being configured to redirect the path of the pitch cable from the first actuator pulley to a first cable lumen defined by the camera support tube. In the system comprising a yaw cable, the console assembly may also comprise a redirecting pulley disposed along a path of the yaw cable between the second actuator pulley and the yaw actuation assembly, the redirecting pulley being configured to redirect the path of the yaw cable from the second actuator pulley to a second cable lumen defined by the camera support tube.

In the system comprising a console assembly with a first redirecting pulley, may also comprise a second redirecting pulley disposed along a path of the yaw cable between the second actuator pulley and the yaw actuation assembly, the second redirecting pulley being configured to redirect the path of the yaw cable from the second actuator pulley to a second cable lumen defined by the camera support tube.

In other embodiments, the stereoscopic camera assembly of the system has an insertion configuration and a deployed configuration, and wherein, in the insertion configuration, the first optical axis of the first camera module and the second optical axis of the second camera modules are orientated perpendicular to the camera support tube. In the system with a stereoscopic camera assembly with an insertion configuration and a deployed configuration, the first camera module comprising a first camera module body having a first outer edge, the second camera module comprising a second camera module body having a second outer edge, and wherein a maximum distance from the first outer edge of the first camera module body to the second outer edge of the second camera module body is greater than a maximum width of a cross-section of the stereoscopic camera assembly taken perpendicular to an axis of the camera support tube.

In another aspect the invention includes a camera assembly comprising a camera support tube having a distal end and a proximal end, a stereoscopic camera assembly operably coupled to the distal end of the camera support tube, the stereoscopic camera assembly comprising, a main camera body operably coupled to the distal end of the camera support tube, wherein the main camera body defines an electrical component cavity, a first camera module having a first optical axis, a second camera module having a second optical axis, and an actuation system comprising a pitch actuation assembly and a yaw actuation assembly, the actuation system providing at least two rotational degrees of freedom; and at least one rotational positional sensor configured to detect rotation of the stereoscopic camera assembly about at least one of a pitch axis or a yaw axis, wherein the yaw axis is normal to a plane in which the camera support tube lies, and the pitch axis is perpendicular to the yaw axis. In one embodiment, the actuation system of the camera assembly is cable driven. In another embodiment, the actuation system of the camera assembly is motor driven. In other embodiments, the yaw actuation assembly of the camera assembly is configured to actuate the stereoscopic camera assembly about the yaw axis. In yet another embodiment, the pitch actuation assembly of the camera assembly is configured to actuate the stereoscopic camera about the pitch axis. In other embodiments, the pitch actuation assembly of the camera assembly is configured to actuate the stereoscopic camera assembly about the pitch axis independent of the yaw actuation assembly. The stereoscopic camera of the camera assembly may also comprise a lighting source operably coupled to a power supply.

In another embodiment, the stereoscopic camera assembly of the camera assembly may also comprise a first peripheral camera. In the camera assembly comprising a first peripheral camera, the stereoscopic camera assembly may also comprise a second peripheral camera.

In yet another embodiment, the stereoscopic camera assembly of the camera assembly may also comprise an electrical communication component, wherein the electrical communication component is configured to transmit information captured by at least one of the first camera module, the second camera module, or the at least one rotational positional sensor. In the camera assembly comprising an electrical communication component, the electrical communication component may also comprise a flexible printed circuit boards (FPCB). In another embodiment, the camera assembly comprising an electrical communication component, the electrical communication component may also comprise a printed circuit boards (PCB).

In another embodiment of the camera assembly comprising an electrical communication component, the electrical communication component is physically configured to permit the stereoscopic camera assembly to be actuated in the at least two rotational degrees of freedom, and wherein the electrical communication component is configured to transmit the information captured by the at least one of the first camera module, the second camera module, or the at least one rotational positional sensor during actuation of the stereoscopic camera assembly in the at least two rotational degrees of freedom. In another embodiment of the camera assembly comprising the electrical communication component physically configured to permit the stereoscopic camera assembly to be actuated in the at least two degrees of freedom, the electrical communication component can be bent to a minimum allowable bend radius without being damaged or rendered unuseable. In the camera assembly comprising the electrical communication component physically configured to permit the stereoscopic camera assembly to be actuated in the at least two degrees of freedom, may also comprise an electrical communication retainer, the electrical communication component retainer preventing the electrical communication components from being damaged while the actuation system is in use.

In another embodiment the camera assembly comprising the electrical communication component physically configured to permit the stereoscopic camera assembly to be actuated in the at least two degrees of freedom, may also comprise a flex shield that provides a protective casing for the electrical communication components, the flex shield preventing the electrical communication components from coming into contact with other objects and/or components while the camera assembly is in use. In the camera assembly comprising a flex shield, the flex shield may also comprise side walls.

In yet another embodiment the camera assembly comprising the electrical communication component physically configured to permit the stereoscopic camera assembly to be actuated in the at least two degrees of freedom, the electrical communication components are situated in an electrical communication cavity defined by the main camera body. In the camera assembly with the electrical communication components situated in an electrical communication cavity, may also comprise a flex wrap guide and a constant-force spring, wherein the constant-force spring applies a radial force on the electrical communication component. In another embodiment the camera assembly with the electrical communication components situated in an electrical communication cavity, the main camera body may also define machined surface apertures.

In other embodiments of the camera assembly, the first optical axis of the first camera module and the second optical axis of the second camera module have an interaxial distance configured to provide stereo vision. In another embodiment, the stereoscopic camera assembly of the camera assembly, has an insertion configuration and a deployed configuration, wherein in the insertion configuration the first optical axis of the first camera module and the second optical axis of the second camera modules are orientated perpendicular to the camera support tube. In the camera assembly with the stereoscopic camera assembly having an insertion configuration and deployed configuration, the first camera module comprising a first camera body having a first outer edge, the second camera module comprising a second camera module body having a second outer edge, and wherein the maximum distance from the first outer edge of the first camera module body to the second outer edge of the second camera module body is greater than the maximum width of a cross-section of the stereoscopic camera assembly taken perpendicular to an axis of the camera support tube.

BRIEF DESCRIPTION OF FIGURES

Note that numbered items remain consistent across all figures. Items numbered with the same number are either the same item, or identical copies of the item. Items numbered with different numbers are either parts of different design or are occasionally identical parts serving different purposes.

FIG. 5A is a front isometric view of a trocar mating fixture according to one embodiment.

FIG. 5B is a diagonal isometric view of a trocar mating fixture according to one embodiment.

FIG. 5C is a front profile view of a trocar mating fixture according to one embodiment.

FIG. 5D is a back profile view of a trocar mating fixture according to one embodiment.

FIG. 15A is an isometric view of a seal sub-assembly according to one embodiment.

FIG. 15B is an exploded isometric view of a seal sub-assembly according to one embodiment.

FIG. 16A is a cross-section profile view of a seal sub-assembly according to one embodiment.

FIG. 16B is an isometric cross-section view of a seal sub-assembly according to one embodiment.

FIG. 22A is a profile view of a pitch actuation assembly according to one embodiment.

FIG. 22B is an exploded profile view of a pitch actuation assembly according to one embodiment.

FIG. 22C is an exploded isometric view of a pitch actuation assembly according to one embodiment.

FIG. 31A is an exploded profile view of a counter-rotating pulley system according to one embodiment.

FIG. 31B is an exploded back profile view of a counter-rotating pulley system according to one embodiment.

FIG. 31C is a profile view of a counter-rotating pulley system according to one embodiment.

FIG. 35A is an exploded isometric view of a main camera body mount according to one embodiment.

FIG. 35B is an isometric view of a main camera body mount according to one embodiment.

FIG. 36 is an exploded isometric view of the connection between a main camera body mount and a yaw actuation assembly, according to one embodiment.

FIG. 45 is a cross-section of a robotic camera system highlighting a pass through axis, according to one embodiment.

DETAILED DESCRIPTION

Figure 1A:
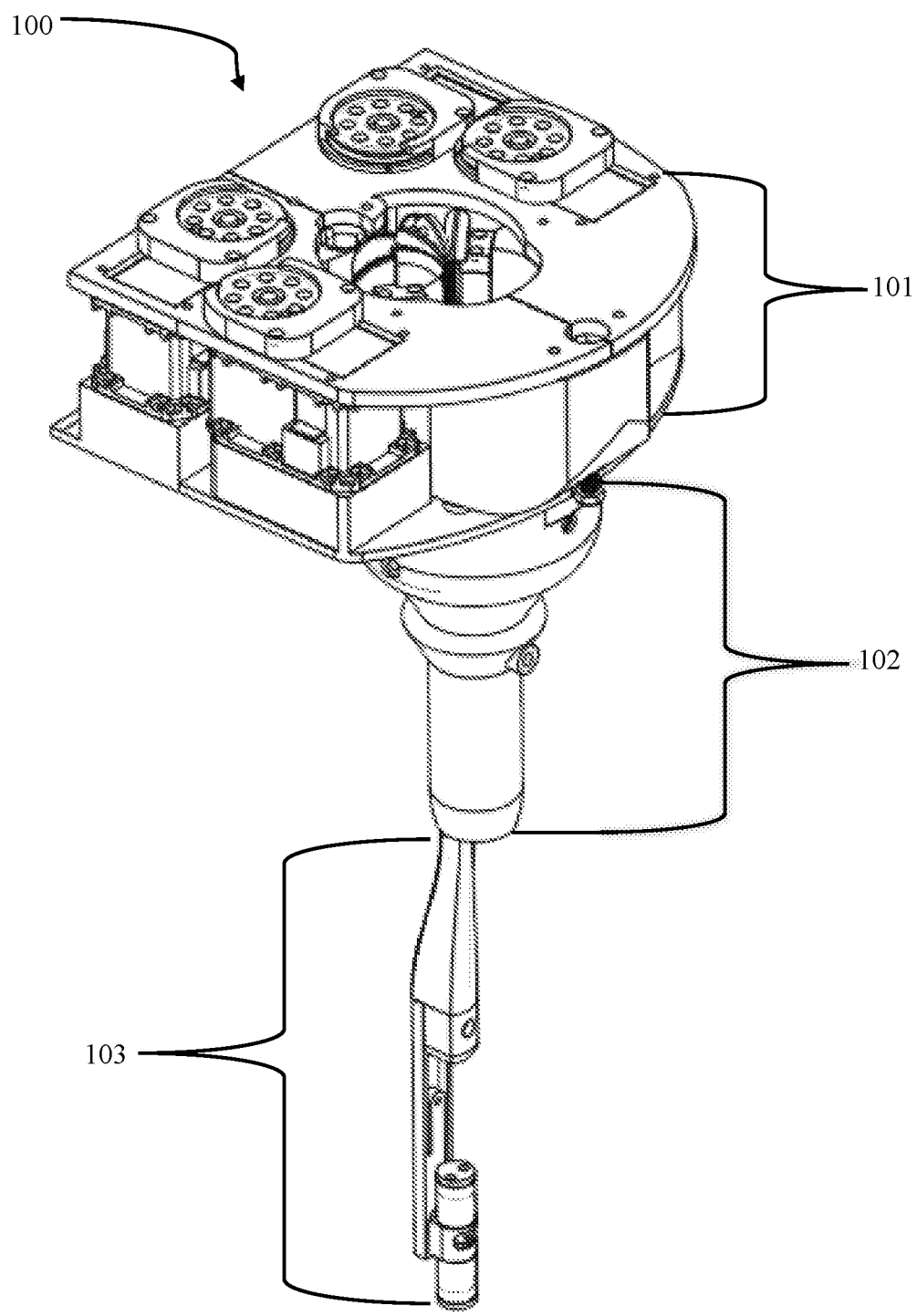
FIG. 1A is a front isometric view of one embodiment of a Robotic camera system.

While the present system is designed for use by a surgeon within the abdominal cavity, many alternative uses of the system are possible. For example, a user might be a physician's assistant, nurse, surgical aid, or any other surgical personnel. Additionally, the device could be disposed within any part of a patient's body, and future embodiments could be designed to be much smaller so as to allow for use within smaller areas of a patient's body. Both smaller and larger devices can be fabricated for uses in areas such as the paranasal sinuses, colon, stomach, or any other areas within the human body including but not limited to, the abdomen, cranium and cervicis. Micro-fabrication utilizing MEMS or other means could allow for a device to be positionable within immensely small areas such as human blood vessels.

In some embodiments, the device may be used for non-surgical or non-medical tasks such as bomb diffusion, military reconnaissance, inspectional services, or any other task which requires obtaining multiple camera views without manual manipulation of the camera. In addition, some embodiments may be used for educational purposes, such as for training personnel. Some embodiments of the device could be fabricated to be human-sized or even larger-than-life, allowing humans to obtain visuals from areas unable to be reached or viewed by a human. Obviously, in such embodiments, the user many not necessarily be a surgeon.

Overview

In particular embodiments, the surgical apparatus system disclosed herein is designed to be incorporated and utilized with the Virtual Reality Surgical Device disclosed in International Patent Application No. PCT/US2015/029247 (published as International Patent Publication No. WO2015171614A1), incorporated by reference herein in its entirety. Notwithstanding the above-sentence, in some embodiments the surgical apparatus system disclosed herein can be implemented and utilized by other existing and future robotic surgery systems and/or devices.

The purpose of the system is to allow a surgeon who is performing MIS surgery, to be obtain multiple views and angles of a surgical site without having to manually manipulate and/or move an endoscopic camera. The system allows a surgeon to control the manipulation of a camera based off the movement of the surgeon's head movement, such that that surgeon can obtain a desired view by intuitively moving his or her head in the direction he or she would like to view. When the system is in use the surgeon is able to view the operation site, in such a way that he or she has the perception of being inside the patient's body, and by simply looking around the surgeon is able to view the entire operation field and obtain a desired view. This advantageously allows the surgeon to efficiently obtain a desired view, enabling him or her to maintain focus during a procedure, resulting in quicker operation time and faster recovery times for the patient.

Unless otherwise stated, the term "distal" as used herein means relatively further from a reference point, while "proximal" means relatively closer to a reference point. In general, the reference point will be the incision site on the patient's body for which the system is being used.

Figure 1B:
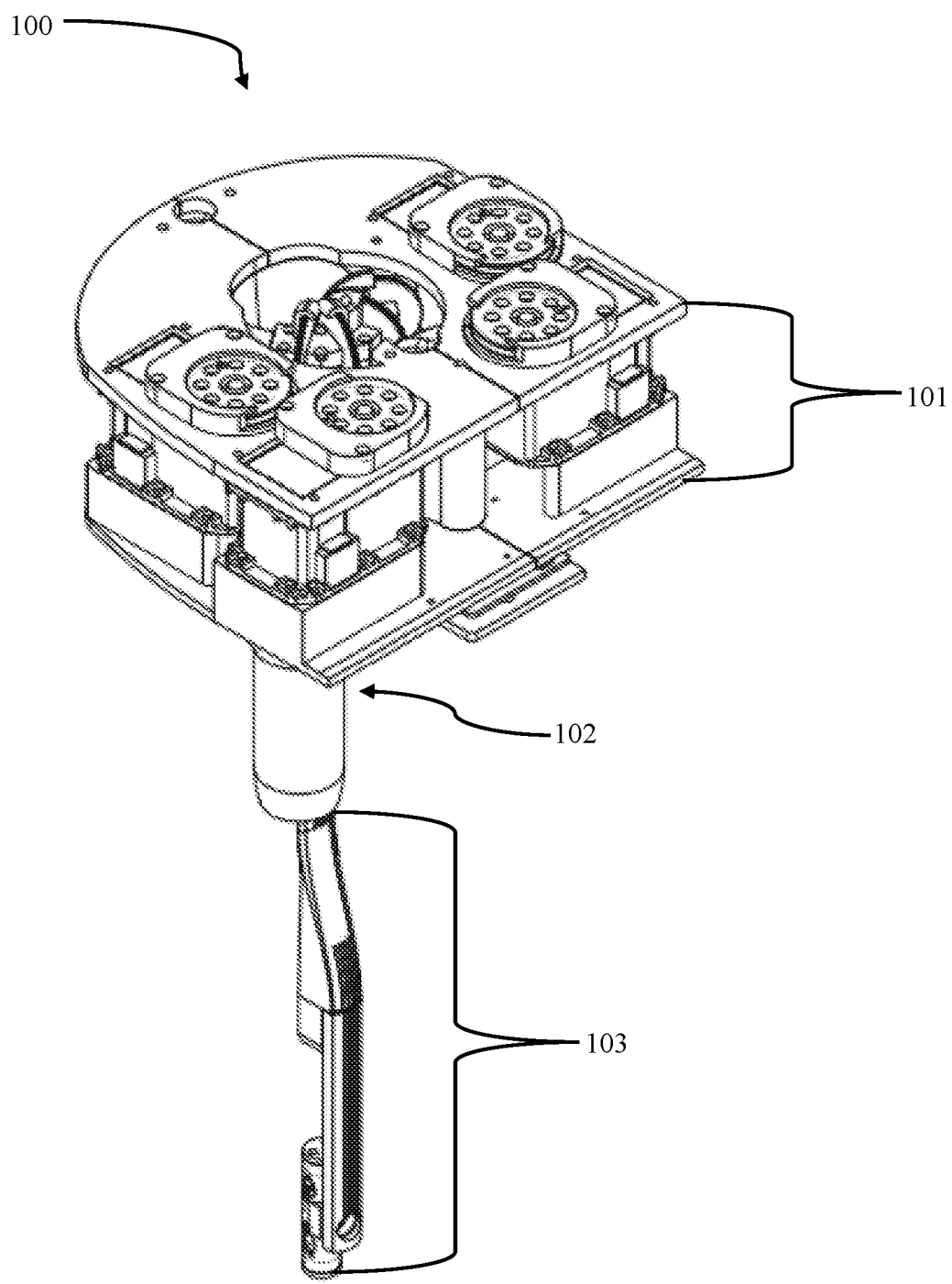
FIG. 1B is a back isometric view of one embodiment of a Robotic camera system.

FIG. 1A shows a front isometric view of one embodiment of the robotic camera system 100. FIG. 1B gives an illustration of one embodiment of the robotic camera system 100. As illustrated in the embodiment shown in FIG. 1A-1B the robotic camera system 100 consists of a camera console assembly 101, a trocar assembly 102 and a robotic camera assembly 103. Each of the aforementioned assemblies are comprised of sub-assemblies, as well as additional components, which combine to create the robotic camera system 100.

Camera Console Assembly

Figure 2A:
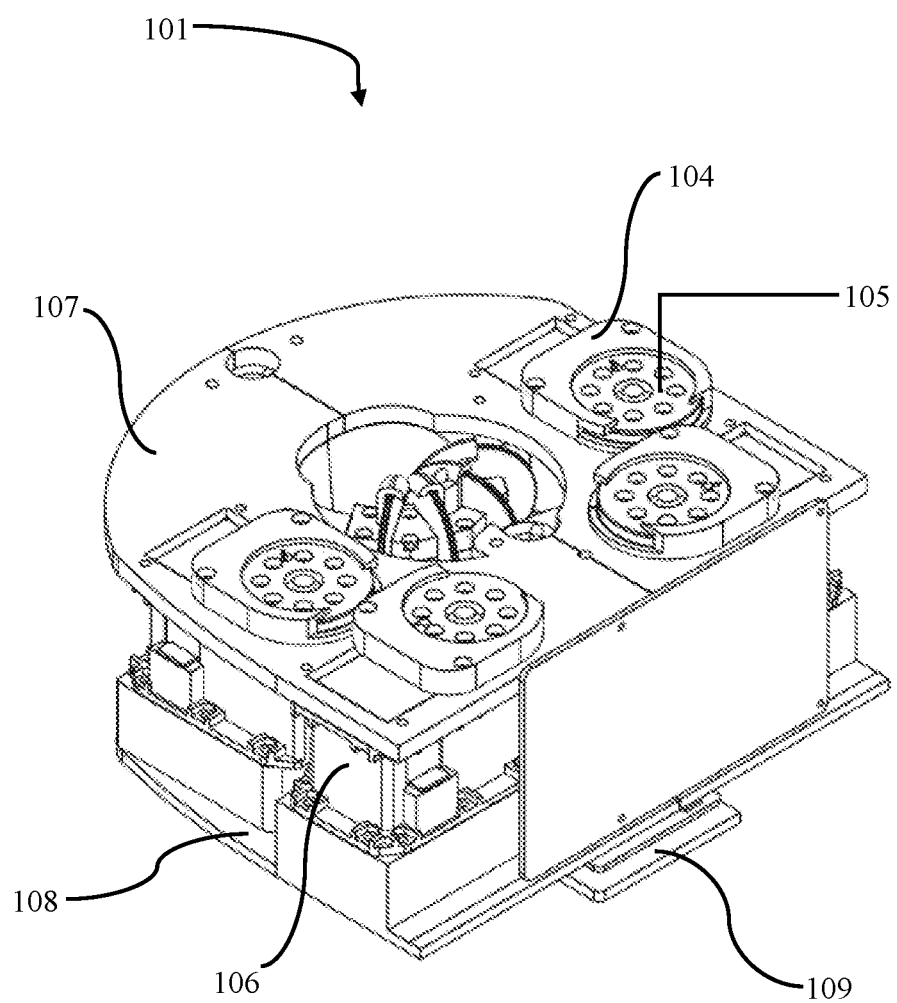
FIG. 2A is a back isometric view of a camera console assembly according to one embodiment.
Figure 2B:
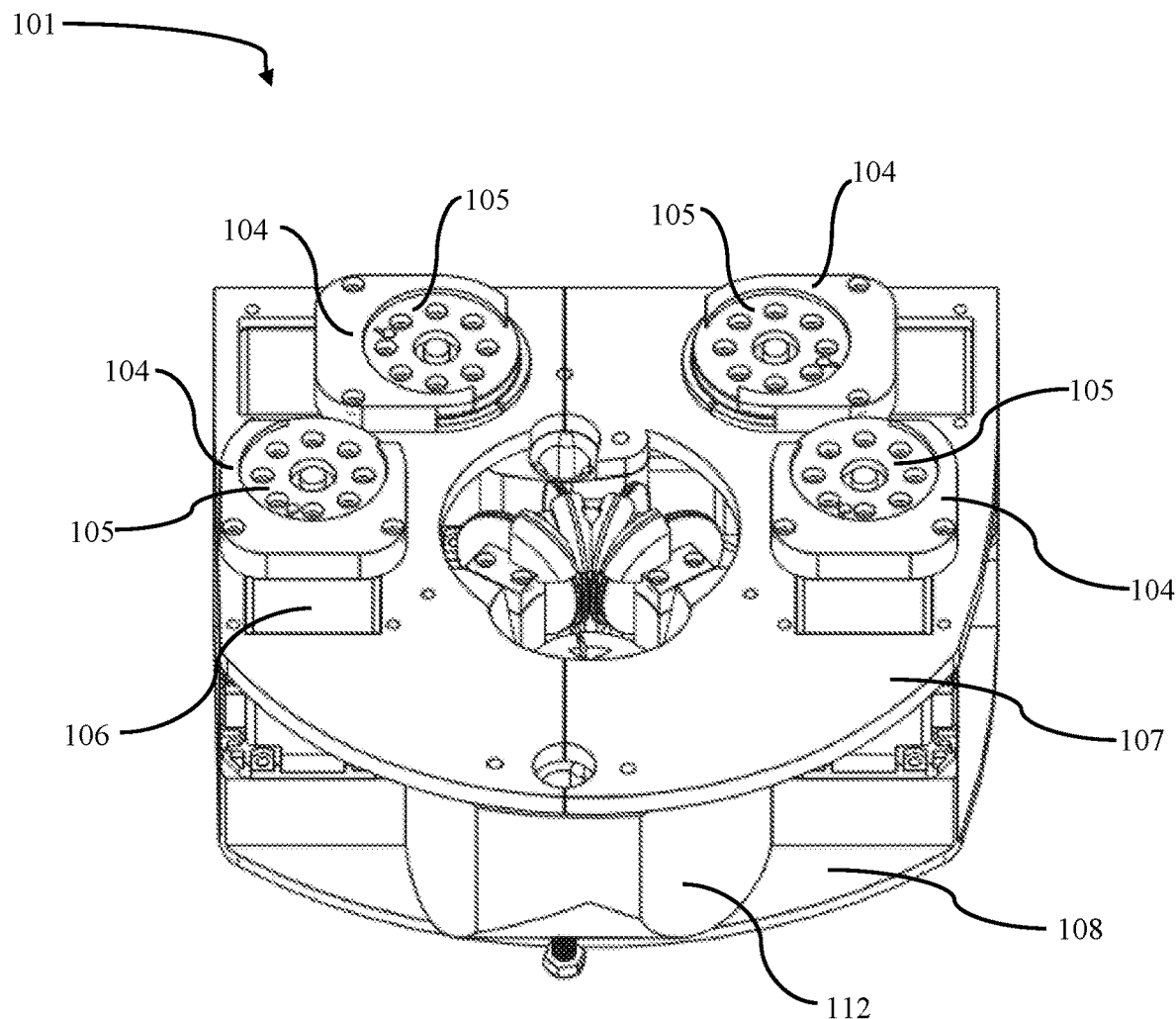
FIG. 2B is a front isometric view of a camera console assembly according to one embodiment.
Figure 2C:
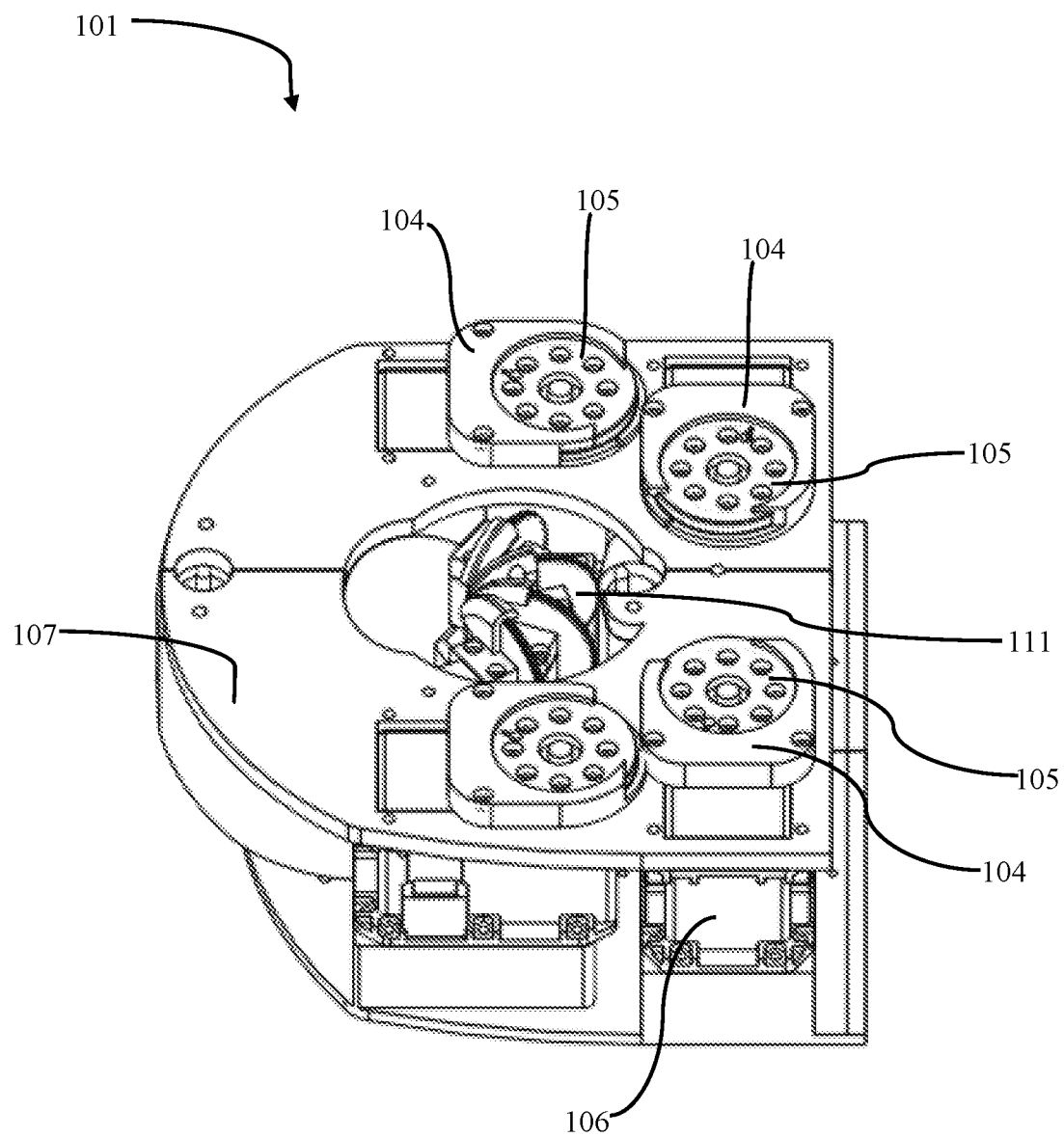
FIG. 2C is a side isometric view of a camera console assembly according to one embodiment.

As illustrated in FIG. 1A and FIG. 1B, at the proximal portion of the robotic camera system 100, is the camera console assembly 101. FIG. 2A-FIG. 2C show multiple isometric views of an illustrative embodiment of the camera console assembly 101. The camera console assembly 101 is an essential part to the overall robotic camera system 100, as it functions as a housing for actuators 106 of the system. In addition, the camera console assembly provides key mating and attachment functions for the trocar assembly and camera assembly, as well as other devices and components in various embodiments. Furthermore, the camera console assembly provides constraint and stability to the overall system, by preventing parts of the system from moving and detaching from other components. As illustrated in the embodiments shown in FIG. 2A-FIG. 2C, the camera console assembly 101 contains numerous components which combine together to create the assembly.

Figure 3:
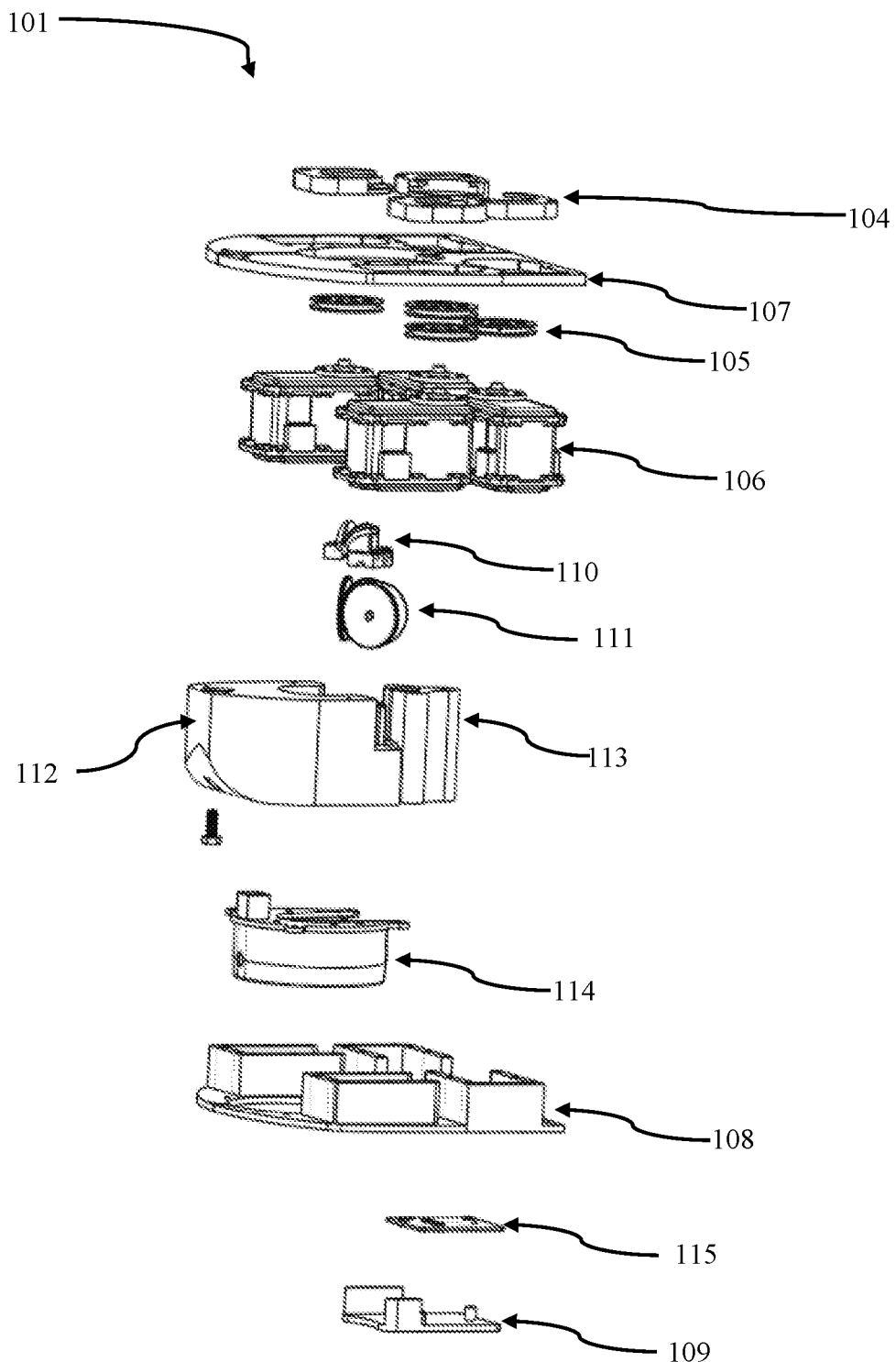
FIG. 3 is an exploded side isometric view of a camera console assembly according to one embodiment.

FIG. 3 shows an exploded view of one embodiment of the camera console assembly 101. In one embodiment, located at the distal end of the camera console assembly 101 is a camera console base 108. The camera console base 108, functions as a support for the actuators 106 of the system. In addition, the camera console base 108 also provides a mounting point for the robotic camera assembly 103 and the trocar assembly 102.

Figure 4A:
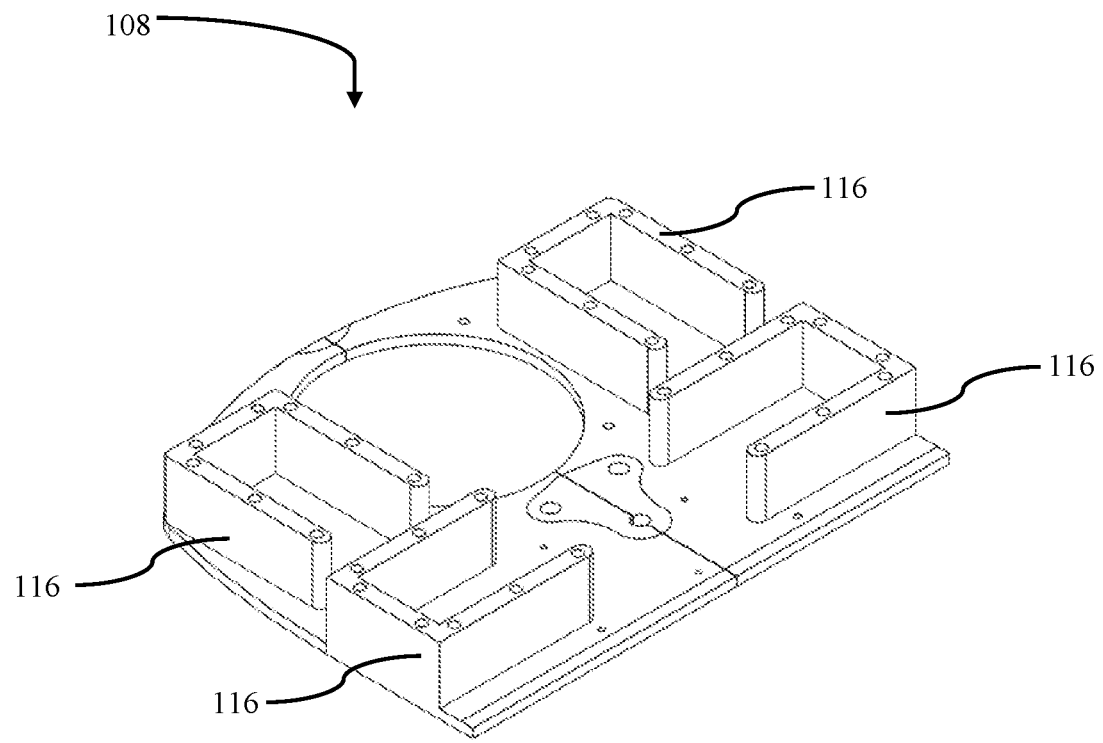
FIG. 4A is an isometric view of a camera console base according to one embodiment.
Figure 4B:
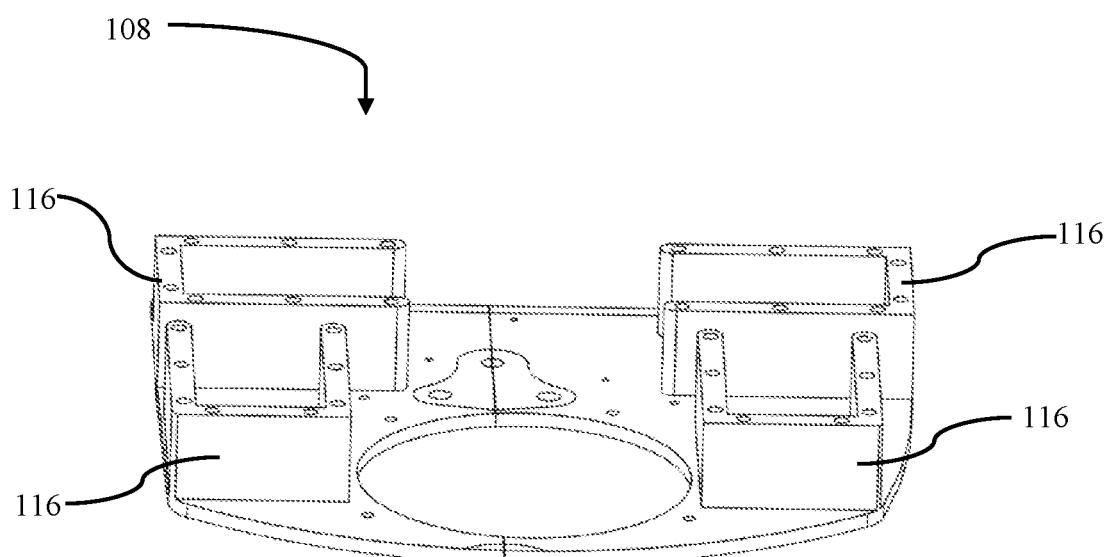
FIG. 4B is a front isometric view of a camera console base according to one embodiment.

FIG. 4A and FIG. 4B show multiple isometric views of an illustrative embodiment of the camera console base 108. In one embodiment, the camera console base 108 is configured as a plate that functions as a support for the camera console assembly 101, as well as a mounting point for the trocar assembly 102. In some embodiments, the camera console base 108 is fabricated as two halves that affix to one another via snap-fit connections. In other embodiments, the snap-fit connection is substituted for a pin-hole connection, while in further embodiments other connection types and/or methods are utilized, such as adhesive connection, welded connections, magnetic connection, and/or any other method or combination of methods known in the art. In alternative embodiments, the camera console base 108 is fabricated as one rigid piece. In some embodiments, the camera console base 108 is constructed out of stainless steel, while in alternative embodiments the plate is constructed out of plastics, ceramics and/or other material types known in the art, that are capable of supporting the camera console assembly 101.

As shown in the illustrative embodiment in FIG. 4A and FIG. 4B, the camera console base 108 contains a plurality of actuator mounts 116, which are affixed to the camera console base 108. In alternative embodiments, only one actuator mount 116 is affixed to the camera console base 108, while further embodiments could have anywhere from two to five actuator mounts 116, or more mounts may be affixed to the camera console base 108. In further embodiments, the camera console assembly is eliminated, and actuators are housed on an external support or device.

In one embodiment, the actuator mounts 116 are affixed to the camera console base 108 by a screw connection. In other embodiments, the actuator mounts 116 are affixed to the camera console base 108 via pin connections, while in further embodiments other connection types and/or methods known in the art are utilized such as adhesive connections, snap-fit connections, and/or welded connections. Alternatively, in other embodiments, the actuator mounts 116 and the camera console base 108 are fabricated as one rigid piece.

The actuator mounts 116, are configured to secure the actuators 106 (FIGS. 2A-2C) of the system in place, such that the actuators 106 stay confined in space during actuation of the system. The actuator mounts 116 affix the actuators 106 to the camera console base 108, via screw connections, in one embodiment. In alternative embodiments, different types of connection methods known in the art are utilized to couple the actuators 106 to the actuator mounts 116, such as snap-fit connections, adhesive connections and/or another method or combination of method capable of securing actuators. In one embodiment, the actuator mounts 116 are constructed as three (3) walls, that encompass the actuator 106, such that said actuator is constrained in place, thus preventing any movement of the actuator 106 during use. In alternative embodiments, the actuator mounts 116 are configured as two walls, with one wall being situated on either side of the actuator 106, such that said actuator is sandwiched between the two walls. In further embodiments, the actuator mounts 116 may be eliminated with the actuators 106 coupling directly to the camera console base 108. The actuator mounts 116 can be situated on the camera console base 108 in any location and configuration that allows cables to be routed from the robotic camera assembly 103 through the trocar assembly 102 to the actuators 106, such that the cables do not interfere and/or impede the actuation of the robotic camera assembly 103.

Figure 6:
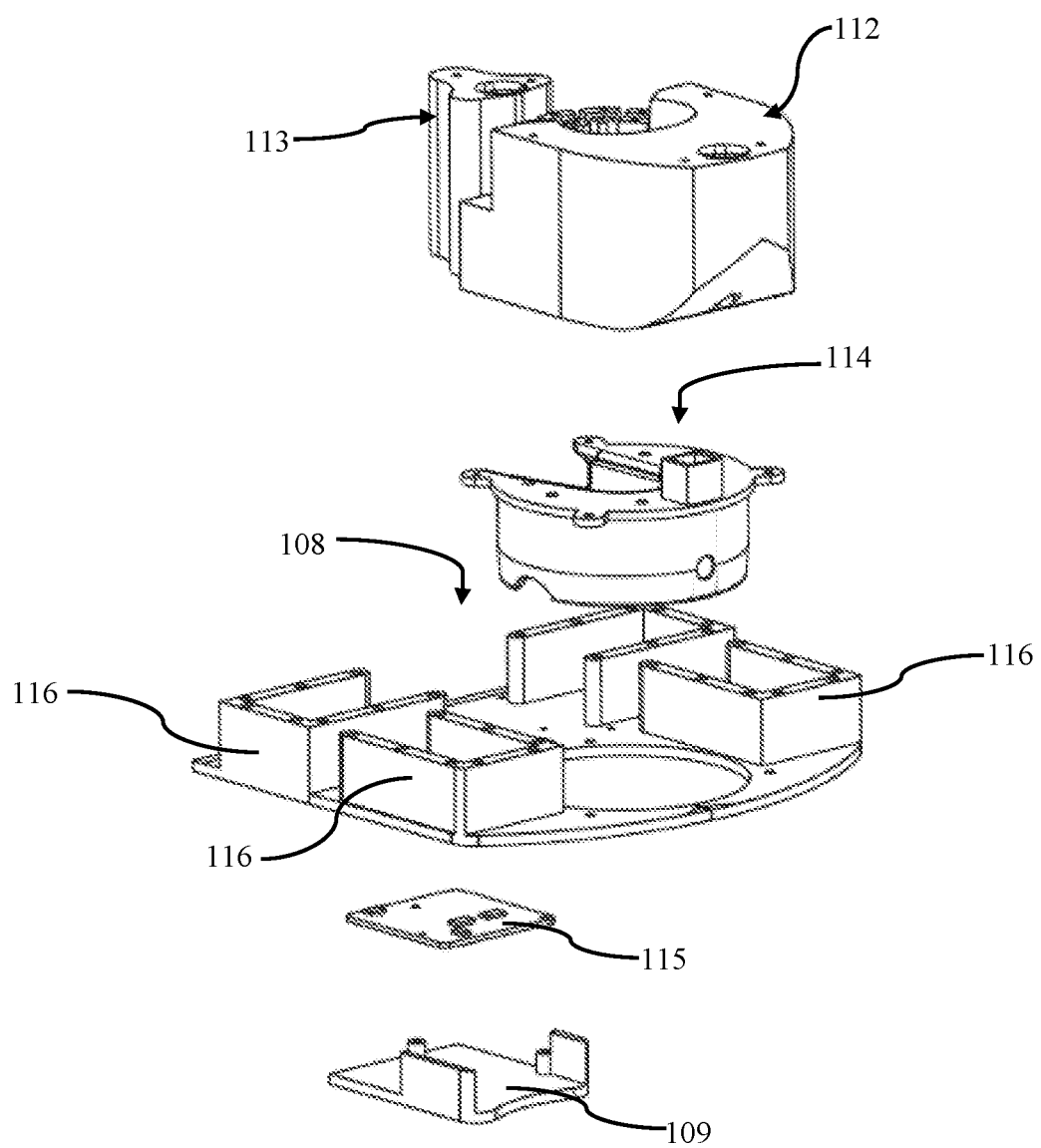
FIG. 6 is an isometric exploded view of some components which may couple to a camera console base according to one embodiment.

FIG. 6 shows an exploded view of one embodiment of the camera console base 108, illustrating some of the mating components that couple to the camera console base 108. As illustrated in the embodiment shown in FIG. 6, the camera console base 108, contains an aperture for which a trocar mating fixture 114 sits in. In one embodiment, the trocar mating fixture 114 has a distal end that protrudes from the aperture, and a proximal end which affixes to the camera console base 108.

FIG. 5A-FIG. 5D shows multiple views of an illustrative embodiment of the trocar mating fixture 114. In one embodiment, the proximal portion of the trocar mating fixture 114 is outfitted with a plurality of attachment rings. The attachment rings, are used to mate and attach the trocar mating fixture 114 to the camera console base 108. In one embodiment, the attachment rings affix to the camera console base 108, via screw connections, with the attachment rings configured to sit on top the camera console base 108, with the screw entering through a hole in the attachment rings and screwing into a hole on the camera console base 108. In other embodiments, the trocar coupling fixture 114 affixes to the camera console base 108 via adhesive connections, while in alternative embodiments other connection methods and/or combinations of methods known in the art are utilized, such as welded connections. In addition, in further embodiments, the trocar coupling fixture 114 and the camera console base 108 are fabricated as one rigid piece.

In some embodiments, where the camera console base 108 is constructed as two halves, the trocar mating fixture 114 is used to mate the two halves of the camera console base. In this embodiment, one side of the proximal end of the trocar mating fixture 114, affixes to one of halve of the camera console base, while the other side of the proximal end of the trocar mating fixture 114, affixes to the other halve of the camera console base, thus mating the two halves of the camera console base 108.

As mentioned above, in one embodiment, the trocar mating fixture 114 contains a distal end which protrudes from the bottom of the camera console base 108, with the proximal end of the trocar mating fixture 114 resting on the camera console base 108. In one embodiment, the trocar mating fixture 114 is outfitted with a connection housing 117 (FIG. 5A-5D). In one embodiment, the connection housing 117 extends proximally and distally from the proximal end of the trocar mating fixture 114. In one embodiment, the connection housing 117 is configured as square column with a hollow center, to allow a connection component to enter the housing and extend distally. In alternative embodiments, the connection housing 117 can take on a variety of shapes and configurations that allow a connection component to enter and extend distally, such as a cylinder, triangle and/or any other shape or configuration known in the art.

In various embodiments, a variety of connection components are utilized to mate the trocar mating fixture 114 and the trocar assembly 102. In one embodiment, a dog leg snap button connection is used to couple the trocar mating fixture 114 to the trocar assembly 102. In this embodiment, the trocar mating fixture 114 is outfitted with a connection aperture 118, which is situated on the front face of the trocar mating fixture 114. In this embodiment, the dog leg snap button (not pictured), sits within the connection housing 117 of the trocar mating fixture 114. The dog leg snap button is constrained in the connection housing 117, by friction with the back tab of the dog leg snap button pressed against the wall of the connection housing 117, such that the snap button is partial compressed. The front tab of the dog leg snap button contains a button which protrudes and enters the connection aperture 118 of the trocar mating fixture 114, thus securing the dog leg snap button in place, and coupling the camera console assembly 101 with the trocar assembly 102.

In some embodiments, the distal end of the trocar mating fixture 114 contains a pin and slot connection 119 as depicted in the illustrative embodiment shown in FIG. 5A-FIG. 5D. In one embodiment, the pin and slot connection 119 is situated on the back face of the trocar mating fixture 114, such that it is opposite the connection housing 117. The pin and slot connection 119 is configured to couple and secure the camera console assembly 101 and the trocar assembly 102. In addition, the pin and slot connection 119 is also configured to prevent the camera console base 108 from experiencing bending in the up and down direction during use, as well as to prevent one side of the camera console base 108 from lifting up during manipulation of the trocar assembly 102 so as to maintain an air tight connection between the camera console assembly 101 and the trocar assembly 102. In alternative embodiments, the pin and slot connection 119 is substituted for a press fit connection, an adhesive connection and/or any other connection method or type known in the art, that is capable of coupling and securing the camera console assembly 101 with the trocar assembly 102, as well as preventing the camera console base 108 from experiencing any bending and/or uplift during actuation.

In addition, in some embodiments the trocar mating fixture 114 contains a communications cut-out. The communications cut-out is configured to allow electrical communication components from the robotic camera assembly 103 that are routed through the trocar assembly 102 to mate and couple with a camera rigid board 115 (FIG. 6), so as to allow control information and other data to be sent from the robotic camera assembly 103 to the camera rigid board 115. In various embodiments, different types of electrical communication components may be utilized, including but not limited to flexible printed circuit boards ("FPCB"), and/or printed circuit boards ("PCB"). Additionally, in some embodiments, the trocar mating fixture contains a pass through configured to allow objects, such as surgical tools and/or devices to pass through the camera console assembly 101 and enter and pass through the trocar assembly 102. FIG. 5B shows an embodiment of the trocar mating fixture 114 according to one embodiment. In these embodiments, the trocar mating fixture 114 has a pass through 213 having an axis. FIG. 45 shows a cross-section view of a robotic camera system 300 according to one embodiment. As shown in FIG. 45, the pass through axis 212 runs parallel with a longitudinal axis 217 of the camera support tube, when said support tube has been inserted through the trocar assembly. As stated above the pass through is configured to permit access through the camera console assembly and through the trocar assembly, such that tools, devices, instruments or other components can enter into the operation site beneath the trocar assembly, while maintaining sealing. With this configuration, the robotic camera assembly, along with tools, devices and instruments can be inserted into an operation site utilizing the same trocar, and thus limiting the number of incisions needed to perform a procedure.

Figure 30:
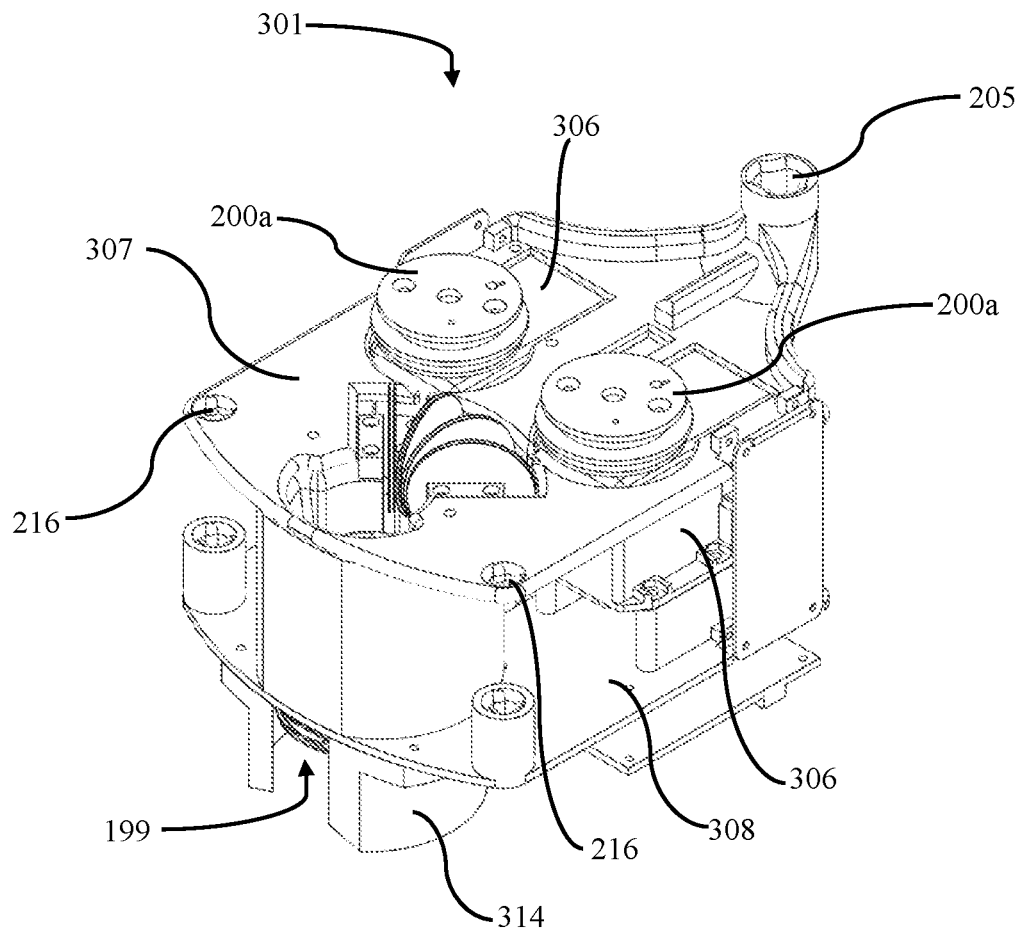
FIG. 30 is an isometric view of a camera console assembly according to one embodiment.
Figure 32A:
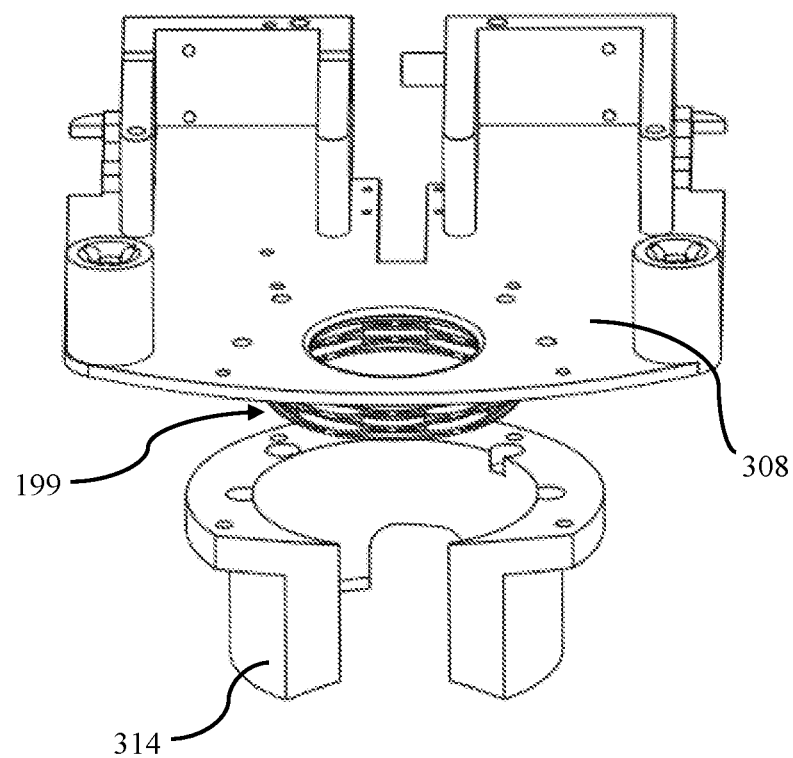
FIG. 32A is an exploded isometric view of the connection of a trocar mating fixture to camera console base according to one embodiment.
Figure 32B:
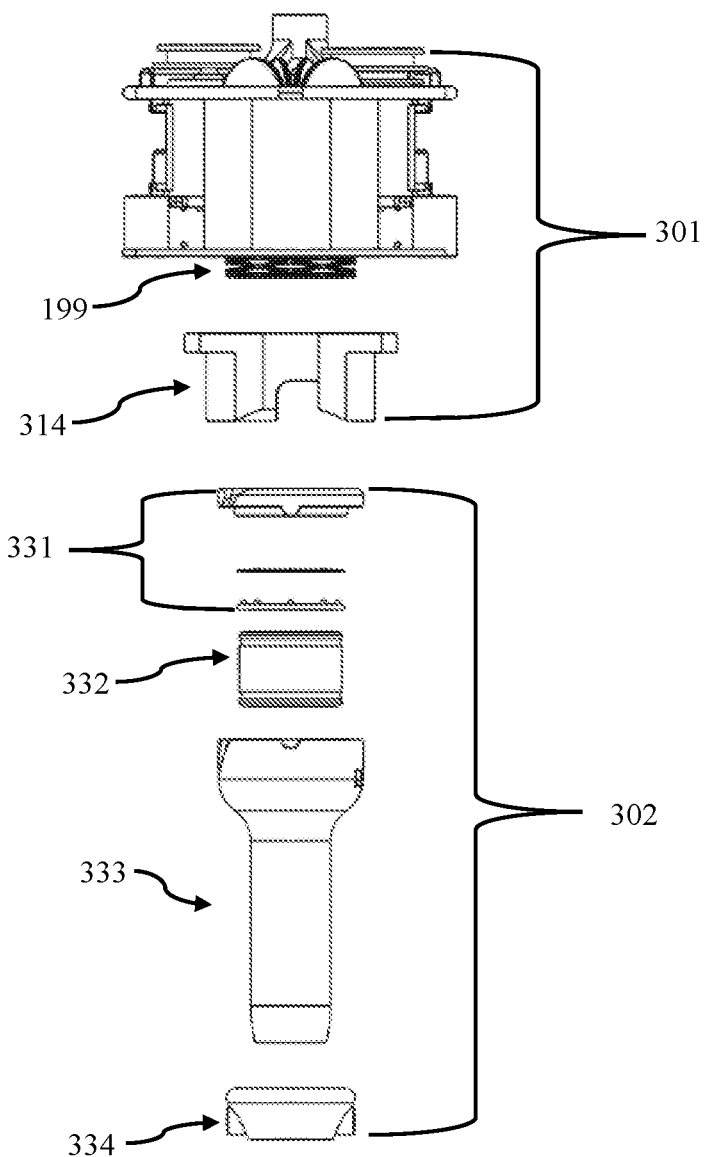
FIG. 32B is an exploded view of the connection between a camera console assembly according to one embodiment, and a trocar assembly according to one embodiment.

In some embodiments, the dog leg snap connection detailed above is eliminated. FIG. 30 shows an illustrative embodiment of a camera console assembly 301. In these embodiments, attached to console base 308 below the aperture in the console base 308 is a mating spring 199. As depicted in the embodiment shown in FIG. 32A, the mating spring 199 is configured to have a greater diameter than the aperture on the console base 308, so as to allow the mating spring to be directly attached to the console base. The mating spring is attached to the console base via an adhesive connection in one embodiment, while in other embodiments different connections techniques are utilized, including but not limited welded connections, pressed-fit or other techniques and/or methods known in the art. In these embodiments, trocar mating fixture 314 is affixed to the bottom of the console base 308. In one embodiment, a screw connection is utilized to affix the trocar mating fixture 314 to the console base 308, while in other embodiments other connection methods known in the are used, including but not limited to an adhesive connection, or welded connection. The mating spring 199 is configured to fit within the interior of the trocar mating fixture 314. In addition, in these embodiments, the trocar 333 is fabricated to have two pin and slot connections 201, with one connection on either side of the trocar. Trocar 333 is configured to fit within trocar mating fixture 314, such that when trocar 333 mates with trocar mating fixture 314 the mating spring 199 pushes trocar 333 and console base 308 apart, while the pin and slot connections 201 secures trocar 333 and console base 308 in place. This connection provides axial stiffness to the robotic camera system. In these embodiments, in order to separate the trocar from the console base, the user or surgeon applies pressure to the trocar such that the mating spring is compressed, and then rotates the trocar so that the pins are removed from the connections slots, thus releasing the trocar from the trocar mating fixture and console base. In alternative embodiments, the mating spring 199 is located on the exterior of trocar mating fixture. Additionally, in further embodiments, the trocar is configured to sit on the outside of the trocar mating fixture.

In some embodiments, the trocar mating fixture 114 is also utilized to mate and affix other components of the camera console assembly 101 to said assembly. In some embodiments, a pulley housing block 112 mates and couples to the proximal end of the trocar mating surface 114. As depicted in the illustrative embodiment of the camera console assembly 101 shown in FIG. 3, the pulley housing block 112 is configured to affix to the proximal end of the trocar mating fixture 114. In one embodiment, the pulley housing block 112 affixes to the trocar mating fixture 114 via a screw connection, while in other embodiments, the screw connection is substituted for a snap-fit connection, press-fit connection, adhesive connection, welded connection, and/or any other connection methods or combinations of methods known in the art.

The pulley housing block 112 is utilized to house and constrain camera redirecting pulleys 111. In one embodiment, the pulley housing block 112 is configured to house four camera redirecting pulleys 111, while in other embodiments the pulley housing block 112 is configured to house as few as one camera redirecting pulleys 111. In alternative embodiments, the pulley housing block 112 is configured to house four or more redirect pulleys 111.

The redirecting pulley(s) 111 redirect yaw and pitch cables of the robotic camera assembly 103 from a vertical orientation to a horizontal orientation such that the cables are able to be routed to a plurality actuator pulleys 105, and thus allowing the actuator 106 to actuate said cables.

Figure 7A:
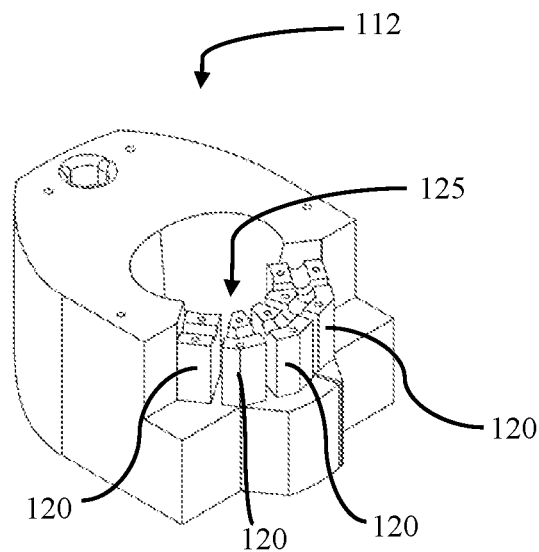
FIG. 7A is an isometric view of a pulley housing block according to one embodiment.

FIG. 7A depicts an illustrative embodiment of a pulley housing block 112. As shown in FIG. 7A, in one embodiment the pulley housing block 112 contains a plurality of redirect pulley slots 120. In one embodiment, the plurality of redirecting pulley slots 120 constrains the plurality of redirecting pulleys 111 (FIG. 8A-8B), with each of the plurality of redirecting pulleys 111 situated in one of the pluralities of redirecting pulley slots 120. In some embodiments, the pulley housing block 112 contains only one redirecting pulley slot 120. The redirecting pulley slots 120 are configured to allow the redirecting pulley 111 to sit within a respective slot, while preventing any of the redirecting pulleys 111 from coming in contact with another redirecting pulley 111. In one embodiment, the redirecting pulley slots 120 are angled such as to prevent redirecting pulleys 111 from contacting each other, while in other embodiments the redirecting pulley slots 120 are spaced apart thus preventing the pulleys 111 from contacting each other.

Figure 7B:
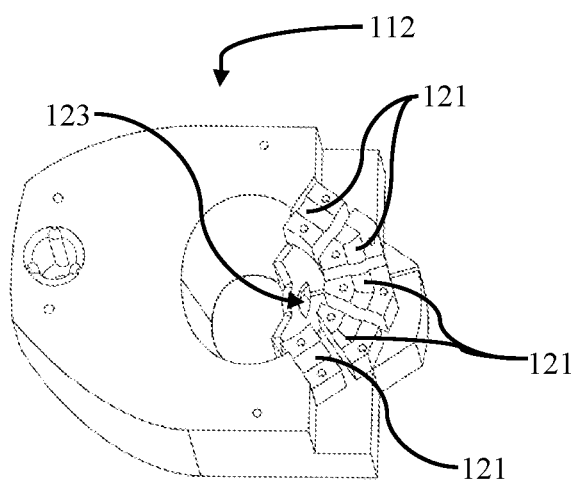
FIG. 7B is a top isometric view of a pulley housing block according to one embodiment.

In one embodiment, the redirecting pulley slot(s) 120 contains a shaft channel 121 located on the top of the redirecting pulley slot(s) 120 (FIG. 7A-7B). In this embodiment, a shaft containing two ends is used to hold and constrain the redirecting pulley 111 within the redirecting pulley slot 120. In one embodiment, one end of the shaft sits within one slot channel 121 of one redirecting pulley slots 120 and passes through an aperture in the redirecting pulley 111, with the other end of the shaft sitting within an adjacent slot channel 121 of another redirecting pulley slot 120. In some embodiments, a plurality of shafts are used to constrain each individual redirecting pulley 111 in its respective slot 120, while in alternative embodiments as few as one shaft is used to constrain all of the redirecting pulleys 111 in their respective slots 120. In addition to constraining the redirecting pulleys 111 within its respective slot 120, the shafts also act as a fulcrum, thus allowing the pulley to rotate about said shaft. The shaft can take on a variety of shapes and configurations in different embodiments, such as a cylindrical shape, a catenoidal shape, and/or any other shape able to allow a pulley to rotate about it. In alternative embodiments, the shaft is eliminated, with each redirecting pulley 111 fabricated with a protrusion on each side of said pulley 111, with said protrusions extending from the center of said pulley 111 and sitting within one of the shaft channels 121.

Figure 8A:
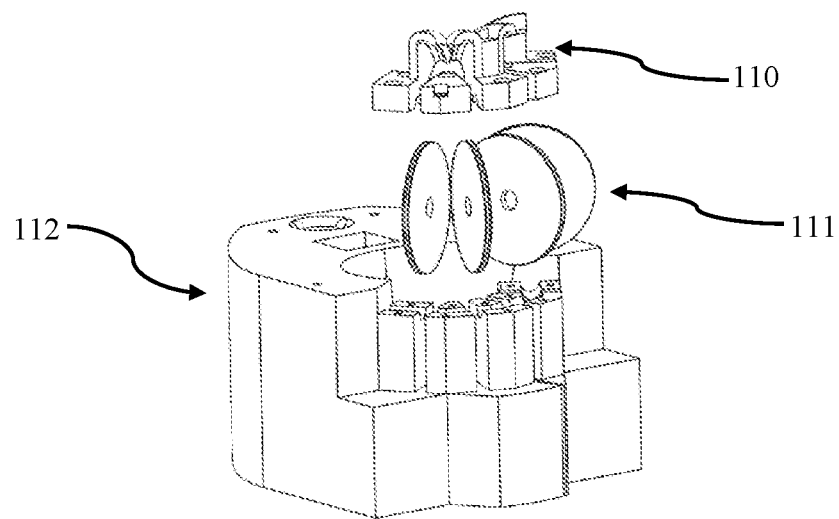
FIG. 8A is an exploded isometric view of a pulley housing block and components which may couple to a pulley housing block according to one embodiment.
Figure 8B:
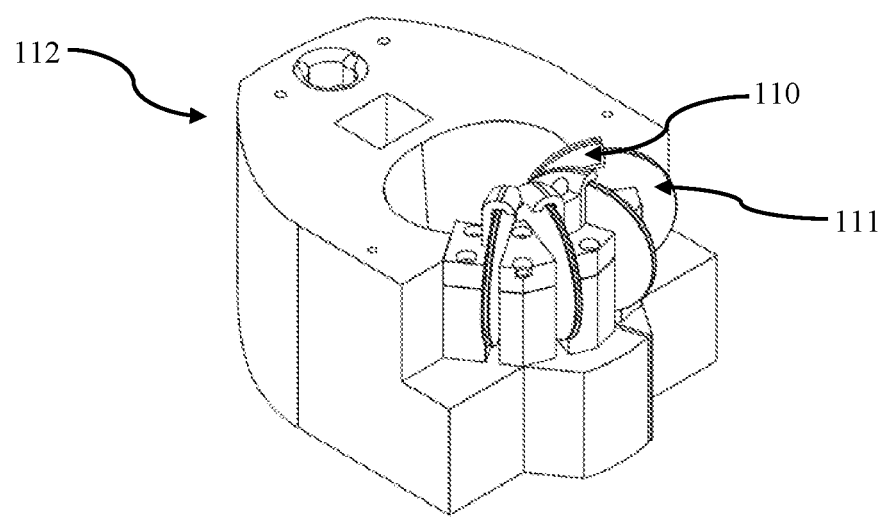
FIG. 8B is an isometric view of a pulley housing block with redirecting pulleys and redirecting pulley covers coupled according to one embodiment.

Additionally, in some embodiments, the redirecting pulleys 111 are also constrained in the redirecting pulley slots 120 via redirecting pulley covers 110. FIG. 8A shows an exploded view of an illustrative embodiment of the pulley housing block 112 highlighting the redirecting pulley covers 110. As depicted in the embodiment shown in FIG. 8A, the redirecting pulley covers 110 are configured to clamp around the redirecting pulleys 111 and affix to the top of the redirecting pulley slots. In addition to constraining the redirecting pulley(s) 111 in their respective slot(s), the redirecting pulley cover(s) 110 are also configured to constrain cables such that said cables maintain contact with the redirecting pulley 111. FIG. 8B shows an additional view of an illustrative embodiment of the pulley housing block 112 with the redirecting pulleys 111 constrained by the redirecting pulley covers 110.

In some embodiments, the redirecting pulley covers 110 are affixed to the top of the redirecting pulley slots 120 via a screw connection, while in alternative embodiments the redirecting pulley covers 110 are affixed to the redirecting pulley slots 120 via snap-fit connections. In alternative embodiments, a variety of connection techniques are utilized to affix the redirecting pulley covers 110 to the redirecting pulley slots 120 including but not limited to press-fit connections, adhesive connection and/or any other techniques and/or combination of connection techniques known in the art.

Additionally, in some embodiments the pulley housing block 112, contains a stiffening rod aperture, which is configured to allow a stiffening rod (not shown) to enter said aperture. The stiffening rod acts as an alignment feature to align the robotic camera system 100 and devices to be inserted, such as the Virtual Reality Surgical Device disclosed in International Patent Application No. PCT/US2015/029247 (published as International Patent Publication No. WO2015171614A1), so as to ensure that said device(s) is properly aligned for insertion into a patient. In addition, in some embodiments, the stiffening rod is also used to mate the robotic camera system 100 with devices to be inserted into a patient.

In one embodiment, the stiffening rod contains two threaded ends that allow said rod to connect to the pulley housing block 112 via a screw which is pressed in the stiffening rod aperture. In other embodiments, different connections techniques are utilized including but not limited to, snap fit connections, pressed fit connections, and/or any other techniques or combination of techniques known in the art. Alternatively, in some embodiments, the stiffening rod is eliminated. In various embodiments, the stiffening rod is fabricated out of a variety of materials including but not limited to carbon fiber, stainless steel, and/or composite materials.

Figure 7C:
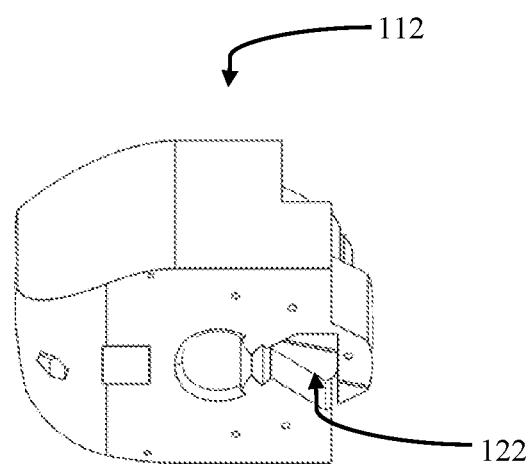
FIG. 7C is a bottom isometric view of a pulley housing block according to one embodiment.

In some embodiments, the pulley housing block 112 contains a flex cavity 122 located on the interior of said housing block 112. FIG. 7C shows a bottom view of an illustrative embodiment of the pulley housing block 112, highlighting the flex cavity 122. The flex cavity 122 is configured to allow electrical communication components from the robotic camera assembly 103 to redirect down towards the communication cut-out of the trocar mating fixture 114. Additionally, the flex cavity 122 is configured to accommodate the minimum allowable bend radius of the electrical communication components prior to said components being damaged and/or bent rendering them unusable. As mentioned above, in various embodiments different types of electrical communication components may be utilized, including but not limited to flexible printed circuit boards ("FPCB"), and/or printed circuit boards ("PCB").

Figure 20A:
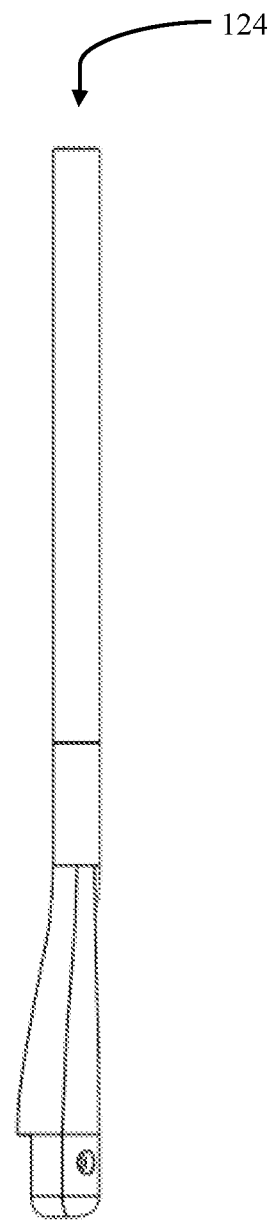
FIG. 20A is a front isometric view of a camera support tube according to one embodiment.
Figure 20B:
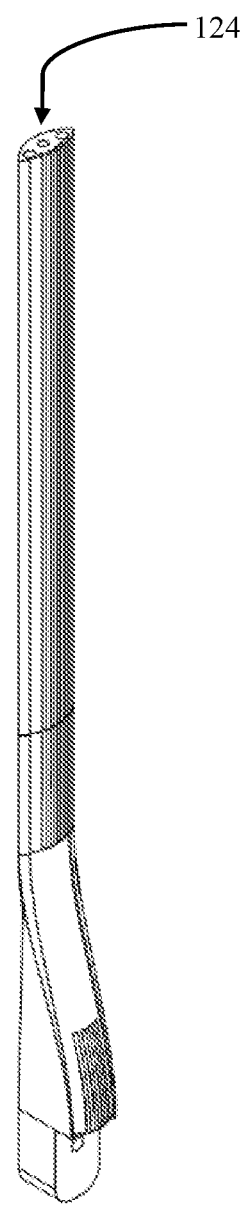
FIG. 20B is a back isometric view of a camera support tube according to one embodiment.

In some embodiments, the pulley housing block 112 contains a camera support tube aperture 123 (FIG. 7B) situated on the interior of the pulley housing block 112. The camera support tube aperture 123 is configured to allow a camera support tube 124 (FIGS. 20A-20B) to mate and couple with the pulley housing block 112, thus mating the robotic camera assembly and the camera console assembly. FIGS. 20A-20B show multiple views of an illustrative embodiment of a camera support tube 124. In addition to providing a mating point for the camera support tube 124, the camera support tube aperture 123 is configured to increase the effective stiffness of the camera support tube 124, by providing bending resistance for the camera support tube 124 while cables are actuated. In various embodiments, the camera support tube aperture 123, is constructed with walls that extend down and surround the camera support tube 124, thus providing additional support for the tube, such that the bending experienced by the tube when cables are actuated is minimal thus preventing the tube from deforming and/or becoming damaged.

In various embodiments, different connection techniques are utilized to mate and couple the camera support tube 124 in the camera support tube aperture 123, including but not limited to a screw connection, a press-fit connection and/or a snap fit connection. In alternative embodiments, a rivet connection and/or any other connection technique and/or combination of techniques can be utilized to mate and couple the camera support tube 124 in the camera support tube aperture 123.

Additionally, in some embodiments the pulley housing block 112 contains an assembly slot located on the back of said housing block for cables from the robotic camera assembly to pass in and out of the pulley housing block 112 such that any component of the camera console assembly can be removed and/or swapped out without having to de-cable or unstring the robotic camera assembly.

Furthermore, in various embodiments, the pulley housing block 112 contains an insertion opening 125 (FIG. 7A). The insertion opening is configured to configured to allow objects such as surgical tools and/or a robotic device to pass through and proceed to the trocar assembly 102. In some embodiments, the insertion opening 125 is fabricated to contain sloped interior walls to allow objects and devices to pass through said opening without contacting and getting caught on any sharp edges. In addition, the insertion opening 125 is also utilized to guide tools, devices and other objects through the trocar assembly 102 for ease of insertion into a patient.

In some embodiments, the pulley housing block 112 also contains a cavity configured to match the configuration and shape of the connection housing 117 of the trocar mating fixture 114 (FIG. 5B), so as to allow the top of the connection housing 117 to enter and sit within said cavity. In some embodiments, the cavity is fabricated as an orifice so as to allow a connector, such as a dog snap button as detailed above, to be removed from the trocar mating fixture 114 without having to disconnect and remove the pulley housing block 112, as well as to provide for ease of assembly of the entire system. In alternative embodiments, the cavity is configured as an extruded slot which allows the top of the connection housing 117 to enter said cavity, while in other embodiments, the cavity is eliminated.

Figure 9A:
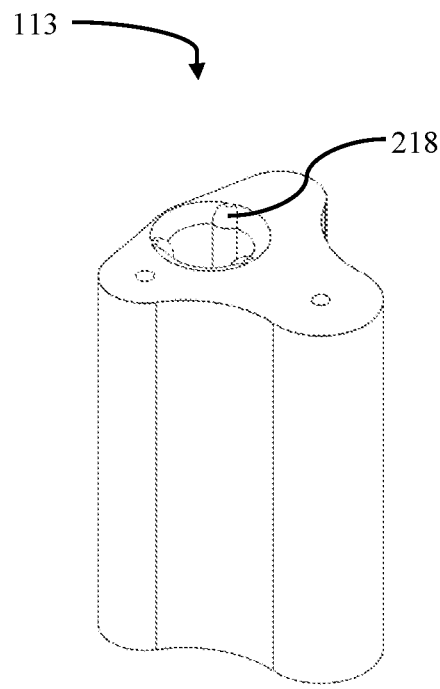
FIG. 9A is an isometric view of a console mating support according to one embodiment.
Figure 9B:
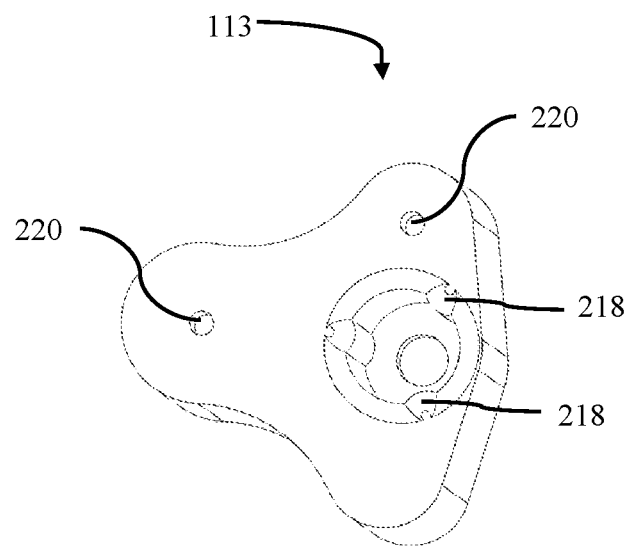
FIG. 9B is a top isometric view of a console mating support according to one embodiment.

In some embodiments, the camera console assembly 101 also contains a console mating support 113, which affixes to camera console base 108. FIGS. 9A-9B show isometric views of an illustrative embodiment of the console mating support 113. The console mating support 113 acts as an alignment feature and stiffening element for the entire system 100. In one embodiment, the console mating support 113 contains an aperture for alignment, which is constructed to allow a stiffening rod to enter the aperture, where said rod is coupled to the console mating support 113 via a screw connection. In alternative embodiments, a variety of connection techniques are used to couple a stiffening rod to the console mating support 113 including but not limited to snap-fit connection, a press-fit connection, a threaded connection and/or any other connection techniques or combinations of techniques in the art.

In addition, as mentioned above, in various embodiments, the console mating support 113 is configured to provide added stability to the overall system. In some embodiments, located on the inner surface of the aperture for alignment are a plurality of stiffening bumpers 218 (FIGS. 9A-9B) which contact the stiffening rod inserted into the aperture. In these embodiments, the stiffening bumpers 218 are fabricated as half cylinders, which extend from the top of the aperture to the bottom of said aperture. The stiffening bumpers are configured to reduce the amount of over constraint in the system 100, by providing a minimum amount of contact points for a stiffening rod and thus stabilizing and securing said rod when the system 100 is being used.

Figure 9C:
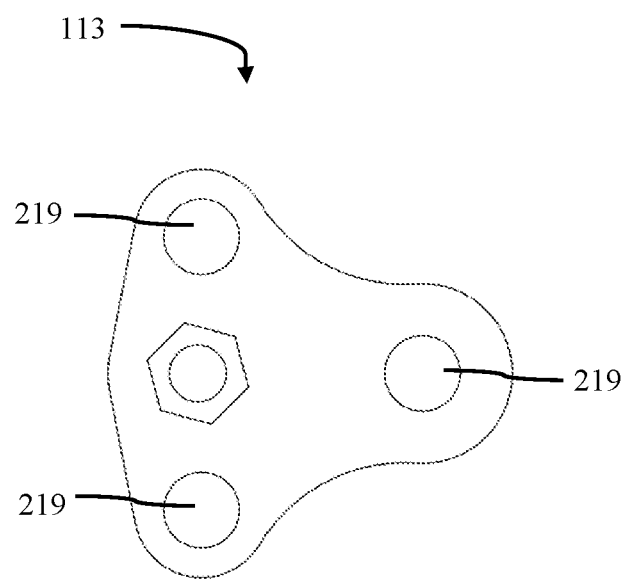
FIG. 9C is bottom profile view of a console mating support according to one embodiment.

As mentioned above, the console mating support 113 affixes to the camera console base 108. FIG. 9C shows a bottom profile view of an illustrative embodiment of a console mating support 113. As depicted in the embodiment shown in FIG. 9C, located on the bottom of the console mating support 113 are a plurality of connection holes 219, which are used to couple and affix the console mating support 113 with the camera console base 108 (not shown). In various embodiments, a variety of connection techniques and methods are utilized such as screw connections, press-fit connections, snap-fit connections, and/or any other method or techniques or combination thereof, known in the art, capable of securing and coupling the console mating support 113 with the camera console base 108. Likewise, as depicted in the illustrative embodiment shown in FIG. 9B, in some embodiments located on the top surface of the console mating support 113 are a plurality of mating holes 220. In these embodiments, the mating holes are used to mate the top of console mating support 113 with a top console body 107 (not shown). In various embodiments, a variety of connection techniques and methods are utilized including but not limited to threaded connections, snap-fit connections, pressed-fit connections, adhesive connections, and/or any other method or technique known in the art.

In alternative embodiments, the camera console assembly does not contain a console mating support. As depicted in the illustrative embodiment shown in FIG. 30, in some embodiments, camera console assembly 301 contains a plurality of stiffening rod apertures 216 which are used to mate and couple the top console body 307 with the camera console base 308. In these embodiments, stiffening rods enter and pass through the stiffening rod apertures 216 and enter and mates with slots located on the camera console base 308 to couple the top console body 307 and the camera console base 308. In addition, in some embodiments, the top console body 307, contains an alignment slot 205 for aligning a device to be inserted through the trocar assembly and enter into the patient's body. In these embodiments, one end of an alignment rod enters and mates with the alignment slot 205 and the other end enters into a corresponding slot on the device, thus aligning the device for insertion through the trocar assembly. Additionally, the alignment rod, also mates the device with the console assembly.

Figure 10A:
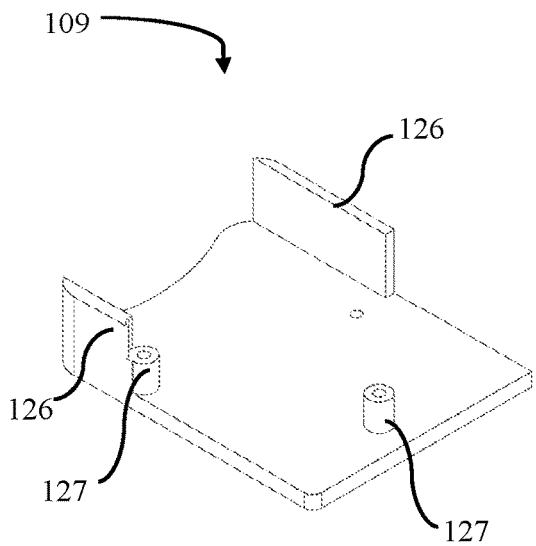
FIG. 10A is an isometric view of a flex shield according to one embodiment.
Figure 10B:
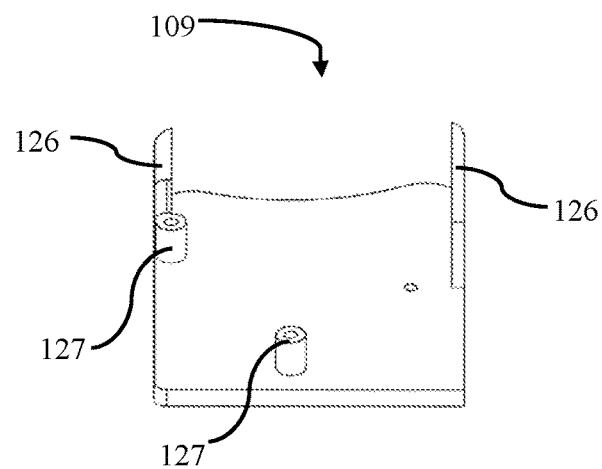
FIG. 10B is an additional isometric view of a flex shield according to one embodiment.
Figure 10C:
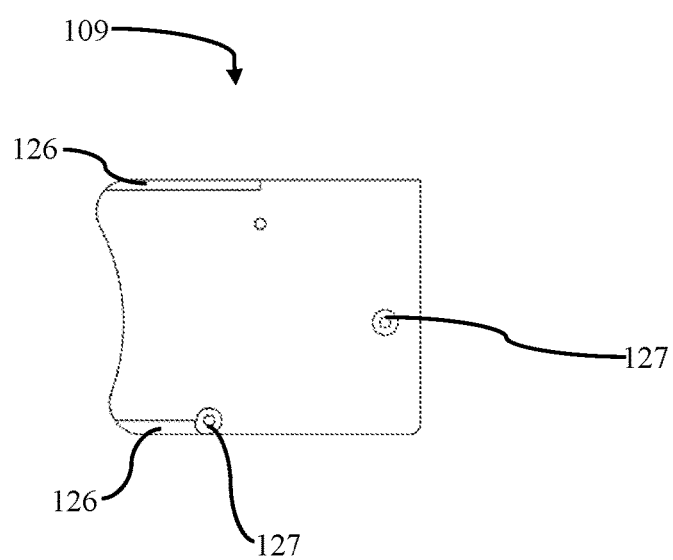
FIG. 10C is a top profile view of a flex shield according to one embodiment.

In some embodiments, the camera console assembly 101 contains a flex shield 109 which affixes to the bottom of the camera console base 108. FIGS. 10A-10C show multiple views of an illustrative embodiment of a flex shield 109. The flex shield 109 provides a protective casing for electrical communication components being routed from the robotic camera assembly so as to prevent said electrical communication components from coming into contact with other objects and components while the system is in use. In addition, in some embodiments the flex shield 109 provides a surface for a camera rigid board 115 (FIGS. 11A-11B) to sit upon, as well as a mating surface so as to allow the camera rigid board 115 to couple to the camera console base 108.

As illustrated in the embodiment shown in FIGS. 10A-10C, in one embodiment the flex shield 109 contains a contoured edge, which is configured to have the same shape as the proximal portion of the trocar assembly 102 so as to allow the flex shield 109 to rest along the outer surface of the proximal portion of the trocar assembly 102. In various embodiments, the contoured edge can take on a variety of configurations that allow the flex shield 109 to rest along the outer surface of the proximal portion of the trocar assembly 102, while in other embodiments the contoured edge is eliminated. In addition, in some embodiments, the flex shield contains side walls 126. The side walls 126 provide protection for electrical communication components that are routed from the robotic camera assembly 103 to the camera rigid board 115. In addition, as shown in the embodiment depicted in FIGS. 10A-10B the side walls 126 extend proximally, so as to provide separation from the camera console base 108 to allow electrical communication components to enter the flex shield 109 and mate with the camera rigid board 115. In some embodiments, the side walls 126 run along the entire edge of the flex shield 109, while in other embodiments the side walls 126 run along only a portion of the edge of the flex shield 109.

As mentioned above, in some embodiments the flex shield 109 mates and couples to the bottom of the camera console base 108. In various embodiments, a variety of connection methods and techniques are utilized to couple the flex shield 109 to the bottom of the camera console base 108, including but not limited to threaded connections, snap fit connections, press-fit connections, welded connections and/or adhesive connections. In one embodiment, the flex shield 109 contains a plurality of flex shield stand-offs 127 (FIG. 10A-10C). In this embodiment, the flex shield stand-offs 127 provide a surface for the flex shield 109 to mate and couple to the camera rigid board 115, with said camera rigid board coupling to both the flex shield 109 and the bottom of the camera console base 108. Furthermore, in this embodiment the flex shield stand-offs 127, are also utilized to elevate the camera rigid board 115 so as to allow electrical communication components to connect to both the bottom and top of the camera rigid board 115, as further detailed below.

Figure 11A:
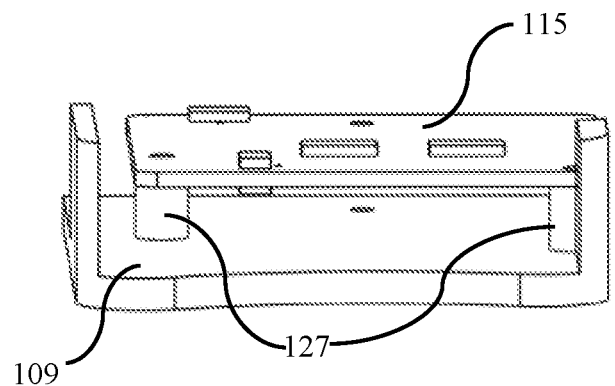
FIG. 11A is a front isometric view of a camera rigid board coupled to a flex shield according to one embodiment.
Figure 11B:
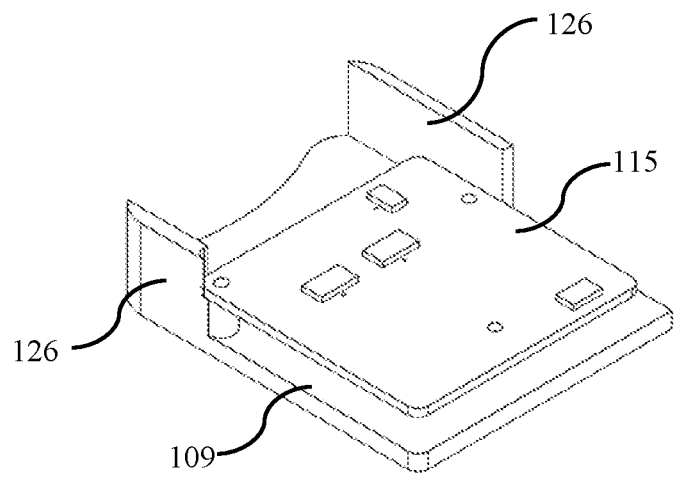
FIG. 11B is a top isometric view of a camera rigid board coupled to a flex shield according to one embodiment.

FIGS. 11A-11B, show multiple views of the connection between the flex shield 109 and camera rigid board 115. In one embodiment, screws enter through the bottom of the flex shield 109, through the flex shield stand-offs 127 with said screws passing through apertures in the camera rigid board 115, as well as through standoffs sandwiched between the camera rigid board 115 and the camera console base 108, with said screws entering thread connection holes on the camera console base 108. In alternative embodiments, the screw connections may be substituted for other connection techniques known in the art, including but not limited to press-fit connections and/or snap-fit connections.

As detailed above, the camera rigid board 115 rests upon the flex shield standoffs 127. The camera rigid board 115 acts as an intermediary for electrical communication components routed from the robotic camera assembly 103, with said rigid board taking data and information for electrical communication components and routing the information to the requisite locations such as motor control boards, and external computers. In one embodiment, the camera rigid board 115 contains a top and bottom surface, with both surfaces containing a plurality of connectors for which electrical communication components connect to.

As mentioned above, a variety of electrical communication components are used in various embodiments, including but not limited to PCBs and FPCBs. In one embodiment, a FPCB from the camera rigid board 115 is routed to a motor control board, with said FPCB providing position and orientation sensor data from the robotic camera assembly. Likewise, in one embodiment two FPCBs are routed from the camera rigid board 115 to a computer board which provides camera feeds and data obtained from sensors located on the robotic camera assembly. In addition, in one embodiment, the camera rigid board 115 contains a plurality of traces which are routed across said board and configured to ensure that traces from the electrical communication components of the robotic camera assembly contain the same length, so that data and camera feeds reach their respective location at the same time, thus reducing any disruption in the data flow of the system.

As detailed above, in some embodiments, the camera rigid board 115 is operatively connected to the motor control board. The motor control board is configured to process position and orientation data obtained from sensors of the robotic camera assembly, as well as from a sensor system tracking the position and orientation of a head-mounted display worn by a surgeon, as detailed below. The motor control board processes the data obtained from the aforementioned sensors and sensor system and transmits actuation commands to a plurality of actuators 106 informing the actuators 106 how much actuation force should be applied to cable(s) of the robotic camera assembly in order to actuate a stereoscopic camera 143 to follow and align with the head movements of the surgeon. In these embodiments, the motor control board is rigidly affixed to the camera console assembly.

As detailed above, in some embodiments, the camera console base 108 is outfitted with a plurality of actuator mounts 116, which are used to secure a plurality of actuators 106 (FIG. 2A). The actuators 106 are utilized to actuate cables that are routed from the robotic camera assembly 103. In some embodiments, an actuator pulley 105 is operatively coupled to the actuator 106. In these embodiments, the actuator pulley 105 is configured to transmit a torque force from the actuator 106 on to the cables of the robotic camera assembly. In some embodiments, the actuator pulleys 105 are encased by actuator pulley covers 104, which affix to the top of the actuator 106. The actuator pulley covers 104 are configured to constrain and retain cables within the groove of the actuator pulley 105 during actuation.

In different embodiments, different types of actuators are utilized including but not limited to servomotors, rotary actuators, linear actuators and/or stepper motors. In one embodiment, the system 100 contains four (4) actuators, with two actuators designated to actuate yaw cables and two actuators designated to actuate pitch cables routed from the robotic camera assembly 103. Alternatively, in other embodiments, the system contains only two (2) actuators, with one actuator designated to actuate yaw cables and one actuate pitch cables routed from the robotic camera assembly.

In addition to the actuators 106 being secured to the camera console base 108 via the actuator mounts 116, in some embodiments a top console body 107 is utilized to provide additional stability to the entire system 100, as well as secure the actuators 106 in place. The top console body 107 is configured to constrain the camera console assembly 101 and prevent the assembly from bending inward and collapsing in on itself, due to tension forces from the actuators 106 during actuation of cables.

Figure 12:
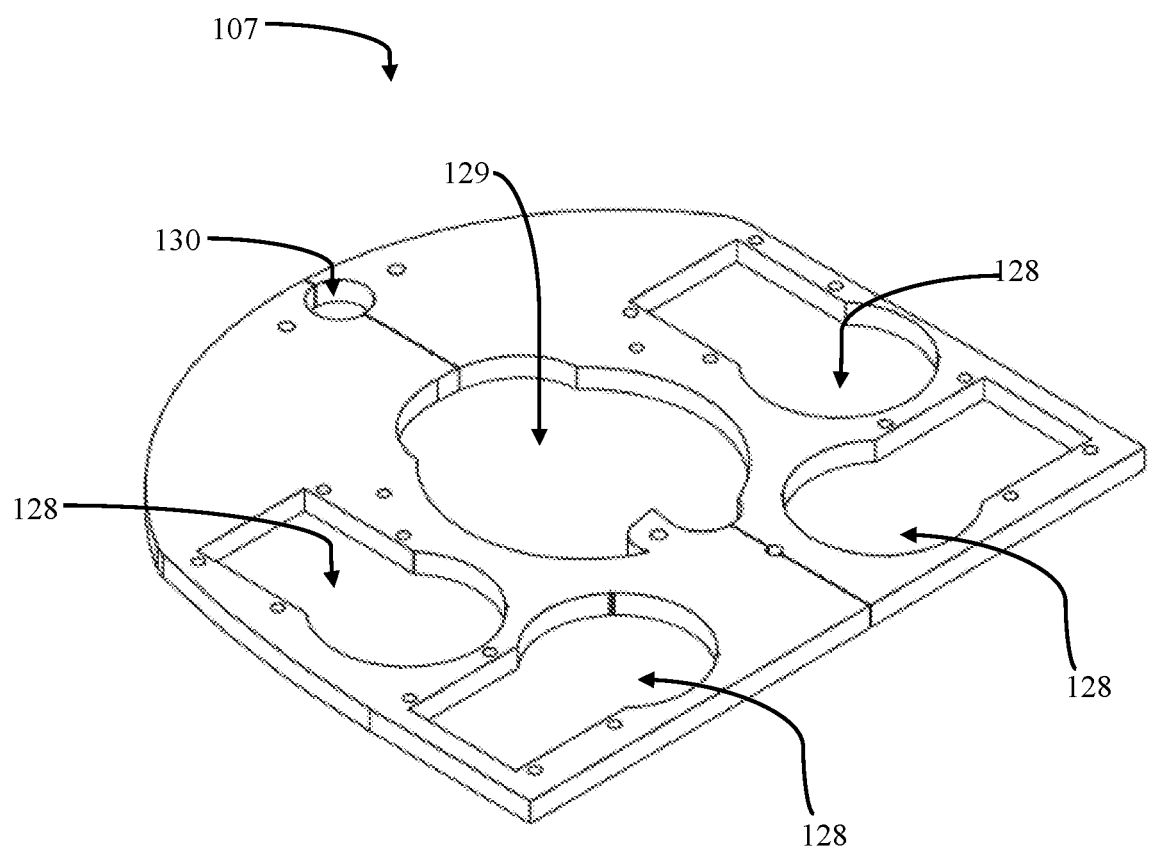
FIG. 12 is an isometric view of a top console body according to one embodiment.

As depicted in the illustrative embodiment of the camera console assembly 101 shown in FIG. 2C, the top console body 107 is located proximal to the actuators 106, with said top console body 107 configured to affix to the top surface of the actuators 106. FIG. 12 shows an isometric view of an illustrative embodiment of a top console body 107. As shown in FIG. 12, in one embodiment the top console body 107 contains a plurality of attachment holes, for affixing the top console body 107 to the actuators 106 (not shown in FIG. 12), as well as affixing and securing a plurality of actuator pulley covers 104 to the top of the top console body 107 and around the actuator pulleys 105. In addition, in some embodiments, the attachment holes are used to couple and mate the top console body to the top surface of the pulley housing block 112, as well as to couple the top console body 107 to the top surface of the console mating support. In various embodiments, different attachment methods and techniques known in the art are utilized, including but not limited to screw connections, press-fit connections, snap-fit connections, and/or any other method or technique or combination thereof known in the art.

As shown in FIG. 12, in one embodiment the top console body 107 contains a plurality of actuator apertures 128. The number of actuator apertures 128 directly correlate to the number of actuators 106 of the system 100, thus in some embodiments the top console body 107 contain as few as one actuator aperture 128, while in other embodiments the number of actuator aperture 128 found in the top console body 107 can range from two (2) to four (4), or more. The actuator aperture(s) 128 are fabricated to take on the shape of the actuator 106, as well as the actuator pulley 105 affixed to said actuator, such that the top surface of the actuator 106 is flush with the top console body 107 to allow the actuator pulley 105 is sit above the top console body 107 (FIG. 2C).

Likewise, in some embodiments, the top console body 107 contains a device opening 129 situated in the center of said plate. In one embodiment, the device opening 129 is located directly above the pulley housing block 112, with said opening configured to have a cross sectional area large enough to allow access to the redirecting pulleys 111, as well as allow a device and/or object to pass through the device opening 129 and enter the insertion opening 125 of the pulley housing block 112. In addition, in some embodiments, the device opening 129 is configured to provide space for a stiffening rod to pass through and enter an aperture located on the console mating support 113.

In some embodiments, the top console body 107 contains a proximal stiffening rod aperture 130. In these embodiments, the proximal stiffening rod aperture 130, is located directly above the stiffening rod aperture of the pulley housing block 112. In addition, in these embodiments, the proximal stiffening rod aperture 130 is configured to have the same cross-section as the stiffening rod aperture, so as to allow a stiffening rod to pass through the proximal stiffening rod aperture 130 and enter the stiffening rod aperture.

In one embodiment, the top console body 107 is fabricated as two halves that affix to one another via snap-fit connections. In other embodiments, the snap-fit connection is substituted for a pin-hole connection, while in further embodiments other connection types and/or methods are utilized, such as adhesive connection, welded connections, magnetic connection, and/or any other method or combination of methods known in the art. In alternative embodiments, top console body 107 is fabricated as one rigid piece. In some embodiments, the top console body 107 is constructed out of stainless steel, while in alternative embodiments the plate is constructed out of plastics, ceramics and/or other material types known in the art, that are capable of supporting the camera console assembly 101.

As mentioned above, in some embodiments the camera console assembly is configured to have two actuators. FIG. 30 shows an illustrative embodiment of camera console assembly 301 containing two actuators. In these embodiments, there is a set of two (2) counter-rotating pulleys 200a and 200b for each actuator 306 providing actuation in one degree of freedom. In these embodiments, one cable is used in conjunction with one actuator, one set of counter-rotating pulleys, and a torsion spring 202 to provide one degree of freedom to the camera assembly, in either yaw or pitch. FIGS. 31A-31C shows an illustrative embodiment of the counter-rotating pulley set. As seen in FIGS. 31A-31C, in these embodiments, the counter-rotating pulleys 200a and 200b are stacked on one another, with the bottom counter-rotating pulley 200b fixed directly to the actuator 306. In between the set of counter-rotating pulleys 200a and 200b is torsion spring 202, which sits in a housing in between the set of counter-rotating pulleys. The torsion spring is coupled to both counter-rotating pulleys 200a and 200b. The top counter-rotating pulley 200a is translationally constrained, such that the pulley can only rotate about the axis of said pulley. Both the bottom and top counter-rotating pulleys each contain a termination site, where one end of the cable, used for actuation, is terminated. The cable is routed through either the yaw actuation assembly, or pitch actuation assembly, with one end of said cable routed around and terminating on the bottom counter-rotating pulley 200b, and the other end of the cable routed around and terminating on the top counter-rotating pulley 200a. The cable is terminated so that the length of the cable is fixed, such that when the actuator is actuated both pulleys rotate in the same direction, positively or negatively rotating the stereoscopic camera about the desired degree of freedom.

In these embodiments, as the actuator actuates the bottom counter-rotating pulley 200b, said pulley pulls in on the end of the cable that is terminated on the pulley. While the bottom counter-rotating pulley 200b rotates, the top counter-rotating pulley 200a also rotates due to the coupling between said pulleys. The pulling in on the cable pans or tilts the stereoscopic camera, depending on how the cable is routed through the camera assembly. In order to pan or tilt the stereoscopic camera in the opposite direction, the actuator is rotated in the opposite direction. When the actuator is rotated in the opposite direction the torsion spring 202 applies a force to the top counter-rotating pulley 200a as the torsion spring moves back towards its free state. The force applied by the torsion spring causes slack form the other end of the cable to be pulled in, which causes the stereoscopic camera to pan or tilt in the opposite direction.

Trocar Assembly

Figure 13:
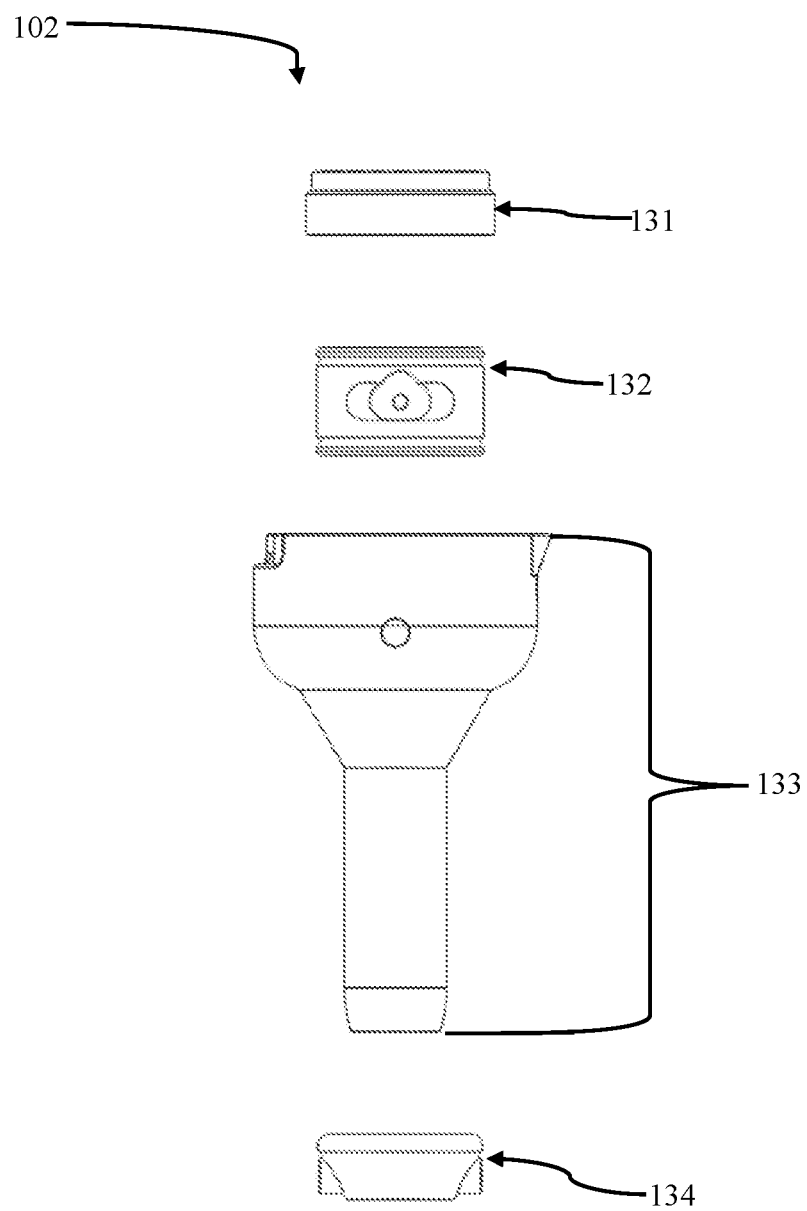
FIG. 13 is an exploded side profile view of a trocar assembly according to one embodiment.

As detailed above, attached to the distal end of the trocar mating fixture 114 is the trocar assembly 102. FIG. 13 shows an exploded view of one embodiment of the trocar assembly 102. As seen in the embodiment shown in FIG. 13, the trocar assembly 102 contains multiple components that couple together to create said assembly. The trocar assembly 102 functions as a portal for surgical devices, tools and/or any other objects to be inserted into a patient's body.

Figure 14A:
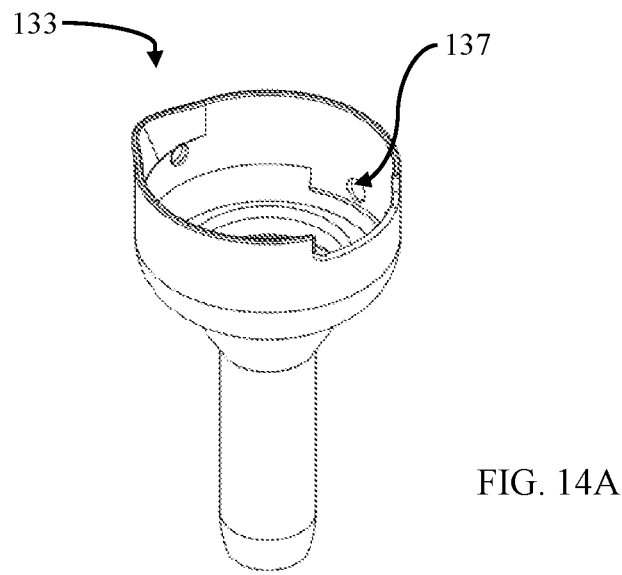
FIG. 14A is an isometric view of a trocar according to one embodiment.

In one embodiment, the trocar assembly 102 contains a trocar 133. FIG. 14A shows an illustrative embodiment of a trocar 133 according to one embodiment. The trocar 133 is configured to allow the robotic camera assembly 103 and other surgical devices and tools located outside of a patient's body to enter the patient's body, while maintaining a seal, such that the patient's abdomen remains insufflated throughout the entire procedure.

Figure 14B:
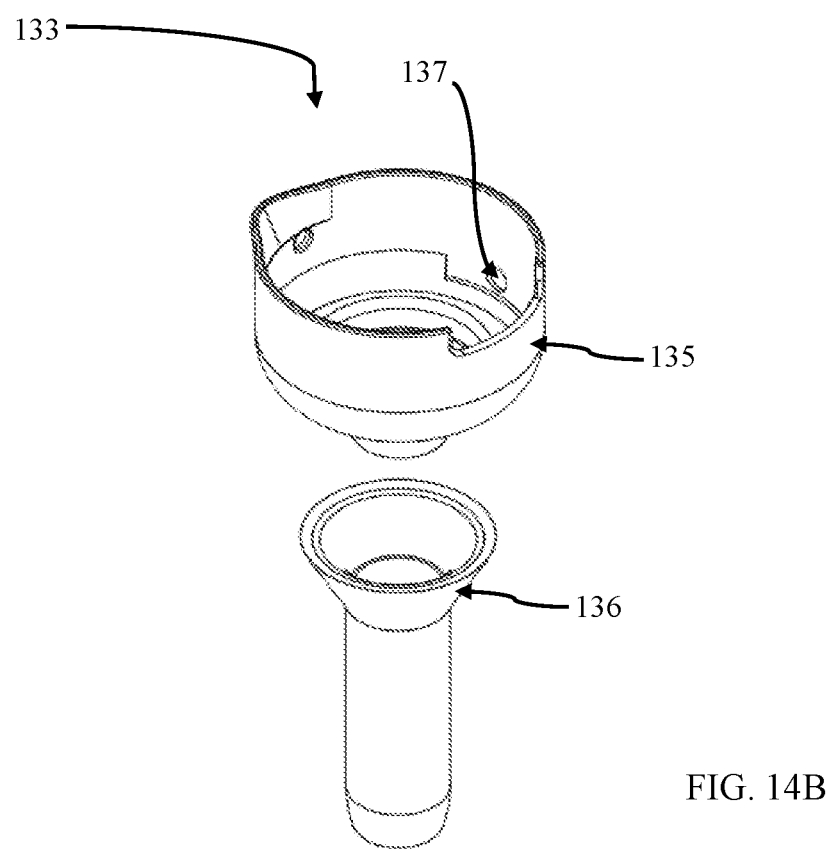
FIG. 14B is an exploded isometric view of a trocar according to one embodiment.
Figures 17A, 17B:
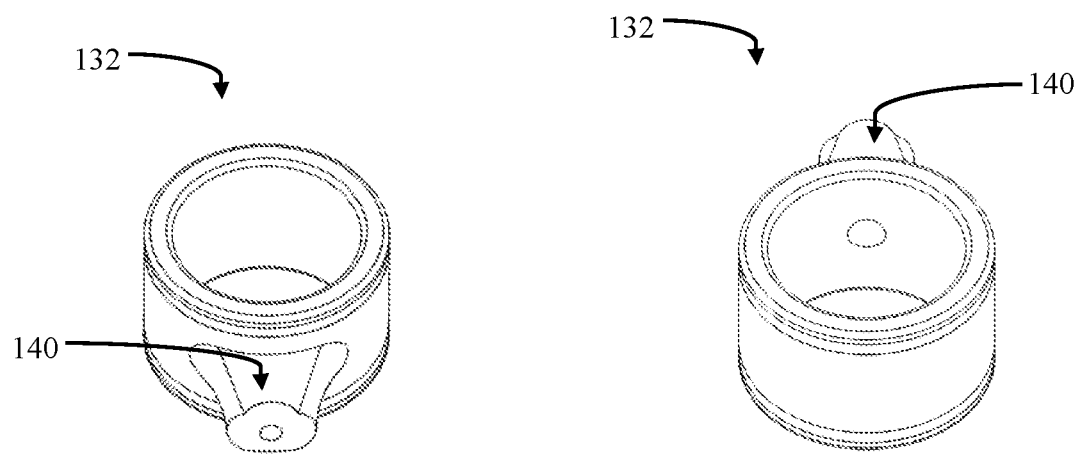
FIG. 17A is a front isometric view of an inflatable seal according to one embodiment.
FIG. 17B is a back isometric view of an inflatable seal according to one embodiment.

FIG. 14B shows an exploded view of a trocar 133 according to one embodiment. As shown in FIG. 14B, in one embodiment, the trocar 133 is fabricated as two pieces, a main trocar body 135 and a trocar neck 136. The main trocar body 135 contains a distal portion that is configured to sit inside of the trocar neck 136. In one embodiment, the main trocar body 135 is coupled to the trocar neck 136 via an adhesive connection, such as to create an air tight seal, thus preventing air or carbon dioxide from escaping through the trocar 133 during insufflation. In other embodiments, different connection methods and techniques known in the art are utilized to affix the main trocar body 135 to the trocar neck 136. Alternatively, in other embodiments, the main trocar body 135 and the trocar neck 136 are fabricated as one piece.

Figures 18A, 18B:
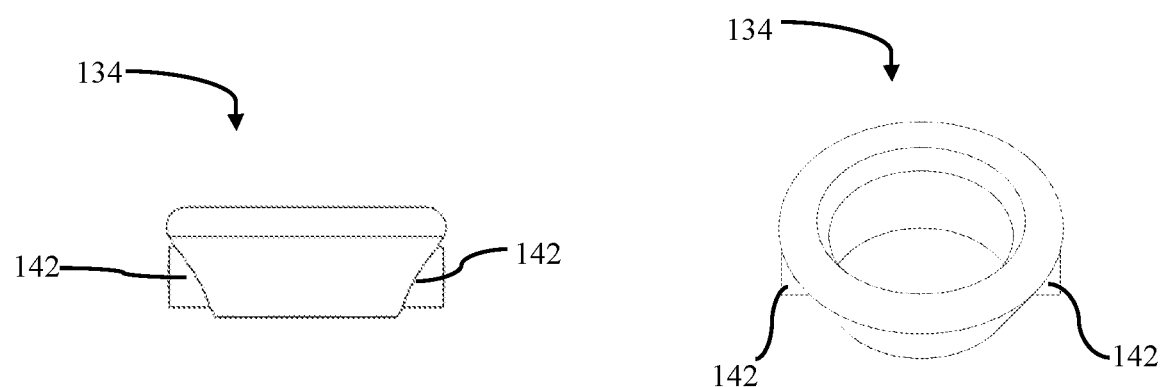
FIG. 18A is a front profile view of a winged ring according to one embodiment.
FIG. 18B is a top isometric view of a winged ring according to one embodiment.

During utilization, the main trocar body 135 is situated on the exterior abdomen wall of the patient, with the trocar neck 136 inserted in the patient's abdomen wall to allow for insertion of the robotic camera assembly 103, as well as various surgical devices and apparatuses. In one embodiment, affixed to the trocar neck 136 is a winged ring 134. The winged ring 134 is configured to affix the trocar assembly 102 to the exterior abdomen wall of the patient to prevent any movement of the trocar assembly 102 during the procedure, as well as when a robotic camera assembly and surgical devices and tools are inserted into the patient's body. FIGS. 18A-18B show multiple views of the winged ring 134 according to one embodiment. As shown in FIG. 18B, in one embodiment, the winged ring 134 configured to have a body with a hollow center, with the center configured to fit around the trocar neck 136. In this embodiment, located on either side of the body of the winged ring 134 is a screw 142. The screws 142 are utilized to secure the trocar assembly 102 to the patient's body. During a procedure, once the surgeon has inserted the trocar neck 136 into the patient's abdominal wall, the surgeon wraps a piece of surgical thread around each of the screws 142 and sews the surgical thread into the patient's abdominal wall, thus securing the trocar assembly 102 to the patient's body. In one embodiment, the winged ring 134 is coupled to the trocar neck 136 via two screws that are held in by friction. In other embodiments, different coupling methods and techniques known in the art are utilized to couple the winged ring 134 to the trocar neck 136, including but not limited to, snap-fit connections, adhesive connection, welded connection and/or a threaded connection. In addition, in alternative embodiments, the winged ring 134 and the trocar neck 136 are fabricated as one piece.

In one embodiment, the main trocar body 135 contains a seal port 137 which is located on the side wall of said main trocar body 135. In this embodiment, a Luer Lock connection passes through the seal port 137 and connects to an air-port 140 located on an inflatable seal 132, as detailed below. The seal port 137 is located on the sidewall of the main trocar body 135 to allow air to be pumped into a plurality sheaths 139 located on the interior walls of the inflatable seal 132. In this embodiment, an air hose is coupled to the Luer Lock connection, the air hose is coupled to a pump. When air is pumped into the plurality of sheaths 139 via the air-port 140, the sheaths 139 inflate and expand creating a seal that conforms around the devices inserted in the patient via the trocar 133 of the trocar assembly 102, which prevents loss of pneumoperitoneum.

Figure 19A:
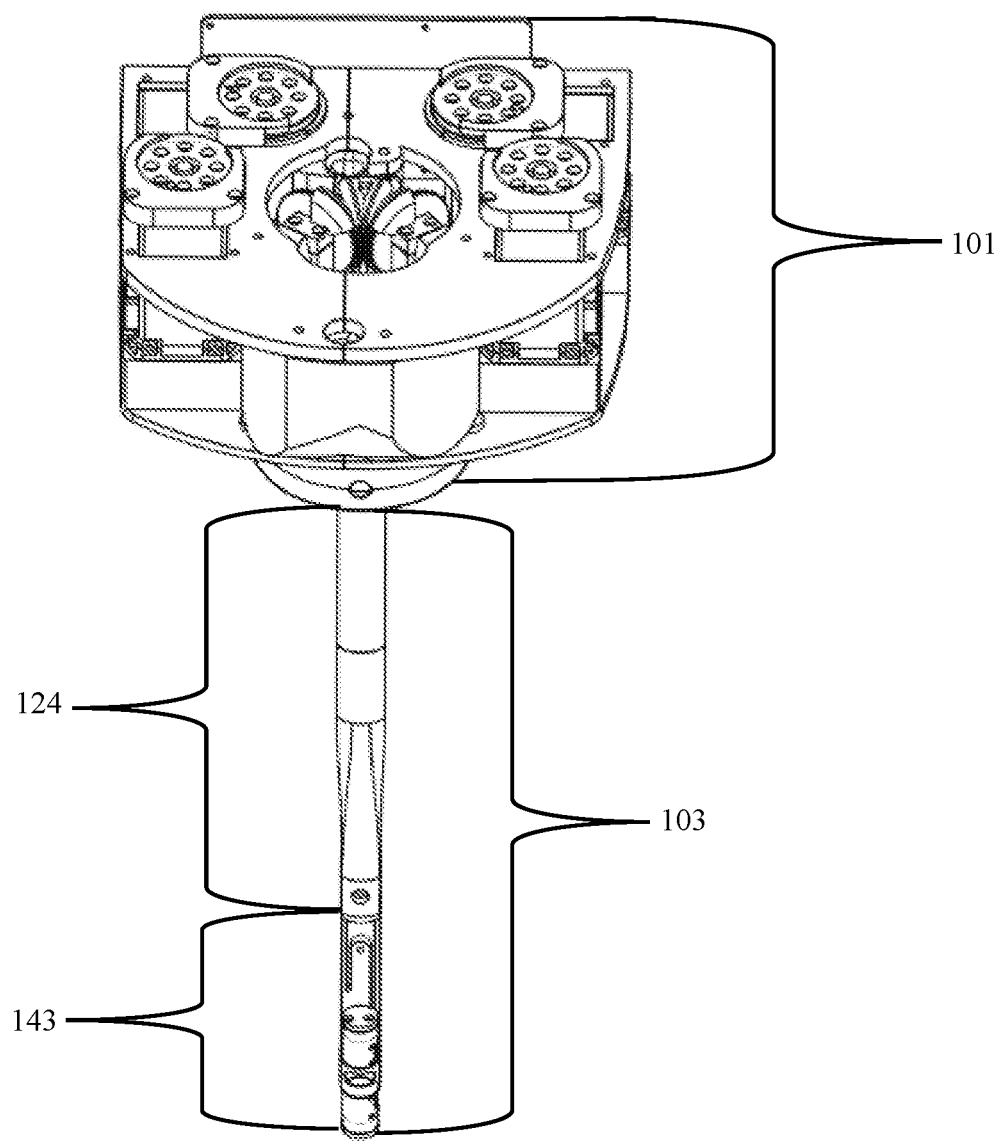
FIG. 19A is a front isometric view of a robotic camera assembly coupled to a camera console assembly according to one embodiment.
Figure 19B:
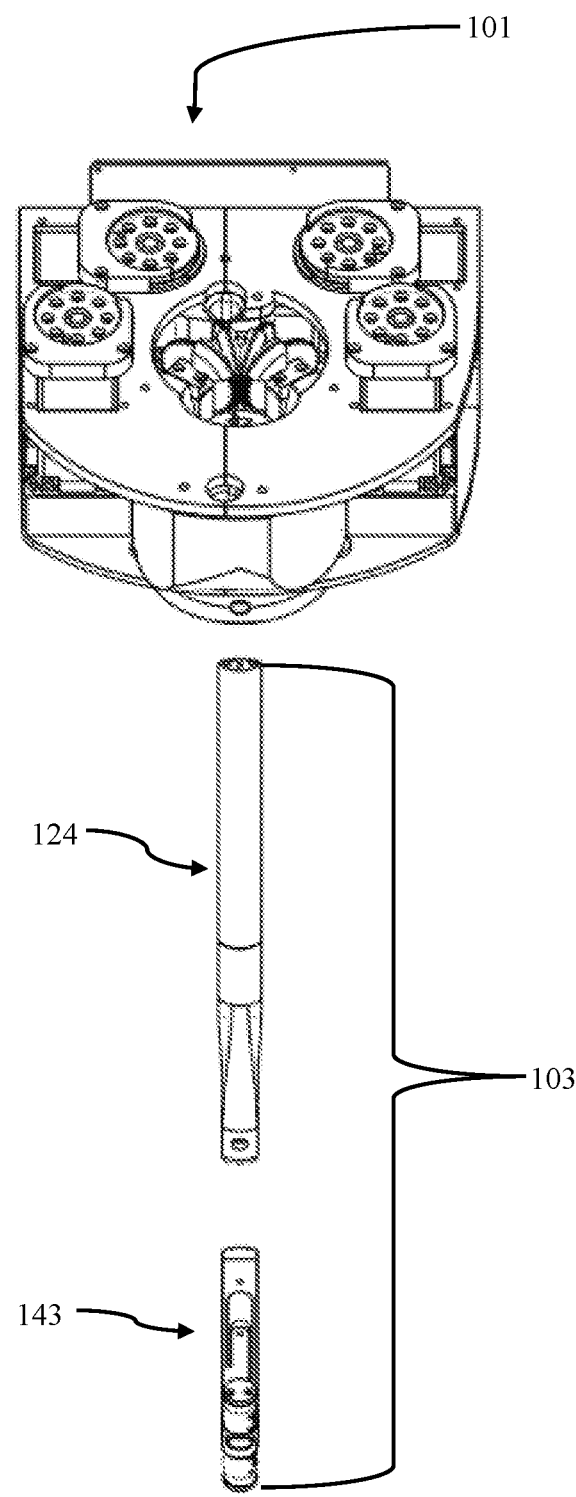
FIG. 19B is a front exploded isometric view of a robotic camera assembly coupled to a camera console assembly according to one embodiment.

In some embodiments, located on the interior of the main trocar body 135 is a seal sub-assembly 138 made up of two seals, the inflatable seal 132 and a universal seal 131. FIGS. 15A-15B show an illustrative embodiment of the seal sub-assembly 138. In one embodiment, the inflatable seal 132 is fabricated to be cylindrical shape, having a proximal and distal end, and a hollow center. FIGS. 19A-19B show an inflatable seal 132 according to one embodiment. In some embodiments, located on interior of the inflatable seal 132 on both sides of said seal are the plurality of sheaths 139. FIGS. 16A-16B show a cross-section of an illustrative embodiment of a seal sub-assembly 138, highlighting the sheaths 139. The plurality of sheaths 139 are affixed to the exterior wall of the seal and extend from the proximal end to the distal end of the seal. Standard attachment methods and techniques known in the art are used to affix the plurality of sheaths 139 to the interior walls of the inflatable seal 132, including but not limited to adhesive connections. In one embodiment, the plurality of sheaths 139 are configured to have two ends, with both ends having o-rings which act as mechanical gaskets.

Additionally, in these embodiments, located on one wall of the inflatable seal 132 is an air-port 140 which protrudes from said wall. The air-port 140 is fabricated to be threaded to allow it to mate with a Luer Lock fitting which passes through the seal port 137 of the main trocar body 135, thus constraining the inflatable seal 132, rotationally and in axial travel. Furthermore, in these embodiments, the air-port 140 is also operatively coupled to the plurality of elastic sheathes 139. In these embodiments, the air-port 140 contains a Luer Lock, so as to allow carbon dioxide ($CO_2$) or air to be pumped into said plurality of sheaths 132. As detailed above, when air is pumped into the plurality of sheaths 139, the sheaths inflate and expand creating a form fitting seal, which conforms to the devices passed through the main trocar body 135, thus preventing gas from escaping the patient's abdomen, while allowing said devices to be manipulated simultaneously. Due to the elasticity of the sheaths 139, multiple devices can pass through and or be routed through the trocar assembly 102 while maintaining a gas tight seal. In various embodiments, the plurality of sheaths 139 can be fabricated out of a variety of materials including but not limited to latex, neoprene, rubber and/or any other materials known in the art, capable of conforming to any shape when inflated. In addition, in further embodiments, the plurality of sheaths 139 are substituted for one elastic sheath that covers the entire interior perimeter of the inflatable seal 132. In alternative embodiments, the air-port located on the inflatable seal is eliminated. In these embodiments, the inflatable seal contains an aperture which aligns with the seal port of the trocar. An air hose is routed directly to a Luer Lock connection which passes through the seal port on the trocar and mates directly with the aperture on the inflatable seal.

In other embodiments, the inflatable seal is replaced by other seals known in art, such as an AirSeal®. In this embodiment, $CO_2$ is continually pumped through a channel in the trocar, creating a pressure differential which prevents loss of pneumoperitoneum during insertion of tools and operation. In alternative embodiments, the inflatable seal is replaced by a compliant material which similarly fills the space of the trocar and conforms to the shapes of tools, devices or other items that are passed through the trocar. In some embodiments, a duckbill seal is utilized, well in further embodiments, a combination of seals known in the art are utilized to prevent loss of pneumoperitoneum during insertion of tools and throughout an operation.

In one embodiment, the proximal end and distal end of the inflatable seal 132 are configured to have threaded ends, so to allow the distal end to mate and couple with the main trocar body 135 and the proximal end to mate and couple with the universal seal 131. In alternative embodiments, different connection methods and attachment methods known in the art are used to couple the inflatable seal 132 to the main trocar body 135, as well as to couple the universal seal 131 with the inflatable seal 132, including but not limited to adhesive connections, snap fit connections, and/or a screw connection.

As illustrated in the embodiment shown in FIGS. 16A-16BD, coupled to the proximal end of the inflatable seal 132 is the universal seal 131. The universal seal 131 is utilized as a secondary seal with the inflatable seal being used as a primary seal. The universal seal 131 is configured to provide an additional layer of sealing to the trocar assembly 102 so as to ensure no insufflation pressure is lost when surgical devices and/or tools are inserted into and extracted from a patient's body, as well as to ensure no insufflation pressure is lost during utilization and actuation of the system. The universal seal is configured to have a hollow center, so as to allow the robotic camera assembly, as well as surgical devices and/or tools to pass through and be inserted into or removed from a patient's body. In one embodiment, the universal seal 131 is configured to be cylindrical shape, with the universal seal 131 containing a distal end and proximal end, with the distal end having a larger diameter than the proximal end. In one embodiment, the universal seal 131 is fabricated as two components, with affix to each other via standard attachment methods and techniques known in the art, including but limited to screw connections, pressed fit connections, snap-fit connections, adhesive connection and/or threaded connections.

In one embodiment, the proximal end of the universal seal 131 is outfitted with a plurality of seal flaps 141 which extend inward from the outer perimeter of the seal to the hollow center of said seal (FIGS. 16A-16B). In one embodiment, the plurality of seal flaps 141 are affixed to the perimeter via an adhesive connection, while in other embodiments, an outer ring is clamped around the outer edge of each of the plurality of flaps 141 via a screw connection. Alternatively, in other embodiments, standard attachment methods and/or techniques known in the art are utilized to affix the seal flaps 141 to the outer perimeter of the universal seal 131, including but not limited to press-fit connections, and/or snap-fit connections.

In some embodiments, the plurality of seal flaps 141 are configured to overlap each other in such a way that allow objects to pass through the hollow center of the universal seal 132, while conforming around the object passed through, such that a seal is created preventing air from escaping the patient's body. In one embodiment, the plurality of seal flaps 141 are fabricated as semi circles, with each one of the plurality of flaps overlapping a portion of another flap. In alternative embodiments, the plurality of seal flaps 141 can be configured to take on any of a variety of shapes, including but not limited to triangles, parallelograms, oval, and/or crescent. Additionally, in various embodiments, the seal flaps 141 are constructed out of variety of materials having flexible and resilient properties, including but not limited to rubber, latex, neoprene, silicone and/or any other materials known in the art, that are flexible and resilient.

As mentioned above, in one embodiment, the universal seal 131 is configured to have a distal end with a larger diameter than its proximal end. In this embodiment, the distal end is configured to have a hollow center with side walls that distally extend, so as to allow the proximal end of the inflatable seal 132 to sit within the distal end of the universal seal 132, such that the side walls of the universal seal 131 encompass the proximal end of the inflatable seal 131. In one embodiment, located on the interior perimeter of the distal end side wall of the universal seal 132 is a groove that is configured to allow an o-ring from the elastic sheaths 139 of the inflatable seal 132 to sit in. In this embodiment, the distal end of the universal seal 131 fits around the proximal end of the inflatable seal 132, with the o-ring from the sheaths 139 entering the groove on the interior wall of the distal end of the universal seal 131, thus creating an interference fit and coupling the universal seal 131 and the inflatable seal 132. In alternative embodiments, standard attachments known in the art are utilized to couple the universal seal 131 and the inflatable seal 132, including but not limited to adhesive connections, threaded connections, press-fits and/or snap-fit connections.

Figures 33A, 33B:
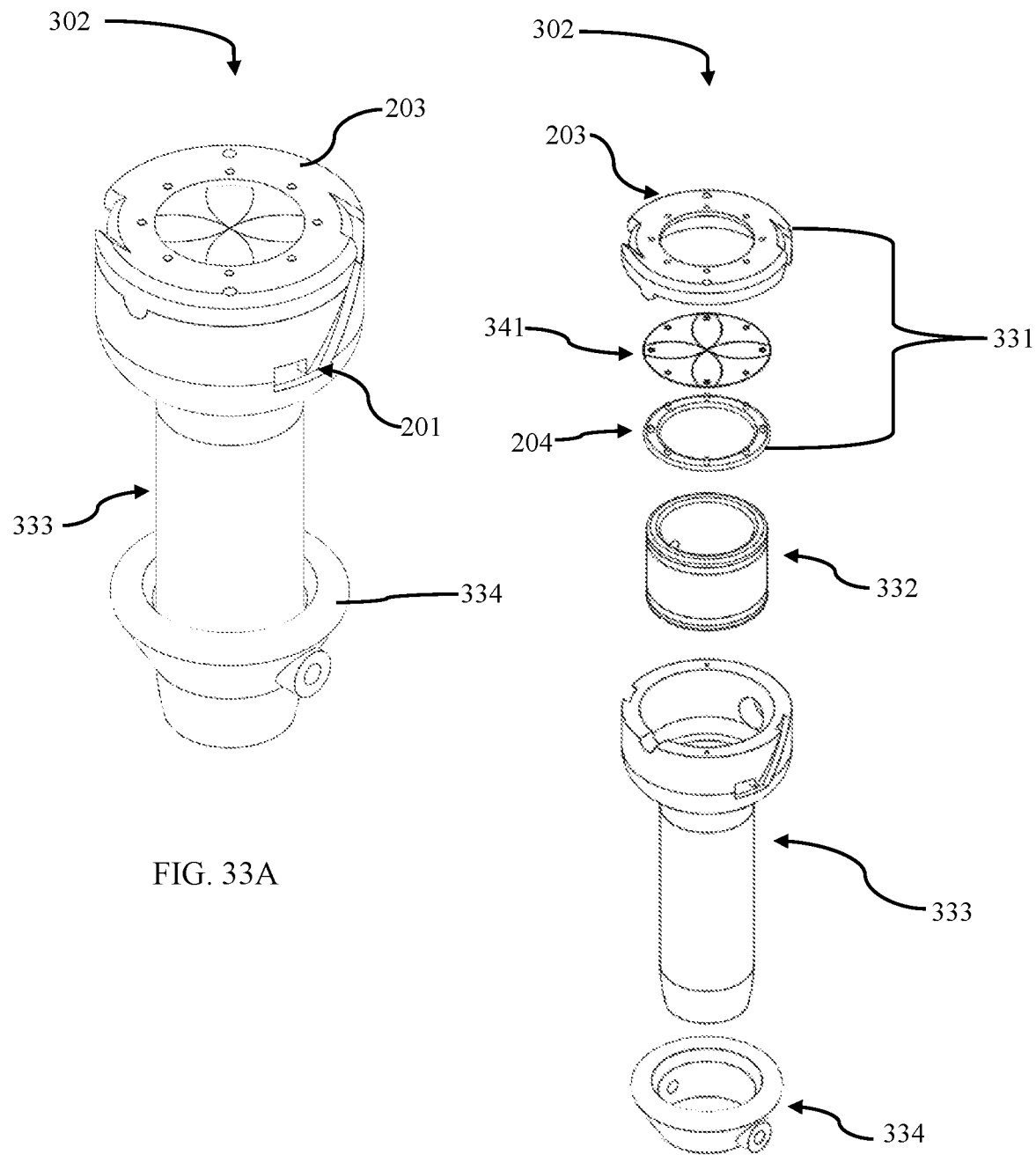
FIG. 33A is an isometric view of a trocar assembly according to one embodiment.
FIG. 33B is an exploded isometric view of a trocar assembly according to one embodiment.

In alternative embodiments, the universal seal can take on various configurations. As depicted in the illustrative embodiment shown in FIG. 33B, in one embodiment, the universal seal 331 contains three components, with the universal seal mating with inflatable seal 332. In this embodiment, universal seal 331 contains a top seal cover 203, seal flaps 341 and a bottom seal cover 204. The seal flaps 341 are coupled between the top seal cover 203 and the bottom seal cover 204. The top seal cover 203 is configured to have a hollow center, and an inner lip, for which the seal flaps 341 and bottom seal cover 204 are fabricated to fit within. In addition, in this embodiment the inflatable seal 332 is also configured to fit within the inner lip of the top seal cover 203. In some embodiments, the top seal cover 203 of universal seal 331 is configured to have an exterior diameter that is the same diameter as the proximal portion of trocar 333, such that the top seal cover couples and mates with trocar 333. In addition, as shown in FIG. 33A in these embodiments, the top seal cover 203 is fabricated to have matching slot connections of trocar 333 to allow a pin to enter and mate the trocar assembly 302 with trocar mating fixture 314 of camera console assembly 301, as detailed above. In one embodiment, the top seal cover 203 couples to trocar 333 via a screw connection, while in other embodiments, different connections known in the are used, including but not limited to adhesive connections or press-fit connections.

Robotic Camera Assembly

As seen in FIG. 19A, in one embodiment of the system, located distal to the camera console assembly 101 is the robotic camera assembly 103. FIG. 19B is an exploded view of the coupling between the robotic camera assembly 103 and the camera console assembly 101 according to one embodiment. The robotic camera assembly 103 is configured to provide the surgeon with live camera feed of an operation site, as well as enable a surgeon to actuate and control a stereoscopic camera 143, thus allowing a surgeon to obtain multiple views of an operation site. As further detailed below, in one embodiment, the surgeon controls the movement of the stereoscopic camera 143 based on the movement of the surgeon's head, thus enabling the surgeon to obtain a desired view of an operation site in an intuitive and natural manner.

As mentioned above, in one embodiment, the robotic camera assembly 103 is coupled to the camera console assembly 101 via the camera support tube 124 (FIG. 19B). The camera support tube 124 is configured to have a distal end and a proximal end, with the proximal end coupled to the camera console assembly 101 and the distal end coupled to the stereoscopic camera 143. In addition to supporting the stereoscopic camera and coupling the robotic camera assembly 103 to the camera console assembly 101, the camera support tube 124 is also configured to route and protect cables and electrical communication components from the robotic camera assembly 103 to the camera console assembly 101, such that the cables and electrical communication components are not damaged during insertion and actuation of the system, as well as when other devices are inserted into the patient's body via the trocar assembly 102.

In one embodiment, the camera support tube 124 equipped with a plurality of channels and/or grooves, which are configured to allow cables to sit within, so as to provide a track for said cables to be routed to the camera console assembly 101, as well as protect said cables during actuation of the system. In alternative embodiments, the camera support tube is outfitted with lumens for which cables are routed through. In addition, in one embodiment, the camera support tube 124 contains grooves and/or corrugation configured to route electronic communication components from a stereoscopic camera to a camera console assembly. In alternative embodiments, grooves and/or corrugation are located on the side of the camera support tube 124 such as to allow electronic communication components to sit flush with the support tube so as to prevent the electronic communication components from bending and becoming damaged.

In one embodiment, the camera support tube 124 couples to pulley housing block 112 of the camera console assembly 101 via a screw connection, while in other embodiments standard coupling methods and techniques known in the art are utilized, including but not limited to snap-fit connections, pressed fit connections, adhesive connection, and/or welded connection. The camera support tube 124 is configured to fit and pass through the trocar assembly 102 so as allow the robotic camera assembly 103 to be inserted into a patient's body.

In some embodiments, the camera support tube 124 is configured to have a vertical offset so as to allow a stereoscopic camera to not interfere with other instruments or devices being inserted through the trocar assembly 102. In these embodiments, the proximal portion of the camera support tube that remains in the trocar assembly has a small cross-sectional area to allow other instruments and/or devices to pass through the trocar and into the field of operation. The distal end of the camera support tube has a vertical offset such that when inside the field of operation, the distal end of the camera support tube is jogged upward, so as to allow the stereoscopic camera to remain elevated above the space allowed for other instruments and/or devices to enter and pass through the trocar assembly and into the field of operation. In other embodiments, the distal end of the camera support tube is fabricated to have a horizontal offset or angular offset, while in further embodiments the camera support tube is fabricated to have a horizontal and vertical offset.

Figure 21A:
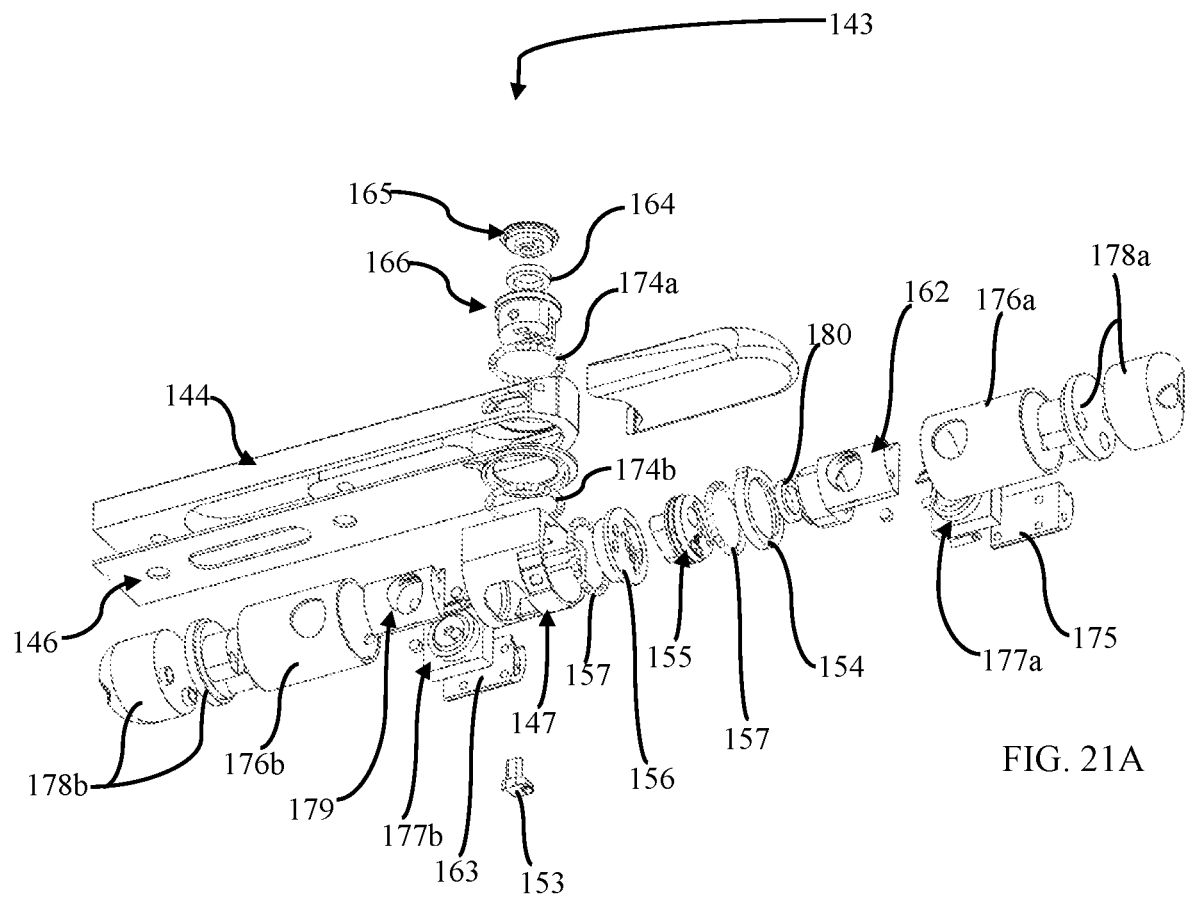
FIG. 21A is an exploded isometric view of a stereoscopic camera according to one embodiment.
Figure 21B:
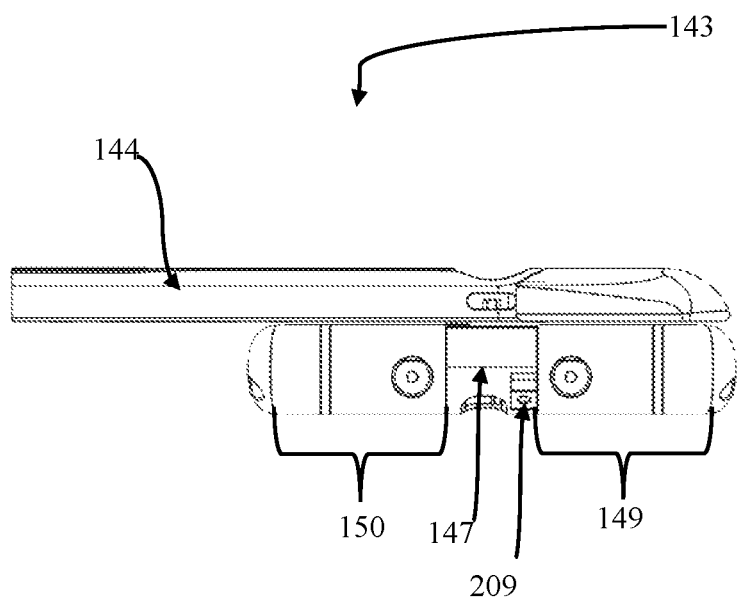
FIG. 21B is a front isometric view of a stereoscopic camera according to one embodiment.

As mentioned above, in one embodiment operatively coupled to the distal end of the camera support tube 124 is the stereoscopic camera 143 (FIG. 21B). FIG. 21A shows an exploded isometric view of an illustrative embodiment of a stereoscopic camera 143. The stereoscopic camera 143 is utilized to provide a surgeon with live stereoscopic camera feeds of the operation site during an operation. The stereoscopic camera 143 is configured to enter and pass through a trocar assembly and enter the patient's body. In some embodiments, the stereoscopic camera has an actuation system which has a pitch actuation assembly and a yaw actuation assembly, two camera assemblies having camera modules or camera module assemblies, among other components as further detailed below.

Figure 24A:
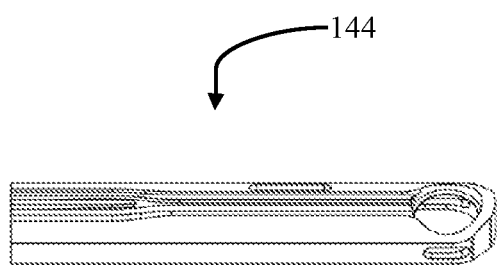
FIG. 24A is a top isometric view of a main camera body according to one embodiment.
Figure 24B:
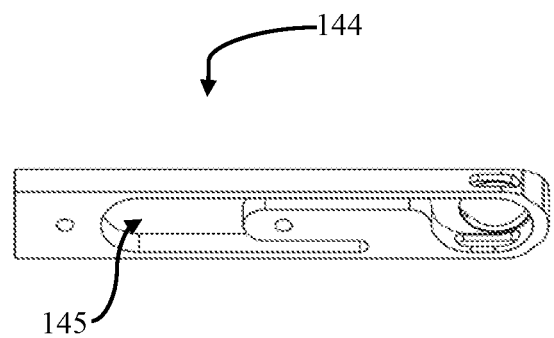
FIG. 24B is a bottom isometric view of a main camera body according to one embodiment.
Figure 25A:
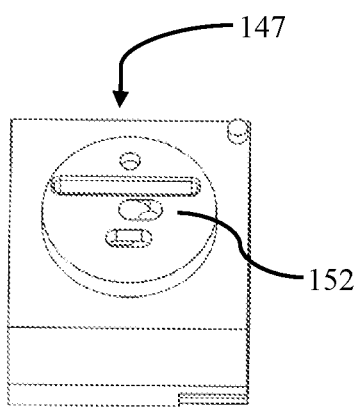
FIG. 25A is a top isometric view of a main camera body mount according to one embodiment.
Figure 25B:
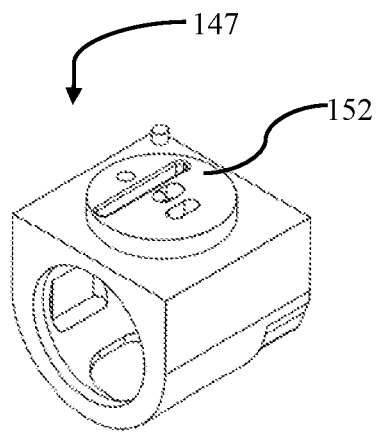
FIG. 25B is an isometric view of a main camera body mount according to one embodiment.
Figure 25C:
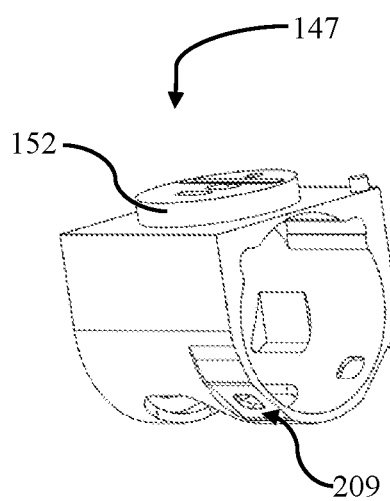
FIG. 25C is an additional isometric view of a main camera body mount according to one embodiment.

In one embodiment, the stereoscopic camera 143 contains a main camera body 144, which is used to couple and mate the stereoscopic camera 143 with the camera support tube 124. FIGS. 24A-24B show multiple views of an illustrative embodiment of a main camera body 144. In one embodiment, the main camera body 144 is also utilized as a support for the stereoscopic camera 143 and its components. In addition, in some embodiments the main camera body 144 is configured to hold and redirect electrical communication components, and cables from the stereoscopic camera 143 to the camera support tube 124. In one embodiment, located on the top surface of the main camera body 144 are grooves and/or channels, which are used to route cables from the stereoscopic camera 143 to the camera support tube 124. Additionally, in one embodiment, the main camera body 144 contains an electrical communication component cavity 145, where the electrical communication components sit in. In one embodiment, the electrical communication component cavity 145 is configured to allow electrical communication components to move within the pocket, such that during actuation of the stereoscopic camera 143 the electronic communication components have space to move and extend so that the components do not bend and/or crease in such a way that they become damaged.

Figure 34A:
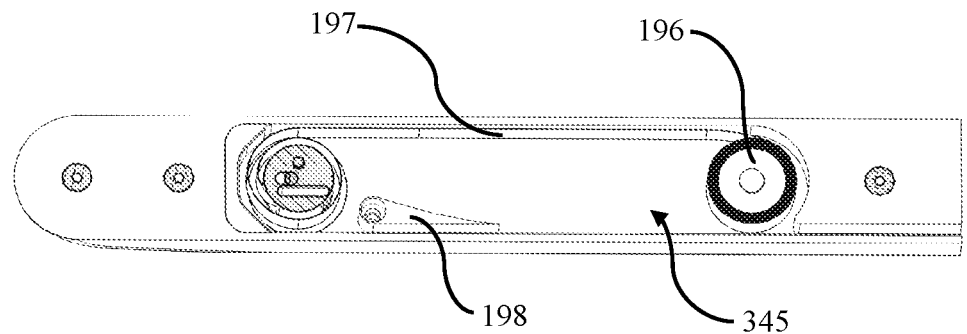
FIG. 34A is an isometric view of an electrical communication component cavity according to one embodiment.
Figure 34B:
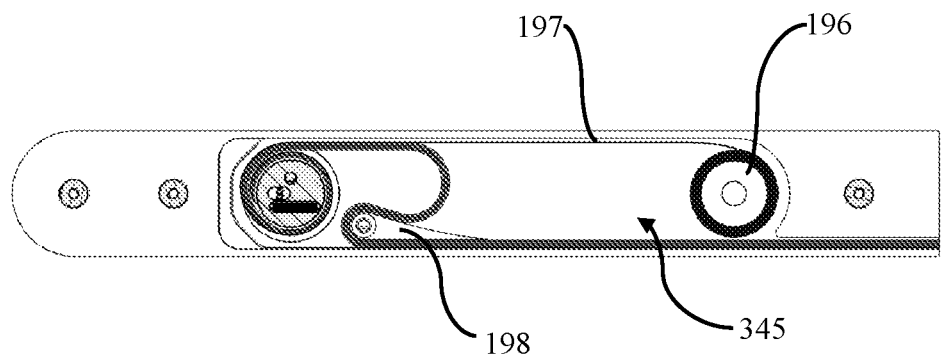
FIG. 34B is an isometric view of an electrical communication component cavity according to one embodiment.

As seen in FIGS. 34A-34B, in one embodiment electrical communication component cavity 345, is outfitted with a flex wrap guide 198 and a constant-force spring 197 for routing electrical communication components. In these embodiments, the electrical communication components are routed through the yaw pulley block 166 and around the protrusion 171 of said yaw pulley block 166 in the same manner as detailed below. As illustrated in FIG. 34B, in one embodiment, after wrapping around the yaw pulley block, the electrical communication components are routed around the flex wrap guide 198, leaving a portion of the electrical communication component free to move during yaw actuation, so as to allow the electrical communication components to extend into the electrical communication component cavity 345 or be reeled back around the yaw pulley block depending on the direction of actuation of the stereoscopic camera about the yaw axis. In these embodiments, one end of the constant-force spring 197 is coupled to the protrusion of the yaw pulley block 166, and the other end of the constant-force spring 197 is wrapped around a spring spool 196 (FIG. 34A). The spring spool 196 sits on a pin located on the electrical communication component cavity, for which the spring spool rotates about. The constant-force spring 197 follows the electrical communication component as it is wrapped around the yaw pulley block, such that the electrical communication component is encompassed by the constant-force spring. The constant-force spring 197 is configured to apply an inward radial force on the electrical communication component, in order to prevent said communication component from kinking or jamming within the space around the yaw pulley block said component is wrapped around, during actuation of the stereoscopic camera about the yaw axis.

In one embodiment affixed to the top surface of the main camera body 144 is a main body flex cover 146 (FIG. 19A). The main body flex cover 146 is configured to provide an additional layer of protection for the electrical communication components situated in the electrical communication component cavity 145, as well as provide a bearing surface on which a main camera body mount 147 couples and mates to. In one embodiment, the main body flex cover 147 is coupled to the main camera body, via a screw connection, while in other embodiments standard coupling and attachment methods known in the art are used, including but not limited to snap-fit connections, adhesive connections, and/or press-fit connections.

Figure 27:
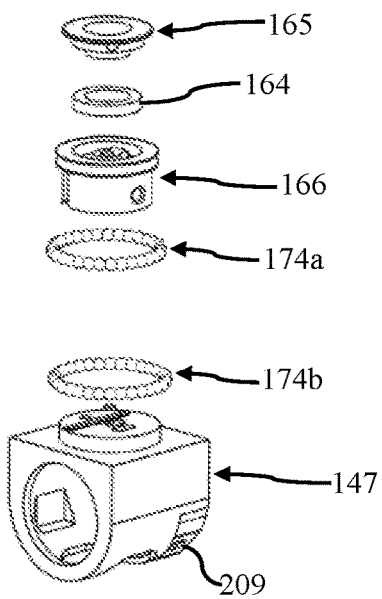
FIG. 27 is an exploded isometric view of the connection between a main camera body mount and a yaw actuation assembly, according to one embodiment.

As mentioned above, in one embodiment, the main camera flex cover 146 provides a bearing surface for which the main camera body mount 147 can rotate. FIGS. 25A-25D show multiple views of an illustrative embodiment of a main camera body mount 147. The main camera body mount 147 functions as a housing for a pitch actuation assembly 148 (FIGS. 22A-22C), of the stereoscopic camera 143, for which a left camera assembly 149 and a right camera assembly 150 couple to. In addition, the main camera body mount 147 is also utilized to connect the main camera body 144 with the stereoscopic camera 143. Furthermore, in one embodiment the main camera body mount 147 also provides a connection point for a yaw actuation assembly 151 (FIG. 27), of the robotic camera assembly 103. In one embodiment, located on the top surface of the main camera body mount 147 is a yaw bearing protrusion 152, which forms a bearing race for ball bearings to sit and ride along. In addition, in one embodiment, the top surface of the main camera body mount 147 contains a mechanical stop to prevent the stereoscopic camera 143 from rotating and being actuated past its allowable actuation range, as well as to prevent electrical communication components that are routed through the main camera body mount 147 from being damaged during actuation.

In one embodiment, the main camera body mount 147 is configured to have a hollow center, so as to allow pitch rotation of the left camera assembly 149 and the right camera assembly 150. In addition, in one embodiment the main camera body mount 147 contains a plurality of apertures with one aperture utilized to connect a main mount insert 153, one aperture utilized to route cables from the pitch actuation assembly 148, one aperture utilized as an alignment pinhole to align the left camera assembly 149 and the right camera assembly 150, and one aperture is used to route electrical communication components through the main camera body mount 144. In one embodiment, the main camera body mount 147 contains machined surfaced apertures, for which rotational positional sensors 209 and capacitors to sit inside, so as allow electrical communication components operatively coupled to said rotational positional sensors 209 and capacitors to sit flat against the outer surface of the main camera body mount 147 (FIG. 21B and FIG. 25C) and thus prevent any damage to the electrical communication components during actuation of the stereoscopic camera 143. In one embodiment, the rotational positional sensors are positioned orthogonally to one another, with said sensors being centered to the axis of pitch rotation. In one embodiment, two rotational positional sensors are coupled to the main camera body mount 147, while in other embodiments three or more rotational positional sensors are coupled to the main camera body mount. The rotational positional sensors are used to obtain position and orientation data of the stereoscopic camera, with said data being transmitted by electrical communication components to external computers. In various embodiments, different types of position and orientation sensors are utilized, including but not limited to, hall effect sensors and capacitors, gyroscopes, accelerometers, and/or optical encoders.

In addition, in one embodiment the main camera body mount 147 contains a pocket for which the main mount insert 153 enters and couples to. In one embodiment, the pocket is fabricated such that the main mount insert 153 couples to the main camera body mount 144 and prevents the main camera body mount 144 from moving and becoming detached from the rest of the robotic camera assembly during actuation. The main mount insert 153 is discussed in further detail below. Additionally, in one embodiment, located on the interior wall of the main camera body mount 147 are keyed grooves, that are constructed to constrain the rotation of a pitch bearing race 154.

In a different embodiment, the main camera body mount is fabricated as multiple components that couple to each other, in order to provide ease of assembly and repair of the pitch actuation assembly 148. As depicted in the illustrative embodiment shown in FIGS. 35A-35B, in one embodiment main camera body mount 347 contains a main mount 181, a main mount cover 182 and a main mount strap 183. In addition to providing a housing for the pitch actuation assembly 148, in this embodiment, the main camera body mount 347 is also utilized to connect the main camera body 144 with the camera assemblies of the stereoscopic camera 143. As depicted in FIG. 35B, located on the top surface of the main mount 181 is a yaw bearing protrusion 352, which forms a bearing race for yaw ball bearings to sit and ride along.

In addition, in some embodiments the main mount 181 contains a mechanical stop to prevent the camera assemblies from being actuated and rotated past its allowable actuation range. In one embodiment, the mechanical stop is configured as two concentric rings, with one being an inner ring fixed to the main body flex cover, and one being an outer ring which rotates concentrically and is located on the main mount. In this embodiment, both concentric rings contain radial protrusions, with the protrusion located on the inner ring extending radially outward and the protrusion on the outer rig extending radially inward, such that those protrusions do not interfere with each other directly. The inner and outer concentric rings are spaced apart such that they form a track in which a bearing ball is free to move. The track formed is configured to be slightly larger than the bearing ball but constrains the bearing ball along a circular path. During actuation of the camera assemblies about the yaw axis, the protrusion on the outer ring contacts the ball bearing and free rotates until the ball bearing contacts and jams against the protrusion on the inner ring. In different embodiments the location of the protrusions can be adjusted to configure the start and stop of rotation, while in other embodiments the width of the protrusions can be configured to achieve a desired amount of rotation. The amount of rotation achievable can range from 0 degrees of rotation all the way to 700 degrees of rotation depending on the configuration and location of the protrusions on the concentric rings. In other embodiments, the mechanical stop is configured to have three concentric rings and two bearing balls, thus allow for a greater range of rotation to be achieved.

In addition, in some embodiments the main mount contains a plurality of apertures for routing cables from the pitch actuation assembly and electrical communication components from the camera assemblies. Additionally, on the interior surface of the main mount 181 are machined surface apertures for which rotational positional sensors and capacitors sit in. In some embodiments, the rotational positional sensors used are two hall effect sensors and capacitors, which sit within the interior surface of the main mount, while in further embodiments more than two hall effect sensors and capacitors sit within the interior surface of the main mount. In addition, on the interior of the main mount 181 are machined surfaces for the pitch bearing races of the pitch actuation assembly to sit in.

Similar to the main mount 181, in some embodiments, located on the interior surface of the main mount cover 182 are machined surfaces for rotational positional sensors and capacitors to sit within, as well as corresponding machined surfaces for pitch bearing races from the pitch actuation assembly to sit in (FIG. 35A and FIG. 35B). In these embodiments, the main mount 181 and the main mount cover 182 couple to each other via the main mount strap 183. The main mount strap 183 is fabricated to couple the main mount 181 and the main mount cover 182 so that the main mount and the main mount cover stay fixed relative to each other, as well as to prevent debris and fluids from entering.

As mentioned above, in one embodiment, the main camera body mount is configured to house the pitch actuation assembly. FIGS. 22A-22C show multiple views of a pitch actuation assembly 148 according to one embodiment. The pitch actuation assembly 148 is configured to actuate and rotate the stereoscopic camera 143 in a pitch axis of rotation, such as to allow a surgeon to obtain additional views of the operation site. In one embodiment, the pitch actuation assembly 148 contains a pitch pulley 155, a pitch thrust bearing 156, the pitch bearing race 154, a plurality of pitch ball bearings 157a and a plurality of pitch ball bearings 157b.

Figure 23A:
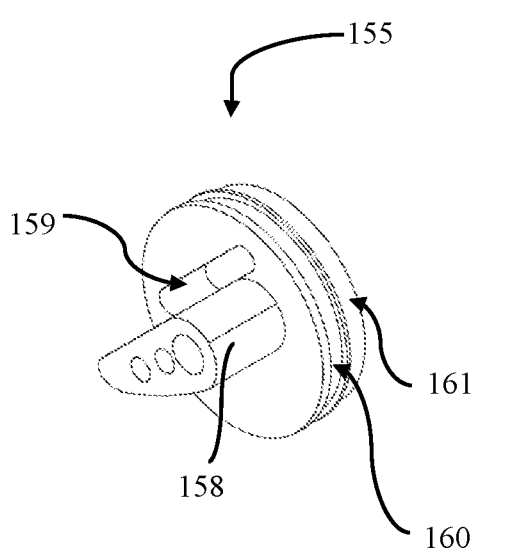
FIG. 23A is an isometric view of the right side of a pitch pulley according to one embodiment.
Figure 23B:
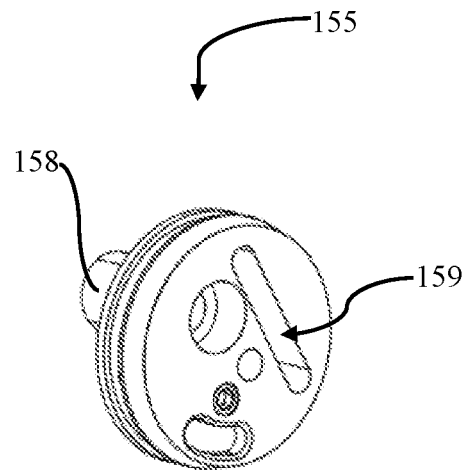
FIG. 23B is an isometric view of the left side of a pitch pulley according to one embodiment.
Figure 23C:
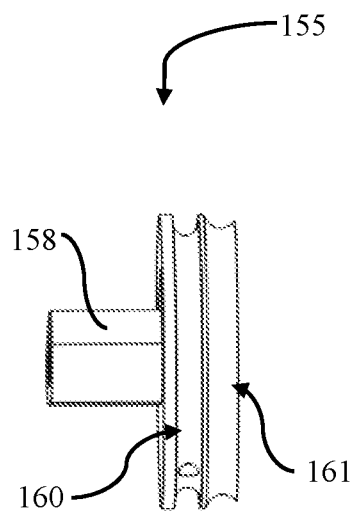
FIG. 23C is a front isometric view of a pitch pulley according to one embodiment.

FIGS. 23A-23C show multiple views of a pitch pulley 155 according to one embodiment. In one embodiment, the pitch pulley 155 is configured to provide a surface for electrical communication components to run around when the stereoscopic camera 143 is actuated in the pitch direction. In addition, the pitch pulley 155 is configured to actuate the stereoscopic camera 143 in the pitch direction, via cables that are routed from the pitch actuation assembly 148 to the actuators 106 of the camera console assembly 101. Furthermore, the pitch pulley 155 is configured to act as a stabilizer during pitch actuation of the stereoscopic camera 143 such that both the left camera assembly 149 and the right camera assembly 150 rotate along the pitch axis in a consistent manner by constraining the rotation of both camera assemblies along the axis.

In one embodiment, the pitch pulley 155 contains a pitch pulley mandrel 158 (FIG. 23C), configured to allow electrical communication components to wrap around during actuation of the stereoscopic camera. In one embodiment, the pitch pulley mandrel 158 is fabricated to allow the electrical communication components to lay flat as they exit a flex slot 159 located on the front surface of the pitch pulley 155. In addition, in this embodiment, the pitch pulley mandrel 158 is fabricated to enable electrical communication components to wrap around the mandrel and stack up as they are wrapped around so as to prevent said communication components from being damaged during actuation. In one embodiment, the pitch pulley mandrel 158 is fabricated to be oblong in shape, with said mandrel having a wider diameter on the top and a smaller diameter on the bottom. In alternative embodiments, the pitch pulley mandrel 158 can take on a variety of shapes and configurations, that allow electrical communication components to wrap around in a concise manner to prevent damage to said communication components. In these embodiments, the pitch pulley mandrel 158 can be configured to be triangular in shape with rounded edges, semi-circular in shape, and/or any other polygon with rounded edges.

In one embodiment, located on the exterior of the pitch pulley mandrel 158 are two apertures, in which alignment pins sit in. In this embodiment, the alignment pins are used to align the pitch pulley 155 with the pitch thrust bearing 156. In one embodiment, the pitch pulley 155 couples and mates with the pitch thrust bearing 156 via a screw connection, with the screw sitting in an aperture located on the pitch pulley mandrel 158. In other embodiments, different coupling methods known in the art are used to mate and couple the pitch pulley 155 with the pitch thrust bearing 156 including but not limited to press-fit connections, snap fit connections, and/or adhesive connections.

In addition, in one embodiment the pitch pulley 155 contains a pitch cable channel 160 for which a cable is routed around. In one embodiment located on the interior of the pitch cable channel 160 is an aperture, with said aperture crossing through the center plane of the pitch pulley 155. In this embodiment, a cable is routed around the pitch pulley 155, where it enters the aperture, and passes through to the other side of the pitch pulley 155 and is routed through the main camera body 144. In this embodiment, the cable sits within the pitch cable channel 160 until it is routed through the aperture in the pitch cable channel 160, once the cable passes through the aperture on the other side of the pulley, a set screw holds the cable in place within the aperture, thus preventing the cable from moving during actuation. In one embodiment, one end of the cable is routed to one of the actuators 106 of the camera console assembly 101 and the other end is routed to a different actuator 106. In this embodiment, one of the actuators 106 is configured to actuate the pitch pulley 155 in an upward direction about a pitch axis, and another one of the actuators 106 is configured to actuate the pitch pulley 155 in the downward direction about a pitch axis. In other embodiments, both ends of the cable may be routed to only one actuator 106, with that actuator configured to actuate the pitch pulley 155 in both the upward and downward direction about a pitch axis. In addition, in alternative embodiments, two or more cables may be used to actuate the pitch pulley 155. Additionally, in some embodiment, the pitch pulley 155 also contains a bearing surface 161, with said bearing surface fabricated to allow the pitch ball bearings 157a to sit in.

As mentioned above, in some embodiments, contained in the pitch actuation assembly 148 is the pitch bearing race 154 (FIG. 22C). The pitch bearing race 154 is configured to have a smooth surface for the pitch ball bearings 157a ride along during actuation, as well as to constrain the pitch ball bearings 157a so that they maintain contact with the bearing surface of the pitch pulley and the pitch bearing race 154. In one embodiment, the pitch bearing race 154 is fabricated to have two protrusions that mate and couple with grooves located on the interior of the main camera body mount 147, in order to constrain the rotation of the pitch bearing race 154 during actuation. The protrusions are fabricated to mate with grooves located on the interior of the main camera body mount 147, thus in different embodiments the protrusions can take on any shape that allow them to sit and mate with the grooves contained on the interior of the main camera body mount 147. In one embodiment, the pitch bearing race 154 is fabricated to have only one protrusion, while in other embodiments the pitch bearing race 154 may be configured to have two or more protrusions. In alternative embodiments, the protrusions are eliminated and the pitch bearing race 154 is constrained by friction.

As mentioned above, in some embodiments, contained in the pitch actuation assembly 148 is the pitch thrust bearing 156. The pitch thrust bearing 156 is configured to act as a rotational bearing for pitch of the left camera assembly 149 and the right camera assembly 150, and as a thrust bearing to compensate for an axial force acting upon the robotic camera assembly 103 during actuation. The pitch thrust bearing 156 rotates inside of the main camera body mount 147 and mates with the pitch pulley 155. In one embodiment, the pitch thrust bearing 156 contains a bearing surface for which the pitch ball bearings 157b sit on. In this embodiment, the pitch ball bearings 157b sit on the bearing surface of the pitch thrust bearing 156 and a machined bearing race located in the interior of the main camera body mount 147.

In one embodiment, the pitch thrust bearing 156 contains a plurality of apertures, with two being used to mate and couple the pitch thrust bearing 156 to a front left camera support 162, one being used to align the pitch thrust bearing 156 with the pitch pulley 155, one to route electrical communication components through the pitch actuation assembly 148, two apertures for aligning the left camera assembly 149 and the right camera assembly 150 to a desired position and orientation, and one aperture to connect the left camera assembly 149 and the right camera assembly 150. In one embodiment, the pitch thrust bearing 156 contains a notch for aligning a back right camera support 163 of the right camera assembly 150.

Figure 38A:
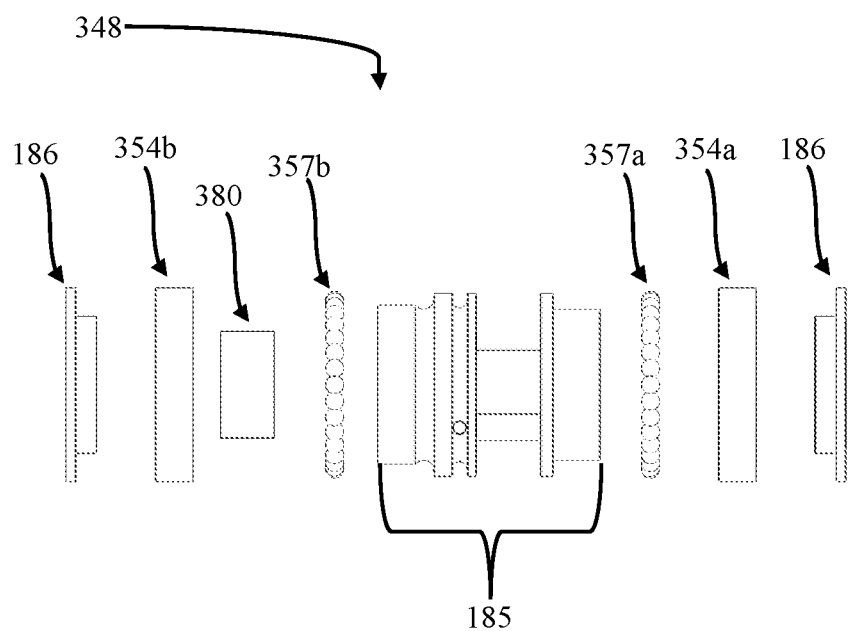
FIG. 38A is a profile view of a pitch actuation assembly according to one embodiment.
Figure 38B:
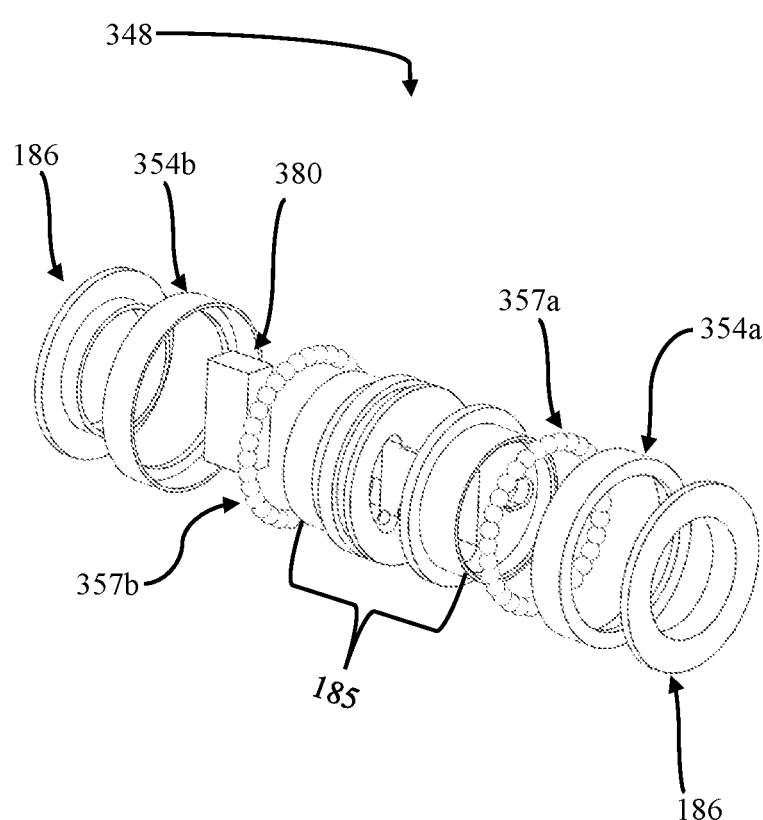
FIG. 38B is an isometric view of a pitch actuation assembly according to one embodiment.

In other embodiments, the pitch actuation assembly can take on different configurations. FIGS. 38A-38B shows an illustrative embodiment of pitch actuation assembly 348. As depicted in FIGS. 38A-38B, in one embodiment, the pitch pulley and pitch thrust bearing are fabricated as one piece creating a pitch actuation body 185. In this embodiment, the pitch actuation body 185 provides the same functions detailed above for the pitch pulley and pitch thrust bearing, while allowing for ease of assembly and improved alignment. In this embodiment, pitch ball bearings 357b ride along a pitch bearing race 354b and a surface of the pitch actuation body 185 instead of the bearing surface of the main camera body mount. Additionally, in this embodiment, the pitch actuation assembly 348 contains a pitch assembly ring 186, which acts as an enclosure retaining pitch ball bearings 357b and the pitch bearing race 354b. Furthermore, in this embodiment pitch ball bearings 357a ride along pitch bearing race 354a and a surface of the pitch actuation body 185. In addition, this embodiment contains an additional pitch assembly ring 186 which acts as an enclosure, retaining pitch ball bearings 357a and the pitch bearing race 354a. Additionally, in this embodiment a pitch magnet 380 is located within the pitch actuation assembly 348, as depicted in FIG. 38A.

In alternative embodiments, the pitch actuation assembly is fabricated to be directly driven by an actuator. In these embodiments, the actuator replaces the cable pulley systems detailed above. Different types of actuators can be utilized in different embodiments, including but not limited to, piezoelectric motors, linear actuators, rotational motors such as servo motors or stepper motors, or other known actuators in the field. In these embodiments, the actuators provide the rotational movement for the stereoscopic camera about a pitch axis.

In alternative embodiments, pitch actuation of a stereoscopic camera is done by rotating the camera support tube about a pitch axis located at the proximal end of the camera support tube. In these embodiments, an actuator may be affixed to the proximal end of the camera support tube for rotating said support tube about the pitch axis. In different embodiments, different types of actuators can be utilized including but not limited to, piezoelectric motors, linear actuators, rotational motors such as servomotors or stepper motors, and/or other actuators known in the field capable of providing rotational movement. Alternatively, in some embodiments, the camera support tube is manually rotated about a pitch axis.

In further embodiments, the camera support tube is outfitted with an actuator located at the distal end of the support tube, which rotates the main camera body about a pitch axis. In these embodiments, the pitch actuation assembly of the stereoscopic camera may be eliminated or may be used in conjunction with the above-mentioned actuation methods. In different embodiments, different types of actuators can be utilized including but not limited to, piezoelectric motors, linear actuators, rotational motors such as servomotors or stepper motors, and/or other actuators known in the field capable of providing rotational movement.

As previously mentioned, in one embodiment, the main camera body mount 147 is coupled to the main camera body 144 via the main mount insert 153. In one embodiment, the main mount insert 153 is configured to connect the main camera body mount 147 and the yaw actuation assembly 151. In one embodiment, the main mount insert 153 contains an aperture on the bottom surface that has filleted sides to allow for cable(s) to move across the surface without said cable(s) becoming damaged. In addition, in some embodiments, the bottom surface of the main mount insert 153 is fabricated to be curved in shape to match the bore of the main camera body mount 147, such that the main mount insert 153 sits flush with the main camera body mount 147. Additionally, in some embodiments, the main mount insert 153 contains a stem which mates with and sits inside a slot in the yaw actuation assembly 151. In these embodiments, the stem of the main mount inserts 153 passes through the main camera body mount 147 and mates with the yaw actuation assembly 151.

Figure 26A:
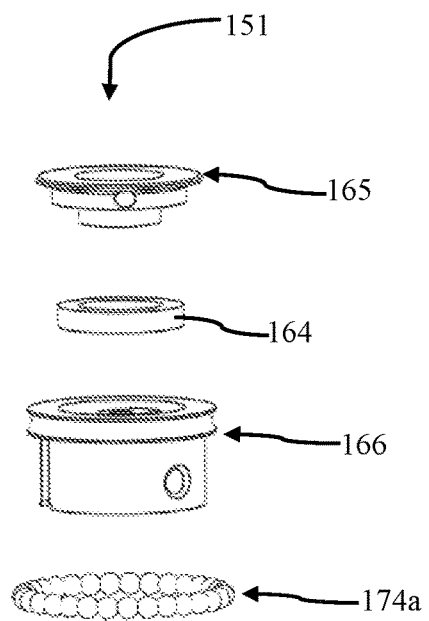
FIG. 26A is an exploded isometric view of a yaw actuation assembly according to one embodiment.
Figure 26B:
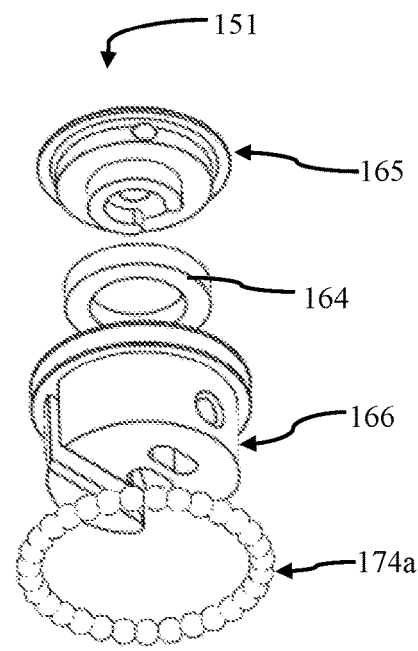
FIG. 26B is an additional exploded isometric view of a yaw actuation assembly according to one embodiment.

FIGS. 26A-26B show multiple views of a yaw actuation assembly 151 according to one embodiment. The yaw actuation assembly is configured to provide yaw rotational movement of the stereoscopic camera or stereoscopic camera assembly 143, about a yaw axis. The yaw actuation assembly provides an added degree of freedom to the stereoscopic camera 143, thus allowing a surgeon to obtain a wider field of view of the operation site. In one embodiment, the yaw actuation assembly 151 is fabricated to contain a yaw magnet 164, a yaw pulley 165 yaw pulley block 166, and two sets of yaw ball bearings 174a and 174b with all of the parts coupling and mating together to create the yaw actuation assembly 151.

Figure 28A:
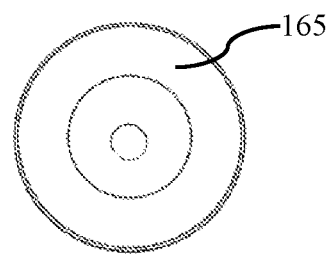
FIG. 28A is a top profile view of a yaw pulley according to one embodiment.
Figure 28B:
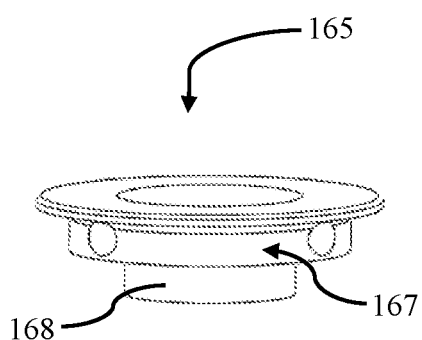
FIG. 28B is a side isometric view of a yaw pulley according to one embodiment.
Figure 28C:
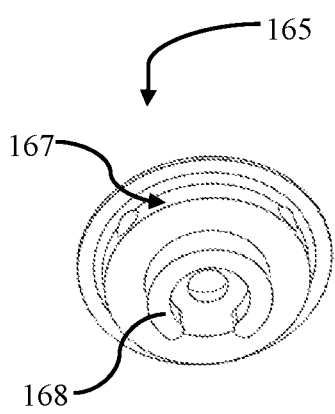
FIG. 28C is a bottom isometric view of a yaw pulley according to one embodiment.

FIGS. 28A-28C show multiple views of a yaw pulley according to one embodiment. In one embodiment, the yaw pulley 165, is configured to be the shape of a flanged cylinder, containing an aperture with fillet sides, with said aperture passing through the center of the cylinder so as to allow cables to pass through without damaging said cables. In addition, in one embodiment the yaw pulley 165 contains a yaw cable surface 167 for which cable(s) are routed along.

In one embodiment, perpendicular to the yaw cable surface 167 is an opening for which cable(s) are a routed through (FIG. 28B). In this embodiment, one end of a cable is routed around the yaw cable surface 167 once in a first direction, with the other end of said cable routed around the yaw cable surface 167 in a second direction which is opposite the first direction. In this embodiment, once both ends of the cable have been routed around the yaw cable surface 167 in their respective directions, each end of the cable is routed to one of the actuators 106 of the camera console assembly 101, with each end being routed to a separate actuator 106. In this embodiment, one actuator 106 is used to rotate the stereoscopic camera 143 in a first yaw direction, and one actuator 106 is used to rotate the stereoscopic camera 143 in a second yaw direction. In alternative embodiments, both ends of the cable may be routed to only one actuator 106, with said actuator 106 being configured to rotate the stereoscopic camera 143 in both a first and second yaw direction.

In one embodiment, located beneath the yaw cable surface 167 of the yaw pulley 165 is a connection boss 168 that is machined in the shape of a horseshoe. In this embodiment, the connection boss 168 is configured so that it can only mate with the yaw pulley block 166 in one orientation. In different embodiments, the connection boss 168 is fabricated to take on a variety of shapes that allow it to mate with the yaw pulley block 166 in only one orientation, including but not limited to hexagonal shape and/or any polygon. In alternative embodiments, two connection bosses 168 are used to connect the yaw pulley 165 with the yaw pulley block 166. In addition, in other embodiments, different connections known in the field are used to connect the yaw pulley 165 with the yaw pulley block 166, including but not limited to, a pin and slot connection, a screw connection, and/or a snap-fit connection. In addition, in some embodiments, the connection boss 168 is located on the yaw pulley block instead of the yaw pulley.

Figure 29A:
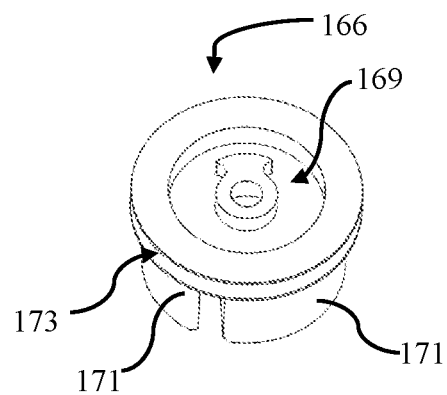
FIG. 29A is a top isometric view of a yaw pulley block according to one embodiment.
Figure 29B:
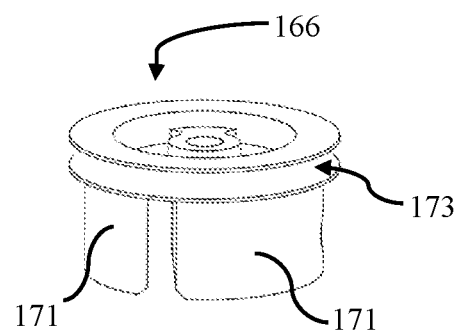
FIG. 29B is a side isometric view of a yaw pulley block according to one embodiment.
Figure 29C:
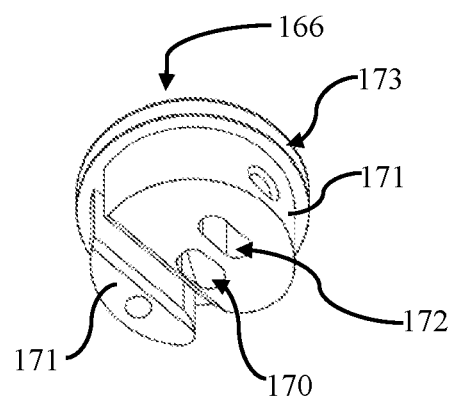
FIG. 29C is a bottom isometric view of a yaw pulley block according to one embodiment.

As mentioned above, in some embodiments, coupled to the connection boss 168 of the yaw pulley 165 is the yaw pulley block 166. FIGS. 29A-29C show multiple views of a yaw pulley block 166 according to one embodiment. In one embodiment, the yaw pulley block 166 is configured to have a top surface which contains a connection pocket 169, with said connection pocket 169 configured to allow the connection boss 168 of the yaw pulley 165 to enter and couple with, thus connecting the yaw pulley 165 with the yaw pulley block 166.

In addition, in some embodiments the connection pocket 169, contains space in which the yaw magnet 164 sits. In these embodiments, the yaw magnet 164 is sandwiched between the yaw pulley 165 and the yaw pulley block 166. In one embodiment, the yaw magnet 164 is configured as a ring magnet. In this embodiment, the yaw magnet 164 is diametrically magnetized, so that as the yaw magnet 164 rotates around its cylindrical axis the magnetic field changes. In this embodiment, the change in magnetic field is measured by rotational positional sensors, with said sensors transmitting the data to processors which convert the change in magnetic field to rotational position data. This conversion is done with knowledge of the physical configuration of the magnet(s) and sensor(s). In this embodiment, several rotational positional sensors are placed around the diametrically magnetized magnet orthogonally to each other. As the diametrically magnetized magnet rotates, the magnetic field it generates also changes relative to the rotational positional sensors. Using simple trigonometry, a combination of two orthogonally placed sensors can determine the direction of the magnetic field by comparing the relative field strength between the sensors. This calculation yields the orientation of the diametrically magnetized magnet and, by extension, the orientation of the stereoscopic camera. Additional rotational positional sensors are placed in this embodiment for redundancy, but the total number of sensor necessary for the absolute orientation calculation will depend on the chosen configuration of the magnet and the sensors.

With the rotational data obtained from the sensors, the system is able to pinpoint how far the stereoscopic camera 143 has been rotated about a yaw axis, and thus obtain the rotational position of the stereoscopic camera 143 during actuation. In other embodiments, the yaw magnet 164 is configured as horseshoe magnet, disc magnet, sphere magnet, cylinder magnet and/or any other magnet shape known in the art. In addition, in different embodiments a variety of rotational positional sensors known in the art that are capable of magnetic field sensing can be used, including but not limited to hall effect sensors, and/or magnetoresistors.

Figure 34C:
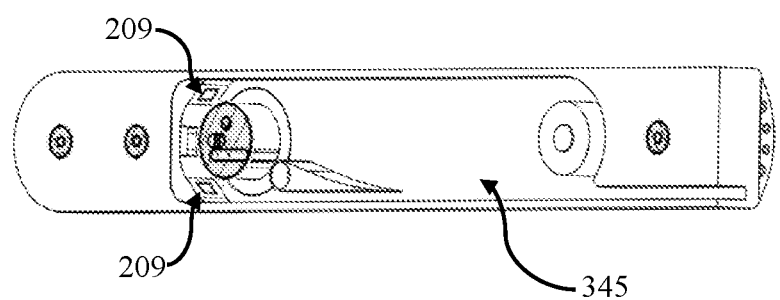
FIG. 34C is an isometric view of an electrical communication component cavity according to one embodiment.

In some embodiments, the electrical communication component cavity 145 of the main camera body 144 contains machined surface apertures for which sensors and capacitors sit inside, with said sensors and capacitors obtaining the rotational position data of the stereoscopic camera 143 about a yaw axis. Similarly, electrical communication component cavity 345 is outfitted with rotational positional sensors 209 and capacitors for obtaining rotational position data of the stereoscopic camera assembly (FIG. 34C). In other embodiments, the electrical communication component cavity contains a separate encasing for which rotational positional sensors and capacitors are held. As stated above, the sensors and capacitors are utilized to obtain the rotational position data of the stereoscopic camera, more specifically the rotational position data of the camera assemblies about a yaw axis. In other embodiments, sensors for determining the rotational position of the camera assemblies are located on the outside of the electrical communication component cavity, while in further embodiments, sensors are located on the main body flex cover or the main camera body.

In some embodiments, the yaw pulley block 166 contains a protrusion 171 on the bottom surface of said yaw pulley block 166. In some embodiments, the protrusion 171 contains a slot for electrical communication components to be routed through said slot and around the protrusion 171 during actuation. In some embodiments, the protrusion 171 is configured to be circular in shape, so to allow electrical communication components to be wrapped around said protrusion during actuation. In other embodiments, the protrusion 171 can take on a variety of shapes that allow electrical communication components to wrap around it during actuation, including but not limited to oval, spherical, and/or cylindrical.

In some embodiments, the protrusion 171 contains a pitch cable aperture 170 configured to allow cable(s) from the pitch actuation assembly 148 to be routed through said yaw actuation assembly 151, and up to the actuators 106 of the camera console assembly 101. Additionally, in some embodiments, the protrusion 171 contains an alignment pocket and a main mount insert pocket 172. In these embodiments, the alignment pocket is configured to allow an alignment pin from the main camera body mount 147 to enter the alignment pocket to align the yaw pulley block 166 and the main camera body mount 147. The main mount insert pocket 172 is configured to allow the stem of the main mount insert 153 to enter and couple the yaw pulley block 166 with the main camera body mount 147. In one embodiment, a set screw hole is located on the side of the protrusion 171. In this embodiment, a set screw enters the set screw hole and couples the main mount insert 153 in the main mount insert pocket 172, thus affixing and securing the main camera body mount 147 to the yaw actuation assembly 151. In other embodiments, different attachment and coupling methods and/or techniques known in the art are utilized to affix the main mount insert 153 to the main mount insert pocket 172 including but not limited to press-fit connections, snap-fit connections, and/or adhesive connections.

In addition, in some embodiments, located around the top surface of the yaw pulley block 166 is a yaw bearing surface 173. In these embodiments, the yaw bearing surface 173 is configured to allow a set of yaw ball bearings 174a to sit in said bearing race. In these embodiments, the yaw actuation assembly 151 rotates inside the main camera body 144, and the main body flex cover 146. In these embodiments, the main body flex cover 146 contains a bearing surface which one set of yaw ball bearings 174a sit and ride along, and the main camera body 144 contains a bearing surface for which another set of yaw ball bearings 174b sit and ride along. In these embodiments, the yaw bearing surface 173 of the yaw pulley block 166 mates with one set of yaw ball bearings 174a and rides along the bearing surface of the main camera body 144, and the other set of yaw ball bearings 174b rides along a bearing surface of the main camera body mount 147 and a bearing surface of the main body flex cover 146. This configuration allows the stereoscopic camera 143 to be rotated about a yaw axis.

Figure 37:
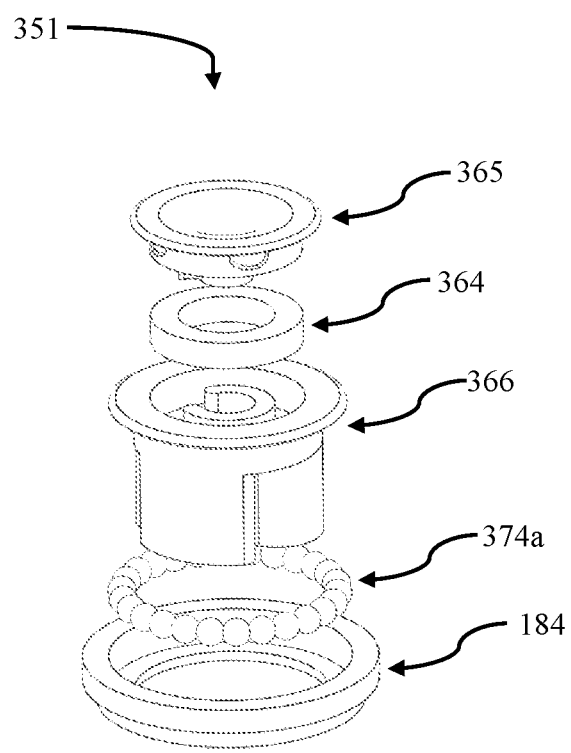
FIG. 37 is an exploded isometric view of a yaw actuation assembly according to one embodiment.

As depicted in FIG. 37, in one embodiment, yaw actuation assembly 351, contains a yaw bearing race 184 for which yaw ball bearings 374a ride along. In this embodiment, yaw ball bearings 374a ride along the yaw bearing race 184 and along a bearing surface on yaw pulley block 366. Additionally, in this embodiment, yaw ball bearings 374b (FIG. 36) ride along a bearing race on the main body flex cover and on the main mount 181 of the main camera body mount 347. As depicted in the illustrative embodiment FIG. 37, yaw actuation assembly 351, contains yaw pulley 365, yaw magnet 364, yaw pulley block 366, yaw ball bearings 374a and yaw bearing race 184. In this embodiment, yaw pulley 365, yaw magnet 364, and yaw pulley block 366, provide the same functions as the embodiments detailed above.

In alternative embodiments, the yaw actuation assembly is fabricated to be directly driven by an actuator. In these embodiments, the actuator replaces the cable pulley systems detailed above. Different types of actuators can be utilized in different embodiments, including but not limited to, piezoelectric motors, linear actuators, rotational motors such as servo motors or stepper motors, or other known actuators in the field. In these embodiments, the actuators provide the rotational movement for the stereoscopic camera about a yaw axis.

As mentioned above, in some embodiments, the stereoscopic camera assembly is constructed to have two camera assemblies, each having an optical axis. In some embodiments, the camera assembles are fabricated to have the same components, while in other embodiments, the camera assemblies are fabricated to contain different components. In alternative embodiments, the camera assemblies are fabricated to contain different variations of the same components. As seen in embodiment shown in FIGS. 21A-21B, in some embodiments, the stereoscopic camera assembly 143 is fabricated to contain a left camera assembly 149 and a right camera assembly 150.

In one embodiment, the left camera assembly 149 is comprised of the front left camera support 162, a back left camera support 175, a camera case 176, a camera connector (not shown), and a camera module 177a (FIGS. 21A-21B). The front left camera support 162 is configured to house and constrain the camera module 177a of the left camera assembly 149. In some embodiments, the front left camera support 162 configured to hold a pitch magnet 180. In this embodiment, the pitch magnet 180 is diametrically magnetized, so that as the pitch magnet 180 rotates around its cylindrical axis the magnetic field changes. In this embodiment, the change in magnetic field is measured by rotational positional sensors, with said sensors transmitting the data to processors which convert the change in magnetic field to rotational position data. With the rotational position data obtained from the sensors, the system is able to pin point how far the stereoscopic camera 143 has been rotated about a pitch axis, and thus obtain the rotational position of the stereoscopic camera 143 about a pitch axis during actuation.

In one embodiment the front left camera support 162 contains an alignment protrusion that mates and couples with an aperture on the pitch actuation assembly 148, thus affixing the front left camera support 162 with the pitch actuation assembly 148. Additionally, in one embodiment, the front left camera support 162 contains alignment pin holes for aligning and coupling the front left camera support 162 with the back left camera support 175. In addition, in one embodiment, the front left camera support 162 contains a screw hole for connection with the pitch pulley 155, as well as another screw hole for connection with an end cap 178. In this embodiment, the end cap is configured to help facilitate insertion of the stereoscopic camera 143. In one embodiment, the endcap 178 has rounded edges so that it can be inserted through the trocar assembly 102 without puncturing the seals of the trocar assembly.

In one embodiment, the front left camera support 162 contains a groove for which the camera connector (not shown) of the left camera assembly 149 sits in. In one embodiment, the camera connector of the left camera assembly 149 is configured as a thirty-pin connection, which connects the camera module 177a of the left camera assembly 149 to electrical communication components that run to the camera rigid board. The camera connector allows video feed obtained by the camera module 177a of the left camera assembly 149 to be transmitted to the camera rigid board, where said rigid board processes the video feed and transmits it to an external processor, which outputs the video feed to an external monitor or head mounted display worn by a surgeon, allowing the surgeon to view the operation site.

As mentioned above, the front left camera support 162 is configured to constrain and house the camera module 177a of the left camera assembly. The camera module is utilized to provide live video feed of the operation site to a surgeon. In some embodiments, the camera module 177a is fabricated to have a lens stack, an infrared filter, a module body and a digital sensor board having a digital sensor. In some embodiments, camera modules currently on the market, such as Raspberry Pi camera modules, e-con System® camera modules, and/or similar camera modules are utilized, while in other embodiments custom made camera modules may be used to provide live video feed.

In one embodiment, the module body of the camera module is fabricated to have an outer and inner edge, with the outer edge being closer to the end-cap of the camera assembly. In addition, in one embodiment, the module body of the camera module is fabricated to allow the digital sensor of the camera module to be shifted such that there is a horizontal displacement from the center of the lens stack of the camera module. The horizontal displacement of the digital sensor from the center of the lens stack, allows the images obtained from the camera module 177a of the left camera assembly 149 and the images obtained from the camera module 177b of the right camera assembly 150 to have a greater overlapping region, thus providing the surgeon with a wider stereoscopic field of view. With a wider stereoscopic field of view, the amount of disparity between the images obtained from the camera module 177a of the left camera assembly 149 and the camera module 177b of the right camera assembly 150 is limited, thus reducing the amount of eye strain experienced by the surgeon.

As mentioned above, in some embodiments, the camera module 177a of the left camera assembly 149 is constrained by the front left camera support 162 and the back-left camera support 175. In these embodiments, the back-left camera support 175 is configured to support the back of camera module 177a of the left camera assembly 149, providing a surface for the back of said camera module to rest on and also providing a surface for the front left camera support 162 to couple to. In one embodiment, the back portion of back left camera support 175 is configured to be a rounded surface such as to allow said support to fit within the camera case 176a. In one embodiment, the back-left camera support 175 contains a slot for electrical communication components to be routed through, with said components being routed through the main camera body mount 147 and to the camera rigid board 115 of the camera console assembly 101. In one embodiment, the back-left camera support 175 contains a plurality of through holes, with said through holes configured to allow a set screw to pass through and adjust the alignment of the camera module 177a. In addition, in some embodiments, the back-left camera support 175 contain a plurality of connection holes to couple and mate the back-left camera support 175 with the front left camera support 162, as well as for attachment of the end cap 178a.

As mentioned above, in some embodiments the back-left camera support 175 is configured to fit within the camera case 176a of the left camera assembly 149. The camera case 176a of the left camera assembly 149 is configured to house the camera module 177a of the left camera assembly 149, the left front camera support 162, the back-left camera support 175, the camera connector of the left camera assembly 149, as well as the electrical communication components routed from the camera module 177a of the left camera assembly 149. The camera case 176a of the left camera assembly 149 is fabricated to prevent liquids and other substances from entering the left camera assembly 149. The camera case 176a of the left camera assembly 149 is configured to slide over the above referenced parts and be constrained on one end by the end cap 178a of the left camera assembly 149, and on the other end by the main camera body mount 147. In one embodiment, the end cap 178a of the left camera assembly 149 is configured as two pieces that mate together. In various embodiments, different connection methods and techniques known in the art are utilized to couple the end cap 178a of the left camera assembly 149 to the camera case 176a of the left camera assembly 149, as well as to couple said case to the main camera body mount 147. Such methods include but are not limited to screw connections, adhesive connections, and/or press-fit connections. In addition, the camera case 176a of the left camera assembly 149 contains an aperture to allow the camera module 177 of the left camera assembly 149 to have clear view of the operation site.

As mentioned above, the stereoscopic camera or stereoscopic camera assembly 143 also comprises the right camera assembly 150 (FIG. 19B). In one embodiment, the right camera assembly 150 is comprised of a front right camera support 179, the back-right camera support 163, a camera module 177b, a camera connector (not shown), and a camera case 176b.

In one embodiment, the front right camera support 179 is configured to support and house the camera module 177b of the right camera assembly 150, similar to how the front left camera support 162 houses and supports the camera module 177a of the left camera assembly 149. In one embodiment, the front right camera support 179 couples directly with the pitch thrust bearing 156 situated inside the main camera body mount 147. In addition, in one embodiment the front right camera support 179 mates and couples with the back-right camera support 163, in the same manner detailed above for the mating and coupling of the front left camera support 162 and the back-left camera support 175. In one embodiment, the back-right camera support 163 contains a protrusion that is configured to fit inside a slot on the pitch thrust bearing 156, thus mating the right camera assembly 150 with the pitch actuation assembly 148.

Additionally, similar to the camera module 177a of the left camera assembly 149, the camera module 177b of the right camera assembly 150 is configured to provide live video feed of the operation site to a surgeon. As detailed above for the camera module 177a of the left camera assembly 149, the camera module 177b of the right camera assembly 150 is comprised of a lens stack, an infrared filter, a module body and a digital sensor. Likewise, in some embodiments, camera modules currently on the market, such as Raspberry Pi camera modules, e-con System® camera modules, and/or similar camera modules are utilized, while in other embodiments custom made camera modules may be used to provide live video feed.

In addition, in some embodiments, the module body of the camera module 177b of the right camera assembly 150 is fabricated to have an inner and outer edge, with the outer edge being closer to the end cap of the camera assembly. Additionally, in some embodiments the module body 177b of the right camera assembly 150 is fabricated to allow the digital sensor of the camera module 177b to be shifted such that there is a horizontal displacement from the center of the lens stack of said camera module. The horizontal displacement of the digital sensor of the camera module 177b from the center of the lens stack of said camera module allows the images obtained from the camera module 177b of the right camera assembly 150 and the images obtained by the camera module 177a of the left camera assembly 150 to have a greater overlapping region, thus providing the surgeon with a wider stereoscopic field of view. In these embodiments, the digital sensor of the camera module 177a of the left camera assembly 149 is shifted to left, and the digital sensor of the camera module 177b contained in the right camera assembly 150 is shifted to the right.

As mentioned above, the right camera assembly 150 contains a camera connector (not shown). The camera connector of the right camera assembly 150 is analogous to the camera connector of the left camera assembly 149, in that the camera connector of the right camera assembly 150 sits within a groove in the front right camera support 179. Likewise, in one embodiment the camera connector of the right camera assembly 150, is configured as a thirty-pin connection, which connects the camera module 177b of the right camera assembly 150 to electrical communication components that run to the camera rigid board 115. The camera connector of the right camera assembly 150 allows video feed obtained by the camera module 177b of the right camera assembly 150 to be transmitted to the camera rigid board 115, where said rigid board processes the video feed and transmits it to an external processor, which outputs the video feed to an external monitor or head mounted display worn by a surgeon, allowing the surgeon to view the operation site.

Furthermore, the camera case 176b of the right camera assembly 150 is analogous to the camera case 176a of the left camera assembly 149, in such that the camera case 176b is configured to house the camera module 177b of the right camera assembly 150, the front right camera support 179, the back left camera support 163, the camera connector of the right camera assembly 150, as well as the electrical communication components routed from the camera module 177b of the right camera assembly 150. The camera case 176b is fabricated to prevent liquids and other substances from entering the right camera assembly 150. In addition, the camera case 176b is configured to slide over the above referenced parts and be constrained on one end by the end cap 178b of the right camera assembly 150, and on the other end by the main camera body mount 147. In one embodiment, the end cap 178b is configured to be two pieces that mate together. In various embodiments, different connection methods and techniques known in the art are utilized to couple the end cap 178b to the camera case 176b, as well as to couple said case to the main camera body mount 147. Such methods include but are not limited to screw connections, adhesive connections, and/or press-fit connections. In addition, the camera case 176b contains an aperture to allow the camera module 177b of the right camera assembly 150 to have clear view of the operation site.

Figure 39A:
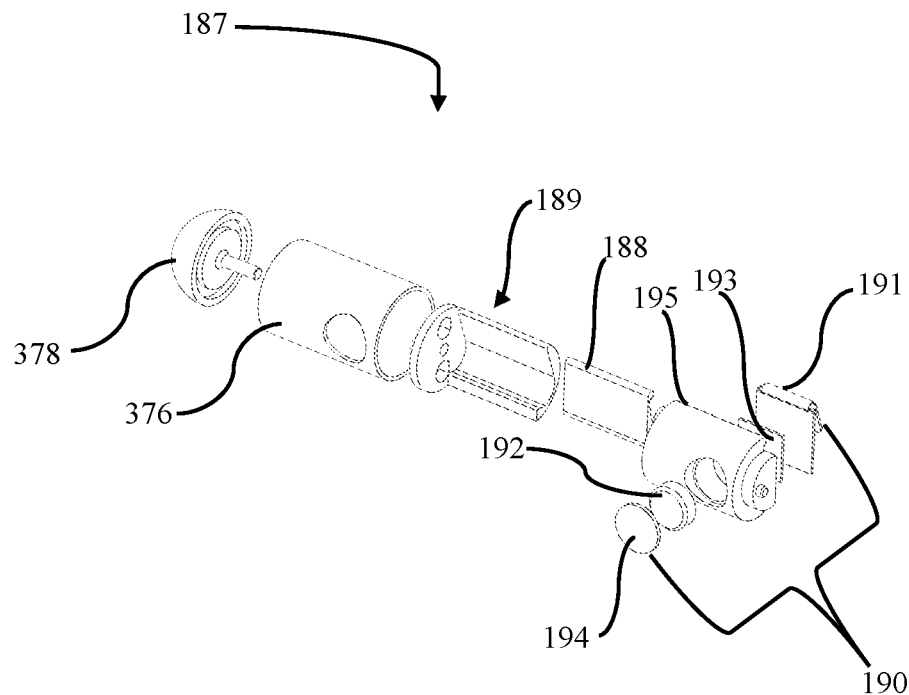
FIG. 39A is an exploded isometric view of a camera assembly according to one embodiment.
Figure 39B:
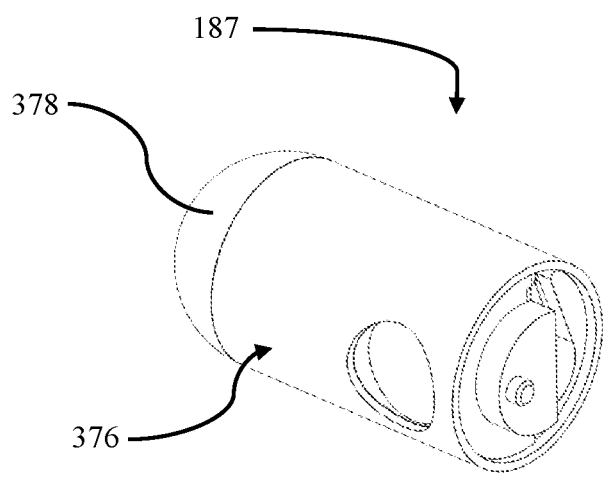
FIG. 39B is an isometric view of a camera assembly according to one embodiment.

As stated above, in some embodiments, the left and right camera assemblies contain the same components and thus are identical. FIGS. 39A-39B, shows an illustrative embodiment of a camera assembly 187. As seen in FIG. 39A, in one embodiment, the camera assembly 187 contains a camera module assembly 190, an electrical communication component retainer 189, a flex mandrel 188, a camera case 376 and an end cap 378. In this embodiment, the camera module assembly 190 contains a camera module body 195, a lens stack 192, an infrared filter 193, a digital sensor board 191 and a camera window 194 (FIG. 39A). In this embodiment, the components of the camera module assembly 190 couple together to form one piece. In some embodiments, a biocompatible adhesive is used to couple all of the components of the camera module assembly 190, while in other embodiment different coupling methods known in the art are utilized. As shown in FIG. 39A, in some embodiments the camera module assembly 190, contains a camera window 194. In these embodiments, the camera window 194 protects the lens stack 192 of the camera assembly 187. In some embodiments, the camera window 194 is constructed out of sapphire glass, while in other embodiments other types of glass known in the field are used and/or a plastic window. In further embodiments, other transparent biocompatible material known in the art capable of protecting the lens stack 192 is used. Additionally, in this embodiment, both sides of the camera module body 195 contain alignment protrusions, to align and mate the camera module assembly 190 with the pitch actuation assembly and align and mate the camera module assembly 190 with the electrical communication component retainer 189, as well as to ensure the left and right camera assemblies are aligned.

As stated in one embodiment, camera assembly 187 contains an electrical communication component retainer 189. The electrical communication component retainer 189 is used for the electrical communication components coupled to the digital sensor board 191 to sit, so as to prevent said communication components from being damaged during actuation of the camera assembly 187. In this embodiment the camera module assembly 190 is coupled to the pitch actuation assembly, with the camera module body 195 holding the electrical communication component retainer 189 in place within the camera case 376. In some embodiments, the camera assembly 187 contains a flex mandrel 188. In these embodiments, the flex mandrel 188 is used to wrap and route electrical communication components coupled to the camera module assembly 190. The flex mandrel 188 is configured to sit within a space on the electrical communication component retainer 189, with said retainer configured to fit and sit within the camera case 376 and mate with the end cap 378, to seal the camera assembly 187.

In various embodiments, components of the stereoscopic camera and camera assemblies can be configured to provide a user experience that is keyed to a specific user allowing the user to view stereo images within a head-mounted display in a manner which feels natural and comfortable. In some embodiments, the interaxial distance between camera assemblies is modified to adjust the depth of the operation site perceived by the user. In some embodiments the digital sensor or digital sensor board of the camera module is shifted relative to the lens stack in order to provide a wider stereoscopic field of view. Additionally, in some embodiments, the focal length of a camera module is adjusted to adjust the focus distance of the camera assemblies.

As mentioned above, the interaxial distance between camera assemblies can be modified to adjust the depth of the operation site perceived by a user. A greater interaxial distance increases the perceived depth, while a smaller interaxial distance decreases the perceived depth of the operation site. With an increase in the interaxial distance, the amount of overlap in images obtained by the camera assemblies will decrease. At distances close to the camera assemblies, the overlap in images may be nonexistent or insufficient for stereoscopic viewing.

Figure 40:
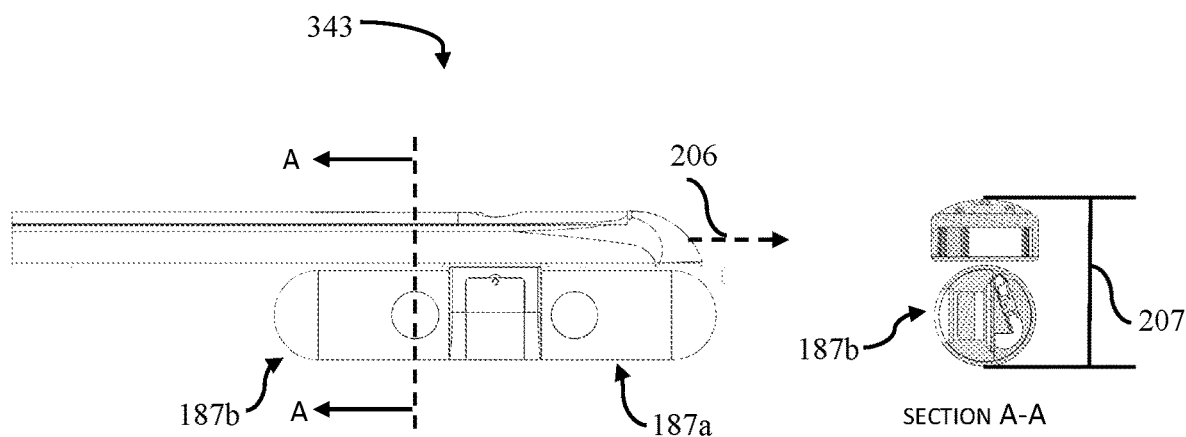
FIG. 40 is a cross-section of a camera assembly according to one embodiment.
Figure 41:
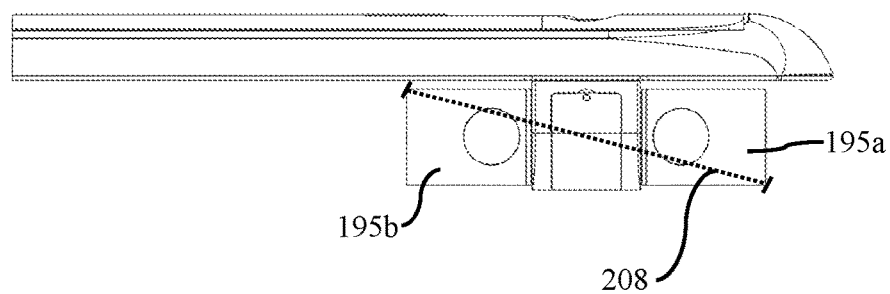
FIG. 41 is front view of a first camera module body and a second camera module body according to one embodiment.
Figure 43:
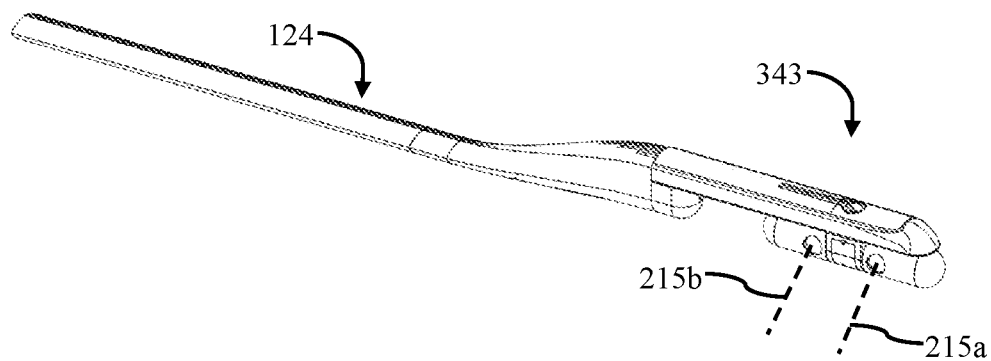
FIG. 43 is an isometric view of a stereoscopic camera assembly in an insertion configuration according to one embodiment.

FIG. 43 shows a stereoscopic camera assembly in an insertion configuration, according to one embodiment. As seen in FIG. 43, in some embodiments, during insertion of a stereoscopic camera assembly, the camera assemblies are arranged such that the optical axes 215a and 215b of the camera modules are orientated perpendicular to the camera support tube. In these embodiments, the stereoscopic camera assembly comprises two camera assemblies, with the first camera assembly having a first camera module and the second camera assembly having a second camera module. In these embodiments, the first camera module has a camera module body having an outer edge and an inner edge, as well as optical components such as, an infrared filter, a digital sensor board, a lens stack, and a camera window. Similarly, the second camera module has a camera module body having an outer edge and inner edge, as well as optical components such as, an infrared filter, a digital sensor board, a lens stack, and a camera window. In these embodiments, the maximum distance from the outer edge of the first camera module body to the outer edge of the second camera module body is configured to be larger than the maximum width of the cross-section of the stereoscopic camera assembly perpendicular to the axis of insertion. FIG. 40 shows a cross section of an embodiment of stereoscopic camera assembly 343, highlighting the maximum width of the cross-section 207 of the stereoscopic camera assembly 343, with the first camera assembly 187b and the second camera assembly 187a orientated perpendicular to an axis 206 of the camera support tube. FIG. 41 shows the maximum distance 208 from the outer edge of the first camera module body 195b to the outer edge of the second camera module body 195a, according to one embodiment. This configuration, allows for an increased interaxial distance between the first and second camera modules to be obtained. With the increased interaxial distance between the camera modules, the stereoscopic camera assembly has an increased ability to visualize parallax and thus allow a user to obtain a greater depth perception of the operation site. In some embodiments, the interaxial distance is selected to maintain a natural and human-like system so that the length of a human arm divided by the human interpupillary distance approximately equals the length of a robotic arm (or tool, instrument or device) divided by the interaxial distance between the camera modules. In alternative embodiments, the interaxial distance between camera modules is configured to be less than the maximum cross-sectional measurement of the robotic device, tool or instrument being inserted.

In addition, as detailed above, the digital sensor or digital sensor board of the camera modules or camera module assembly can be shifted in order to increase the stereoscopic field of view. Similar to the method detailed above for the left camera assembly 149 and the right camera assembly 150, in one embodiment the digital sensor board 191 of the camera module assembly 190 can be shifted such that there is horizontal displacement from the center of the lens stack 192. In this embodiment, the horizontal displacement of the digital sensor board 191, allows the images obtained from one camera assembly 187 and the images obtained from another camera assembly to have a greater overlapping region, thus providing the surgeon or user with a wider stereoscopic field of view. In these embodiments, the digital sensor board of the camera assembly located on the left is shifted left and the digital sensor board of the camera assembly located on the right is shifted to the right. When the shift distance of the digital sensor board in each of the camera assemblies is sufficient, a zero-disparity plane (ZDP) is achieved, at which both images form the camera assemblies completely overlap. As such, by adjusting the interaxial distance between camera assemblies and shifting the digital sensor boards of the said camera assemblies, the stereoscopic view obtained can be maximized.

Additionally, as mentioned above, the focal length of camera assemblies can be adjusted in order to focus the camera modules or module assemblies. The focal length is adjusted by moving the lens stack of the camera assembly towards or away from the digital sensor or digital sensor board. In some embodiments, the lens stack has a threaded exterior that screws into a threaded hole in the camera module body 195 or housing of the camera module 177 depending on the embodiment. In these embodiments, the focal length is adjusted by screwing the lens stack so that it is closer to or farther away from the digital sensor or digital sensor board of the camera assembly. The focal length is adjusted such that the area viewed by the surgeon or user is focused, thus providing a clear image of the operation site. In some embodiments, the lens stack is manually adjusted, while in other embodiments the focal length is adjusted electromechanically utilizing a small actuator such as a linear actuator, or rotary actuator and/or any other small actuator known in the field.

In some embodiments, the camera assembly is outfitted with lights to illuminate the operation site and to help increase the visibility for the surgeon or user. In one embodiment, the end caps of camera assembly are equipped with an array of light emitting diodes (LEDs). The LEDs are powered via wires routed through the camera assembly from outside the patient's body, where said wires are coupled to a power supply. Heat from the LEDs dissipates within the main camera body. In some embodiments, a small amount of sterile saline or other biocompatible fluid flows through the main camera body to cool said camera body, while in other embodiments biocompatible fluid or gas is forced through said camera body for cooling purposes. In these embodiments, biocompatible fluid or gas is routed through the main camera body via a cooling line that is routed from outside the patient body and through the camera assembly. The cooling line is coupled to a fluid or gas source (depending on the embodiment) and a pump, which pumps the fluid or gas through the cooling line. In some embodiments, fluid or gas is continuously pumped and circulated through the cooling line, while in other embodiments, the fluid or gas may be pumped into the line once or a certain time intervals. In other embodiments, a main camera body is outfitted with a temperature sensor to ensure the camera assembly remains within a safe temperature range. In alternative embodiments, LEDs are located on the camera support tube, and/or the main camera body mount. In further embodiments, fiber optics are used in place of LEDs, to illuminate the operation site.

In some embodiments, the camera assembly is outfitted with lens wipers to wipe, brush and/or remove any matter or debris located on the lens of the camera assemblies. In one embodiment, two lens wipers are affixed to the main camera body, one wiper for each camera assembly. The lens wipers are fabricated to extend from the main camera body distally towards the camera assemblies during use. In this embodiment, the lens wipers are affixed to the main camera body via a hinged connection known in the art, such that during use the wipers are able to sway side to side across the lens of the camera assemblies. In other embodiments, lens wipers are rigidly fixed to the main camera body, and the stereoscopic camera is actuated such that the lens of the camera assemblies move across the lens wipers to remove and wipe away any debris or matter. In alternative embodiments, lens wipers are attached directly to the camera assemblies.

In alternative embodiments, lens wipers are fabricated to move up and down from the main camera body towards the camera assemblies. In these embodiments, the lens wipers are configured to be collapsible. The lens wipers expand and extend from the main camera body towards the lens of the camera assemblies, as the lens wipers move up and down, the contact the lens of the camera assemblies and wipe away and remove debris or matter located on the camera assemblies. In some embodiments, the lens wipers are fabricated out of soft biocompatible rubber known in the art, while in other embodiments the lens wipers are fabricated other biocompatible materials known in the art such as soft biocompatible ceramics.

In further embodiments, the camera assembly is outfitted with an irrigation system to spray water or other solutions or fluids, to help remove debris and matter from the camera assemblies, as well as prevent the lens of the camera assemblies from experiencing smudging when debris or matter is wiped away. In these embodiments, the camera assembly is equipped with a fluid line that routed from outside the patient's body and through the camera assembly. The fluid line is coupled to a fluid source and a pump, which pumps the fluid through the fluid line to sprayers located on the main camera body. In this embodiment the sprayers are positioned so that the fluid is sprayed down onto the lens of the camera assemblies. In some embodiments, the pressure at which the fluid is sprayed is controlled by the surgeon or user, while in other embodiments the fluid is set to spray at a set rate. In some embodiments, the camera assembly contains both an irrigation system and lens wipers. In these embodiments, the irrigation system and lens wipers work in conjunction to remove any debris or matter on the camera assemblies.

In some embodiments, the camera assembly is outfitted with peripheral cameras to provide the surgeon or user with real-time images of the operation site during insertion and removal of the camera assembly. In one embodiment, the end caps of the camera assemblies contain peripheral cameras in order to capture the real-time images of insertion and removal. As the camera assembly is inserted the peripheral cameras provide the surgeon with images of the operation site. In these embodiments, the peripheral cameras are orientated to be forward facing with respect to insertion, such that the camera is looking in the direction of insertion so as to provide images of the operation site as the stereoscopic camera is inserted. With the images from the peripheral camera, the surgeon can determine if there are any unforeseen conditions in the operation site, as well as determine if the angle of insertion or the point of insertion needs to be modified.

As stated above, in some embodiments the end caps of both camera assemblies contain peripheral cameras. In these embodiments, one of the peripheral cameras is used to capture images of the operation site during insertion of the stereoscopic camera, and the second peripheral camera is used to capture images of the robotic device, tool and/or instrument being inserted. The second peripheral camera allows the surgeon or user to monitor the insertion of tools, robotic devices or instruments that are being inserted through the trocar assembly. With the images from the second peripheral camera, the surgeon or user can modify the insertion angle or position of the device or instrument being inserted. In addition, during operations, the peripheral cameras are utilized to capture additional images of the operation site. The images from the peripheral cameras during the operation, provide the surgeon or user with imagery that the stereoscopic camera is unable to capture without adjusting the orientation and/or position of the stereoscopic camera.

In alternative embodiments, only the end cap of one of the camera assemblies contains a peripheral camera, while in future embodiments an end cap may contain multiple peripheral cameras. In some embodiments, the peripheral cameras comprise of camera modules known on the market such as Raspberry Pi camera modules, e-con System® camera modules, and/or other similar camera modules known in the field. In other embodiments, the peripheral cameras may comprise custom camera modules.

Insertion

As aforementioned, the robotic camera system is configured to obtain multiple views of an operation site during a surgical procedure, with the camera assembly being inserted into a patient's body. In one embodiment, in order to insert the camera assembly, the trocar assembly is first inserted into the patient's body. In this embodiment, the trocar assembly is inserted in to the patient's body using a standard obturator known in the art. In this embodiment, the obturator punctures the patient's abdominal wall, creating an opening wide enough to allow the trocar to be inserted into the patient's abdomen. The trocar is inserted such that the winged ring sits flush with the exterior wall of the patient's abdomen, with the proximal portion of the trocar assembly located outside of the patient's body. The winged ring is then secured to the patient's body via surgical thread. In one embodiment, two pieces of surgical thread are used to secure the winged ring to the patient's body. In this embodiment, one end of each piece of surgical thread is fastened to screw of the winged ring, and the other end of each piece of surgical thread is sown into the patient's body, thus securing the trocar assembly to the patient's body. With the trocar assembly secured to the patient's body, the patient's abdominal cavity is insufflated, thus expanding the patient's abdominal cavity creating room for the camera assembly to be inserted. In other embodiments, a standard trocar currently on the market and known in the art, is inserted into the patient's body in order to insufflate the patient's abdominal cavity, and then the trocar assembly is inserted into the patient's body.

With the patient's abdominal cavity insufflated, the sheaths of the inflatable seal is inflated, via a pump and/or compression coupled to the air-port. With the sheaths inflated, the camera assembly is inserted through the trocar assembly, and into the patient's abdominal cavity. In one embodiment, prior to insertion of the camera assembly, the stereoscopic camera, is orientated such that the end cap of left camera assembly is first to pass through the trocar assembly and enter the patient's abdominal cavity. In alternative embodiments, the stereoscopic camera is orientated such that the end cap of the right camera assembly is first to pass through the trocar assembly and enter the patient's abdominal cavity. Alternatively, in embodiments where the stereoscopic camera contains a peripheral camera, that end of the stereoscopic camera may be inserted first.

Figure 44:
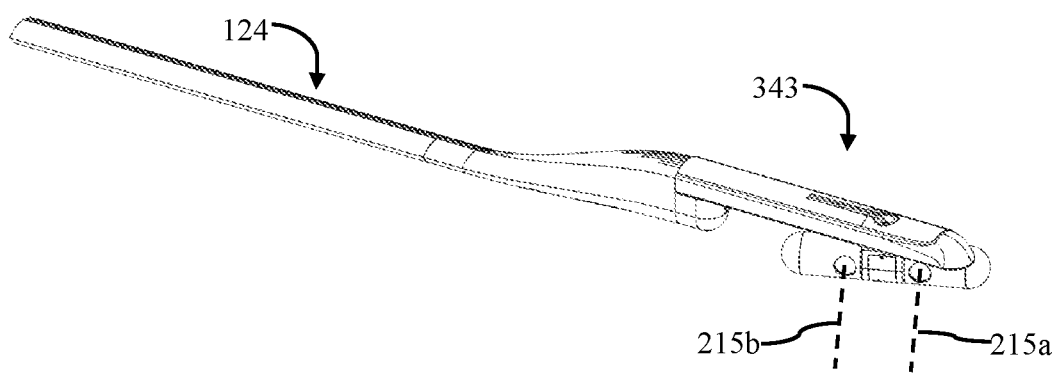
FIG. 44 is an isometric view of a stereoscopic camera assembly in a deployed configuration according to one embodiment.

Once the camera assembly has been inserted into the patient's abdominal cavity, the trocar mating fixture of the camera console assembly is coupled to the trocar, thus securing the camera console assembly and the trocar assembly. This connection, is used to stabilize the system, such that during actuation the camera assembly remains aligned with the trocar assembly such that other devices can pass through the trocar assembly and enter the patient's abdominal cavity. In alternative embodiments, the camera console assembly and the trocar assembly are not coupled to each other, thus allowing the camera console assembly and camera assembly to be rotated while inserted in the patient's body, as well as allowing the camera assembly to be pushed in further into the patient's abdominal cavity and/or pulled back out towards the trocar. FIG. 43 shows an illustrative embodiment of the stereoscopic camera 343 in an insertion configuration. As shown in FIG. 43 in some embodiments during insertion the first optical axis 215b and second optical axis 215a of the camera modules are orientated perpendicular to the camera support tube 124. With the camera assembly inserted in the patient's abdominal cavity, the stereoscopic camera is ready to be actuated. FIG. 44 shows the stereoscopic camera 343 in a deployed configuration according to one embodiment. As illustrated in the embodiment shown in FIG. 44, when the stereoscopic camera 343 is in a deployed configuration the first optical axis 215b and the second optical axis 215a move based on the rotation of the stereoscopic camera.

Once the stereoscopic camera has been inserted into the patient's abdominal cavity, tools, devices and/or instruments can be inserted through the trocar assembly into the patient's abdominal cavity. In one embodiment, prior to insertion of a tool, instrument or robotic device through the trocar assembly, said device, tool or instrument, enters into a seal plug. The seal plug serves as a passage vessel for the tool, device or instrument to be introduced into the patient's abdominal cavity, so as to allow the tool, device or instrument to pass through the seal sub-assembly while maintaining a seal and preventing any carbon dioxide from escaping or leaking out. In one embodiment, the seal plug is configured to have a hollow center for a device, tool or other object to fit within. Prior to insertion into the trocar assembly, the device, tool or other object is inserted into the seal plug. During operation, the seal plug is positioned such that a distal portion of the instrument is outside of the plug with a proximal portion of the instrument encompassed in the plug. As the seal plug is introduced into the trocar assembly, the seal plug passes through the seal sub-assembly, with a proximal portion of the seal plug remaining outside of the seal sub-assembly. The seal plug is fabricated to fill all of the open space in the trocar such that the seals of the seal sub-assembly surround the portion of the seal plug contained within the seal sub-assembly thus creating a seal. The seal plug remains inside the trocar assembly, until the instrument is ready to be removed from the operation field.

Actuation

Figure 42:
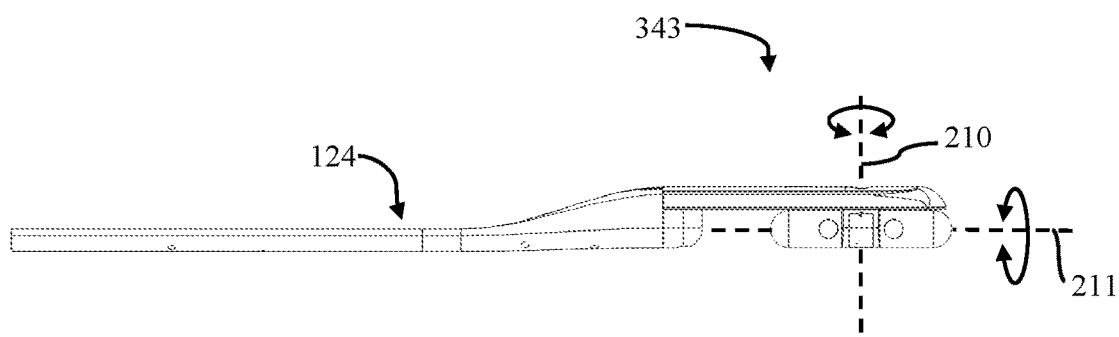
FIG. 42 is a front view of a stereoscopic camera assembly highlighting a yaw axis and pitch axis of rotation according to one embodiment.

The stereoscopic camera is configured to obtain multiple views of an operation site, by actuating the stereoscopic camera to a desired position and orientation. FIG. 42 shows an illustrative embodiment of a stereoscopic camera assembly 343 highlighting the yaw axis 210 and the pitch axis 211 of the camera assembly, according to one embodiment. As illustrated in FIG. 42, in one embodiment, the yaw axis 210 is normal to a plane in which the camera support tube 124 lies, and the pitch axis 211 is perpendicular to the yaw axis 210. As detailed above, in one embodiment the stereoscopic camera is configured to be rotated up and down about a pitch axis 211 and rotated side to side about a yaw axis 210 (FIG. 42). In this embodiment, cable(s) from the pitch actuation assembly and cable(s) from the yaw actuation assembly are routed from the camera assembly to the actuators of the camera console assembly. The actuators are configured to rotate the stereoscopic camera about a pitch axis 211 and a yaw axis 210, by providing actuation forces on cable(s) routed from the pitch actuation assembly and the yaw actuation assembly.

In one embodiment, the stereoscopic camera is actuated by the movement of the surgeon's head. For example, during an operation if the surgeon wishes to view an object located above his current field of view, the surgeon looks up which results in the stereoscopic camera being rotated up about a pitch axis. In this embodiment, as disclosed in International Patent Application No. PCT/US2015/029247 (published as International Patent Publication No. WO2015171614A1), the surgeon wears a virtual-reality head mounted display to view the live camera feed(s) obtained by the stereoscopic camera. Appropriate head-mounted displays (HMDs) such as the Oculus Rift provide the user with a head-mounted view of the operation site, lenses to allow focused view within the display, and a sensor system to provide position and orientation tracking of the display. HMDs such as the Oculus Rift and HTC Vive, have built-in tracking and sensor systems, that obtain raw orientation data for yaw, pitch and roll of the HMD as well as positional data in Cartesian space (x,y,z) of the HMD. However, alternative tracking systems may be used in to provide supplementary position and orientation tracking data of the display in lieu of or in addition to the built-in tracking system of the HMD. Position and orientation sensor systems may include accelerometers, gyroscopes, magnetometers, infrared tracking, computer vision, fiducial tracking, magnetic tracking, laser tracking, ultrasonic tracking, mechanical tracking with encoders, or any other method of tracking at least one of position and orientation, or any combination thereof. The above-mentioned sensor tracking systems can be used to track the head-mounted display as worn by the user, as well as to track the rotational position of the stereoscopic camera during actuation.

In this embodiment, a sensor system tracks position and orientation of the surgeon's head mounted display. The sensor system relays the orientation data to a computer in real time. The position data is not necessary in this embodiment of the camera system since this embodiment of the camera system cannot independently translate in space, however other embodiments of the camera system may rely on the positional data for additional movement or to provide supplementary data. The orientation measurements are presented relative to the HMD's built-in coordinate system. The computer interprets the raw orientation data by transforming the coordinate system of the data from the built-in coordinate system of the HMD to one which matches the coordinate system defined by the camera system. In this embodiment, a simple constant rotation must be applied for this transformation since the built-in coordinate system of the HMD and the defined coordinate system of the camera system are both fixed and known.

The computer also ensures no singularities will be achieved when enforcing the rotation order determined by the physical configuration of the camera actuators. To avoid the natural singularity occurring when the $2^{nd}$ rotation angle approaches 90 degrees (pi/2 radians), an algorithm begins to weigh the $1^{st}$ rotation angle more heavily than the $3^{rd}$ rotation angle as the $2^{nd}$ rotation angle crosses a defined singularity threshold. The computer then transmits the interpreted data to the motor control board which is operatively coupled to the actuators of the camera console assembly.

The motor control board receives the orientation data sent from the computer and determines the necessary control effort needed to drive the actuators to put the camera system in the desired orientation. Physical characteristics of the camera system such as pulley diameters, cable diameters, friction profiles, and actuator constraints, are considered in calculating the actuator commands. In this embodiment of the camera system, the actuator commands are designed using position control to drive the actuators to a specific position which will result in a desired output orientation of the stereoscopic camera. In other embodiments of the camera system, using torque control or more advanced techniques, a control torque may be calculated instead to command the actuators to drive the stereoscopic camera to the desired orientation.

The motor control board transmits these actuation commands to the actuators of the camera console assembly, such that the actuators actuate the stereoscopic camera to follow the movement of the surgeon's head in real time. In this embodiment, position and/or orientation data obtained from rotational positional sensors operatively connected to the pitch actuation assembly and the yaw actuation assembly is simultaneously transmitted back to the motor control board, such that the motor control board constantly knows the position and orientation of the stereoscopic camera, so as to allow the motor control board to adjust the pan and tilt of the stereoscopic camera to align with the head movements of the surgeon. In other embodiments, position and/or orientation sensing of pitch and/or yaw actuation can be omitted if the actuation of the stereoscopic camera is sufficiently rigid, such that actuator (motor) position can be assumed to directly correlate to the pitch and/or yaw position of the stereoscopic camera. In alternative embodiments, position and/or orientation sensing is omitted entirely, with the stereoscopic camera actuated about the pitch and yaw axis relative to previous positions and/or orientations.

The camera rigid board processes the video feed obtained from the stereoscopic camera. The images and/or video feed obtained from the camera modules of the stereoscopic camera are displayed on the head-mounted display. The images and/or video feeds obtained from the camera assembly on the left side of the stereoscopic camera are displayed to the surgeon's left eye and images and/or video feed obtained from the camera assembly on the right side of the stereoscopic camera being displayed to the surgeon's right eye. The combination of the left eye view and the right eye view obtained from the camera assemblies of the stereoscopic camera provides the surgeon with a stereoscopic view of the operation site. In some embodiments, software is utilized to adjust the views of the stereoscopic camera slightly to compensate for any difference between the position of the stereoscopic camera and the surgeon's head position.

As stated above, the camera modules and camera module assembly contain digital sensor board which captures the images and/or video feeds of the operation site. The digital sensor board of the camera modules and module assemblies are in communication with a video processor board. In different embodiments, a variety of video processor boards are utilized including but not limited to various models of the Raspberry Pi, eInfochip's DVPB, NVIDIA jetson board or other known video processor boards known in the art. The digital sensor board communicates to the video processor board via MIPI communication protocol. In some embodiments, the image and/or video feed from each camera module is sent to its own video processor board, while in other embodiments, both image and/or video feed from both camera modules are sent to the same video processor board. The video processor board or boards is in communication with a computer which encodes the image/video feed using video rendering software. In some embodiments, FFmpeg is the video rendering software used, while in alternative embodiments other video rendering software known in field is utilized. The computer then sends the image and/or video feed obtained from the camera modules or module assemblies to a virtual reality computer application via network streaming. The virtual reality computer application takes the image and/or video feed from the network stream and decodes it using the video rendering software. From the video rendering software, the image and/or video feed is sent to the HMD which is done through the software of the HMD.

Computer System

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

The invention claimed is:

1. A system comprising:
   a. a console assembly comprising:
      i. a first actuator,
      ii. a first actuator pulley operably coupled to the first actuator, and
      iii. a cable;
   b. a trocar assembly operably coupled to the console assembly, the trocar assembly comprising:
      i. a trocar having an inner and an outer diameter, and
      ii. a seal sub-assembly operably coupled to the trocar, the seal sub-assembly comprising at least one seal;
   c. a camera assembly operably coupled to the console assembly, the camera assembly comprising:
      i. a camera support tube having a distal end and a proximal end, the distal end of the camera support tube configured to pass at least partially through the trocar,
      ii. a stereoscopic camera assembly operably coupled to the distal end of the camera support tube and configured to pass through the trocar and be positioned in an internal body cavity while operably coupled to the distal end of the camera support tube, the stereoscopic camera assembly comprising:
         1. a main camera body defining a cavity,
         2. a first camera module having a first optical axis,
         3. a second camera module having a second optical axis,
         4. a pitch actuation assembly, and
         5. a yaw actuation assembly, the pitch and yaw actuation assemblies providing motion of the first camera module and the second camera module with respect to the distal end of the camera support tube along at least two rotational degrees of freedom, wherein the cable operably couples the first actuator pulley to one of the pitch actuation assembly or the yaw actuation assembly; and
   d. at least one rotational positional sensor configured to detect rotation of the stereoscopic camera assembly about at least one of a pitch axis or a yaw axis, wherein the yaw axis is normal to a plane in which the camera support tube lies, and the pitch axis is perpendicular to the yaw axis.

2. The system of claim 1, wherein the cable comprises a pitch cable operably coupling the pitch actuation assembly to the first actuator pulley so that actuation of the first actuator rotates the stereoscopic camera assembly about the pitch axis.

3. The system of claim 2, wherein the console assembly further comprises:
   a. a second actuator and
   b. a second actuator pulley operably coupled to the second actuator.

4. The system of claim 3, further comprising a yaw cable operably coupling the second actuator to the second actuator pulley so that actuation of the second actuator rotates the stereoscopic camera assembly about the yaw axis.

5. The system of claim 4, the console assembly further comprising a first redirecting pulley disposed along a path of the pitch cable between the first actuator pulley and the pitch actuation assembly, the first redirecting pulley being configured to redirect the path of the pitch cable from the first actuator pulley to a first cable lumen defined by the camera support tube.

6. The system of claim 5, the console assembly further comprising a second redirecting pulley disposed along a path of the yaw cable between the second actuator pulley and the yaw actuation assembly, the second redirecting pulley being configured to redirect the path of the yaw cable from the second actuator pulley to a second cable lumen defined by the camera support tube.

7. The system of claim 4, the console assembly further comprising a redirecting pulley disposed along a path of the yaw cable between the second actuator pulley and the yaw actuation assembly, the redirecting pulley being configured to redirect the path of the yaw cable from the second actuator pulley to a second cable lumen defined by the camera support tube.

8. The system of claim 1, wherein the seal sub-assembly further comprises a second seal.

9. The system of claim 1, wherein the stereoscopic camera assembly further comprises a peripheral camera.

10. The system of claim 1, wherein the first optical axis of the first camera module and the second optical axis of the second camera module have an interaxial distance configured to provide stereo vision.

11. The system of claim 1, wherein the stereoscopic camera assembly has an insertion configuration and a deployed configuration, and wherein, in the insertion configuration, the first optical axis of the first camera module and the second optical axis of the second camera module are orientated perpendicular to the camera support tube.

12. The system of claim 11, wherein the first camera module comprises a first camera module body having a first outer edge, wherein the second camera module comprises a second camera module body having a second outer edge, and wherein a maximum distance from the first outer edge of the first camera module body to the second outer edge of the second camera module body is greater than a maximum width of a cross-section of the stereoscopic camera assembly taken perpendicular to an axis of the camera support tube.

13. The system of claim 1, wherein the console assembly further comprises a plurality of actuators.

14. The system of claim 1, wherein the trocar assembly further comprises a trocar mating fixture defining a pass through having a pass through axis, wherein the pass through axis is parallel with a longitudinal axis of the camera support tube, and wherein the pass though is configured to permit access through the camera console assembly and through the trocar assembly.

15. A camera assembly comprising:
  a. a camera support tube having a distal end and a proximal end, the distal end of the camera support tube configured to pass at least partially through a trocar;
  b. a stereoscopic camera assembly operably coupled to the distal end of the camera support tube and configured to pass through the trocar and be positioned in an internal body cavity while operably coupled to the distal end of the camera support tube, the stereoscopic camera assembly comprising:
    i. a main camera body operably coupled to the distal end of the camera support tube, wherein the main camera body defines an electrical component cavity,
    ii. a first camera module having a first optical axis,
    iii. a second camera module having a second optical axis,
    iv. an externally-driven actuation system comprising a pitch actuation assembly and a yaw actuation assembly, the actuation system providing motion of the first camera module and the second camera module with respect to the distal end of the camera support tube along at least two rotational degrees of freedom; and
    v. an electrical communication component; and
  c. at least one rotational positional sensor configured to detect rotation of the stereoscopic camera assembly about at least one of a pitch axis or a yaw axis, wherein the yaw axis is normal to a plane in which the camera support tube lies, and the pitch axis is perpendicular to the yaw axis, and
  wherein the electrical communication component is configured to transmit information captured by at least one of the first camera module, the second camera module, or the at least one rotational positional sensor physically, and
  wherein the electrical communication component is physically configured to permit the stereoscopic camera assembly to be actuated in the at least two rotational degrees of freedom, and
  wherein the electrical communication component can be bent to a minimum allowable bend radius without being damaged or rendered unusable.

16. The camera assembly of claim 15, wherein the actuation system is cable driven.

17. The camera assembly of claim 15, wherein the actuation system is motor driven.

18. The camera assembly of claim 15, wherein the yaw actuation assembly is configured to actuate the stereoscopic camera assembly about the yaw axis.

19. The camera assembly of claim 15, wherein the pitch actuation assembly is configured to actuate the stereoscopic camera assembly about the pitch axis.

20. The camera assembly of claim 15, wherein the pitch actuation assembly is configured to actuate the stereoscopic camera assembly about the pitch axis independent of the yaw actuation assembly.

21. The camera assembly of claim 15, wherein the stereoscopic camera assembly further comprises a first peripheral camera.

22. The camera assembly of claim 21, wherein the stereoscopic camera assembly further comprises a second peripheral camera.

23. The camera assembly of claim 15, wherein the stereoscopic camera assembly further comprises a lighting source operably coupled to a power supply.

24. The camera assembly of claim 15, wherein the electrical communication component comprises a flexible printed circuit board (FPCB).

25. The camera assembly of claim 15, wherein the electrical communication component comprises a printed circuit board (PCB).

26. The camera assembly of claim 15, further comprising a flex shield that provides a protective casing for the electrical communication component.

27. The camera assembly of claim 26, wherein the flex shield comprises side walls.

28. The camera assembly of claim 15, wherein the electrical communication component is situated in the electrical component cavity defined by the main camera body.

29. The camera assembly of claim 28, further comprising a flex wrap guide and a constant-force spring.

30. The camera assembly of claim 28, wherein the main camera body further defines machined surface apertures.

31. The camera assembly of claim 15, further comprising an electrical communication component retainer.

32. The camera assembly of claim 15, wherein the first optical axis of the first camera module and the second optical axis of the second camera module have an interaxial distance configurable to provide stereo vision.

33. The camera assembly of claim 15, wherein the stereoscopic camera assembly has an insertion configuration and a deployed configuration, and wherein, in the insertion configuration, the first optical axis of the first camera module and the second optical axis of the second camera module are orientated perpendicular to the camera support tube.

34. The camera assembly of claim 33, wherein the first camera module comprises a first camera module body having a first outer edge,
wherein the second camera module comprises a second camera module body having a second outer edge,
and wherein a maximum distance from the first outer edge of the first camera module body to the second outer edge of the second camera module body is greater than a maximum width of a cross-section of the stereoscopic camera assembly taken perpendicular to an axis of the camera support tube.

35. The camera assembly of claim 16, wherein the at least one rotational positional sensor is configured to detect rotation about the pitch axis; and
wherein the camera assembly further comprises a second rotational positional sensor configured to detect rotation of the stereoscopic camera assembly about the yaw axis.

36. A camera assembly comprising:
a. a camera support tube having a distal end and a proximal end, the distal end of the camera support tube configured to pass at least partially through a trocar;
b. a stereoscopic camera assembly operably coupled to the distal end of the camera support tube and configured to pass through the trocar and be positioned in an internal body cavity while operably coupled to the distal end of the camera support tube, the stereoscopic camera assembly having an insertion configuration and a deployed configuration, the stereoscopic camera assembly comprising:
  i. a main camera body operably coupled to the distal end of the camera support tube, wherein the main camera body defines an electrical component cavity,
  ii. a first camera module having a first optical axis, the first camera module comprising a first camera module body having a first outer edge,
  iii. a second camera module having a second optical axis, the second camera module comprising a second camera module body having a second outer edge such that a maximum distance from the first outer edge of the first camera module body to the second outer edge of the second camera module body is greater than a maximum width of a cross-section of the stereoscopic camera assembly taken perpendicular to an axis of the camera support tube, and
  iv. an externally-driven actuation system comprising a pitch actuation assembly and a yaw actuation assembly, the actuation system providing motion of the first camera module and the second camera module with respect to the distal end of the camera support tube along at least two rotational degrees of freedom; and
c. at least one rotational positional sensor configured to detect rotation of the stereoscopic camera assembly about at least one of a pitch axis or a yaw axis, wherein the yaw axis is normal to a plane in which the camera support tube lies, and the pitch axis is perpendicular to the yaw axis, and
wherein, in the insertion configuration, the first optical axis of the first camera module and the second optical axis of the second camera module are orientated perpendicular to the camera support tube.

37. The camera assembly of claim 36, wherein the pitch actuation assembly is configured to actuate the stereoscopic camera assembly about the pitch axis independent of the yaw actuation assembly.

38. The camera assembly of claim 36, wherein the at least one rotational positional sensor is configured to detect rotation about the pitch axis; and
wherein the camera assembly further comprises a second rotational positional sensor configured to detect rotation of the stereoscopic camera assembly about the yaw axis.

* * * * *